(12) United States Patent
Kiani

(10) Patent No.: US 12,059,582 B2
(45) Date of Patent: Aug. 13, 2024

(54) IMPLANTABLE DUAL MODE ULTRASONIC DEVICE

(71) Applicant: The Penn State Research Foundation, University Park, PA (US)

(72) Inventor: Mehdi Kiani, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 614 days.

(21) Appl. No.: 17/283,983

(22) PCT Filed: Oct. 11, 2019

(86) PCT No.: PCT/US2019/055763
§ 371 (c)(1),
(2) Date: Apr. 9, 2021

(87) PCT Pub. No.: WO2020/077168
PCT Pub. Date: Apr. 16, 2020

(65) Prior Publication Data
US 2021/0346726 A1    Nov. 11, 2021

Related U.S. Application Data

(60) Provisional application No. 62/744,367, filed on Oct. 11, 2018.

(51) Int. Cl.
*A61N 7/00* (2006.01)
*A61B 8/00* (2006.01)
(Continued)

(52) U.S. Cl.
CPC .............. *A61N 7/00* (2013.01); *A61B 8/0808* (2013.01); *A61B 8/42* (2013.01); *A61B 8/4472* (2013.01);
(Continued)

(58) Field of Classification Search
CPC .............. A61N 7/00; A61N 2007/0026; A61N 2007/0052; A61N 1/37223; A61N 1/37235
See application file for complete search history.

(56) References Cited

U.S. PATENT DOCUMENTS 9,387,320 B2   7/2016 Wingeier et al.
9,549,708 B2   1/2017 Mercanzini et al.
(Continued)

FOREIGN PATENT DOCUMENTS

| CN | 106621287 A | 5/2017 |
|---|---|---|
| KR | 10 2017 0057457 A | 5/2017 |
| WO | 2018114858 A1 | 6/2018 |

OTHER PUBLICATIONS

Ibrahim, A. et al. "A Comprehensive Comparative Study on Inductive and Ultrasonic Wireless Power Transmission to Biomedical Implants" IEEE Sensors Journal, vol. 18, No. 9, Mar. 5, 2018; < DOI: 10.1109/ISEN.2018.2812420>, entire document.
(Continued)

*Primary Examiner* — Colin T. Sakamoto
(74) *Attorney, Agent, or Firm* — DINSMORE & SHOHL LLP

(57) ABSTRACT

A method and system of neural stimulation and imaging of nervous system of a subject. The method includes the steps of providing an interface device operable to generate an ultrasonic beam for neuromodulation and imaging of a targeted neural structure of a subject, implanting the interface device in the subject, and providing and disposing an external coil array over the targeted neural structure of the subject, wherein the external coil array is wirelessly powering and communicating with the interface device.

22 Claims, 28 Drawing Sheets

(51) Int. Cl.
  *A61B 8/08*   (2006.01)
  *A61N 1/05*   (2006.01)
  *A61N 1/372*  (2006.01)
(52) U.S. Cl.
  CPC .......... *A61B 8/4483* (2013.01); *A61B 8/4488* (2013.01); *A61B 8/4494* (2013.01); *A61B 8/565* (2013.01); *A61N 1/0534* (2013.01); *A61N 1/37223* (2013.01); *A61N 1/37235* (2013.01); *A61N 2007/0026* (2013.01); *A61N 2007/0047* (2013.01); *A61N 2007/0052* (2013.01)

(56) References Cited

U.S. PATENT DOCUMENTS

| | | |
|---|---|---|
| 9,730,649 B1 | 8/2017 | Jepsen |
| 2009/0198306 A1 | 8/2009 | Goetz et al. |
| 2014/0200489 A1 | 7/2014 | Behar et al. |
| 2015/0099963 A1 | 4/2015 | Navarro de Lara et al. |
| 2017/0025842 A1 | 1/2017 | Peterson |
| 2017/0080210 A1 | 3/2017 | Mercanzini et al. |
| 2017/0125892 A1 | 5/2017 | Arbabian et al. |
| 2017/0258352 A1 | 9/2017 | Wood et al. |
| 2018/0085605 A1 | 3/2018 | Maharbiz et al. |

OTHER PUBLICATIONS

International Search Report dated Jan. 2, 2020; International Application No. PCT/US19/55763.

FIG. 2A
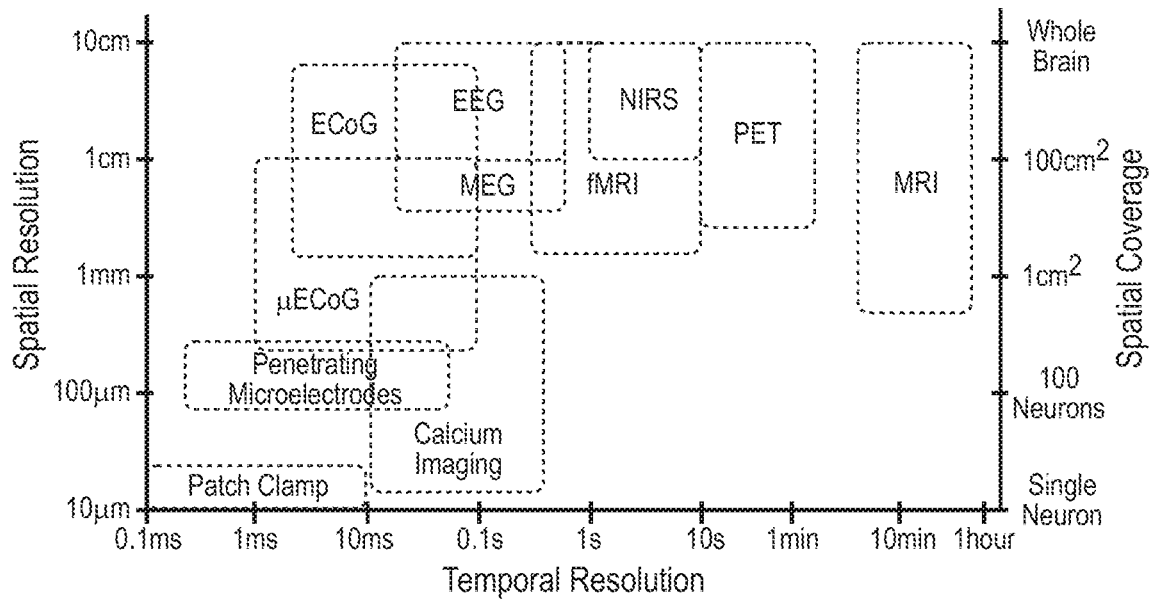
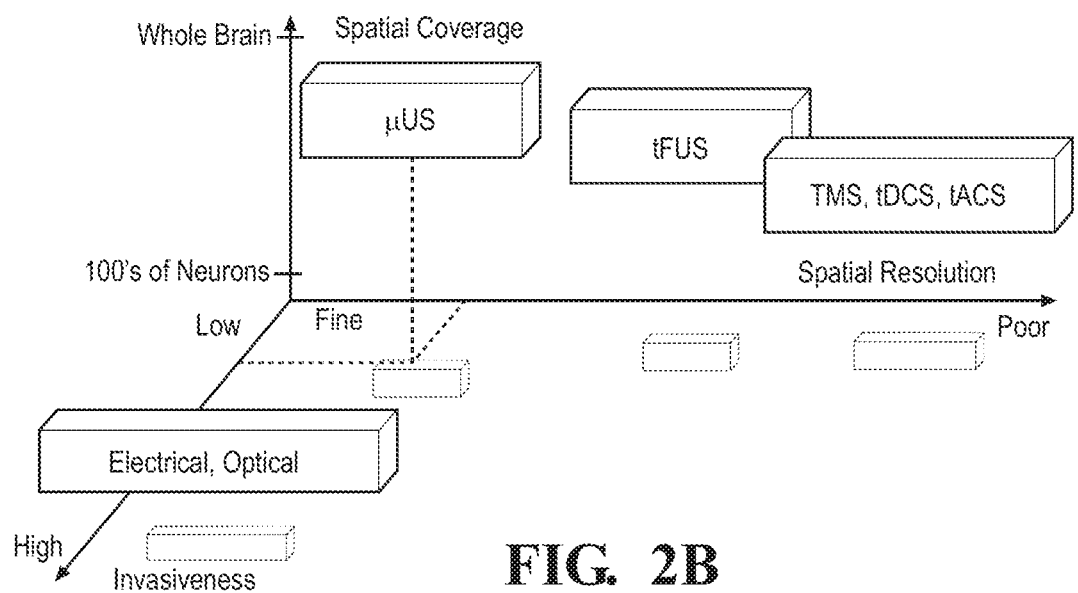
FIG. 2B

FIG. 7A
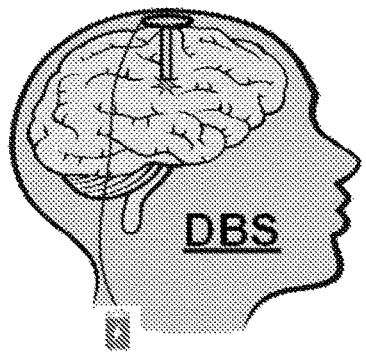
FIG. 7B
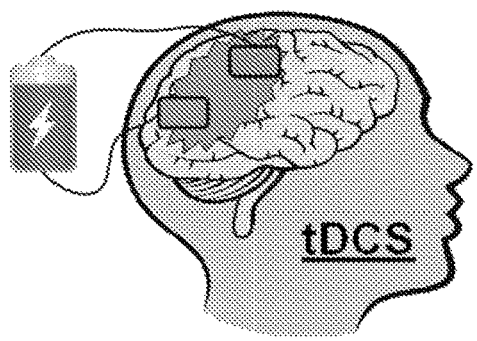
FIG. 7C
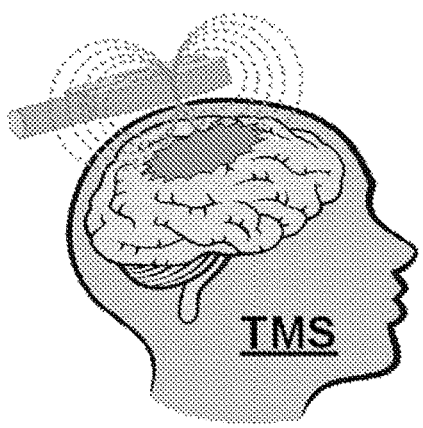
FIG. 7D
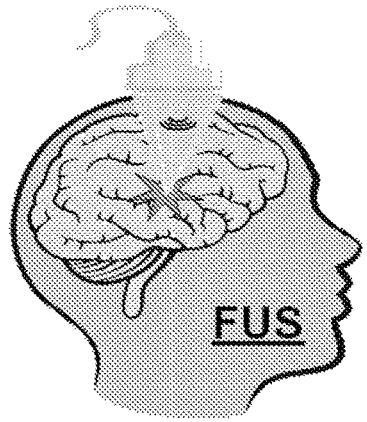
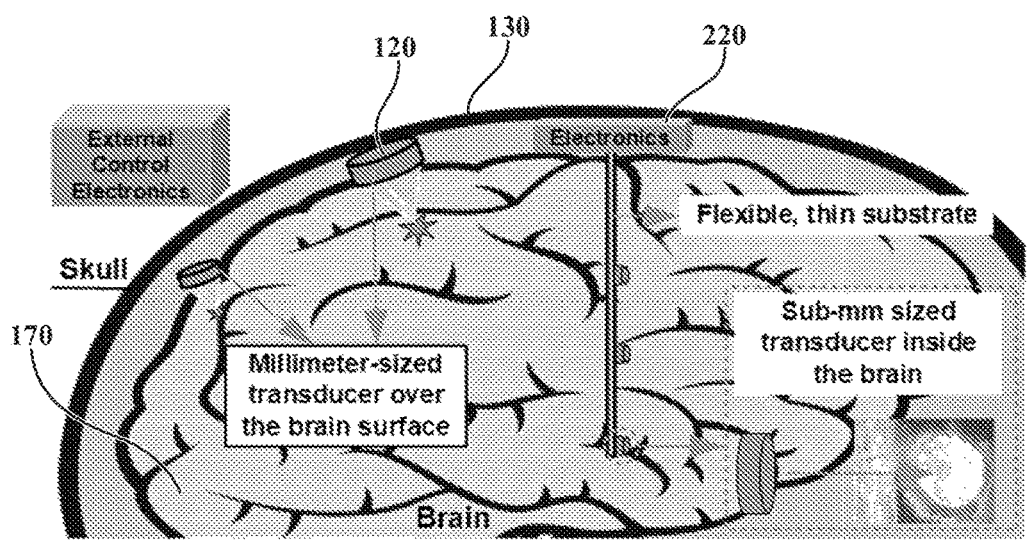
FIG. 8

FIG. 9A
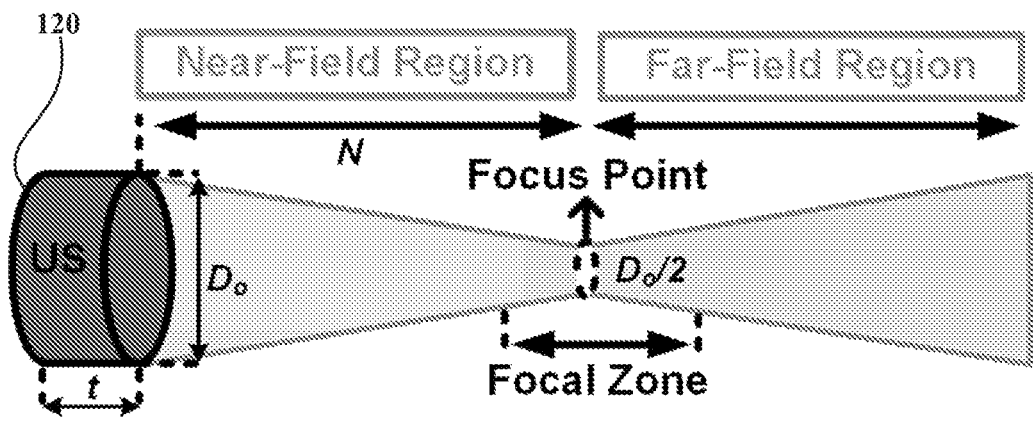
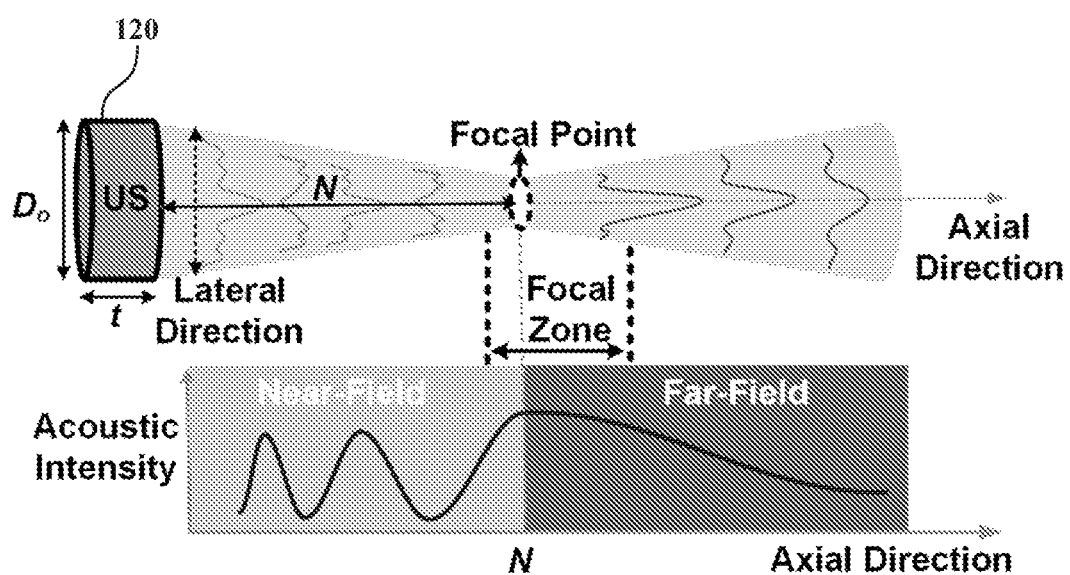
FIG. 9B

FIG. 10A
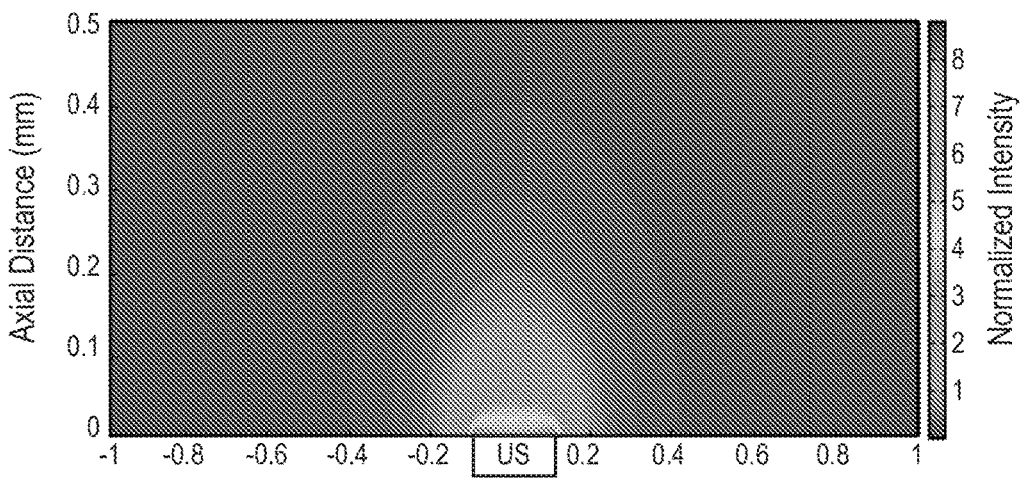
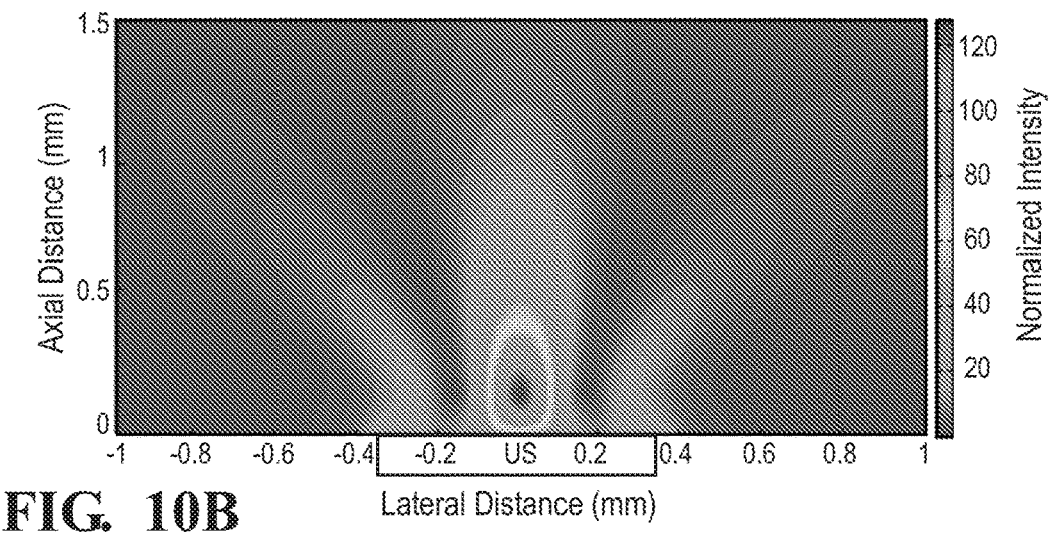
FIG. 10B
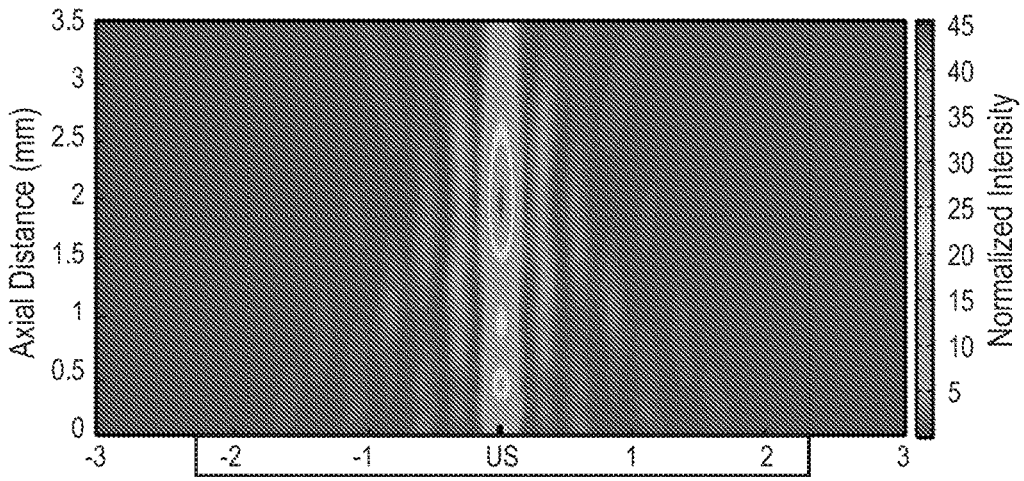
FIG. 10C

FIG. 13A
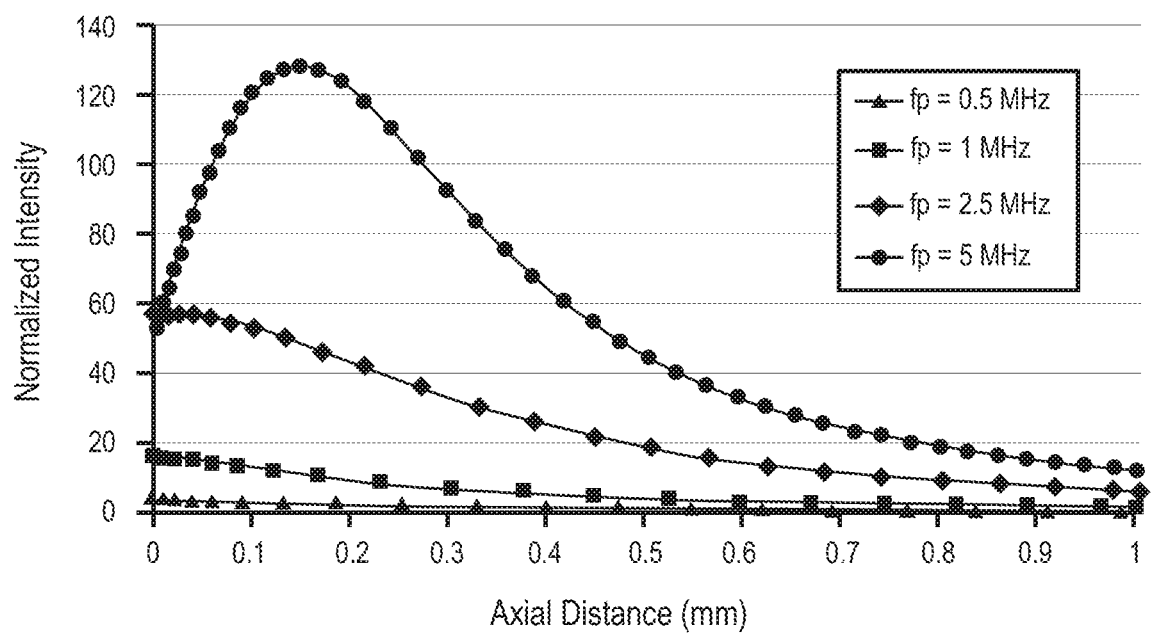
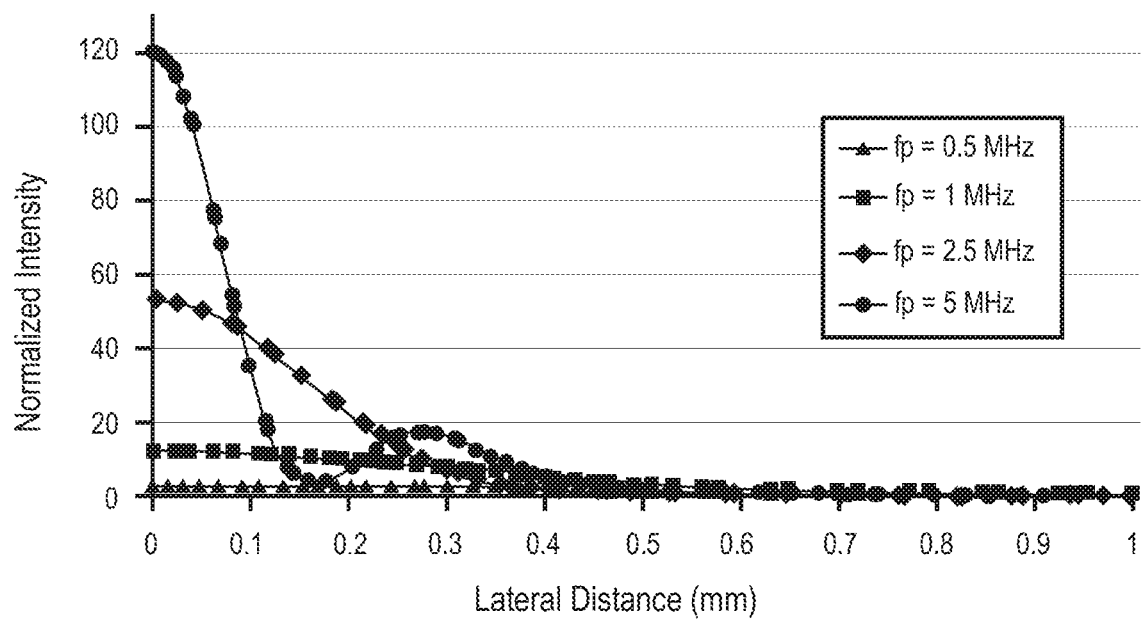
FIG. 13B

FIG. 14C
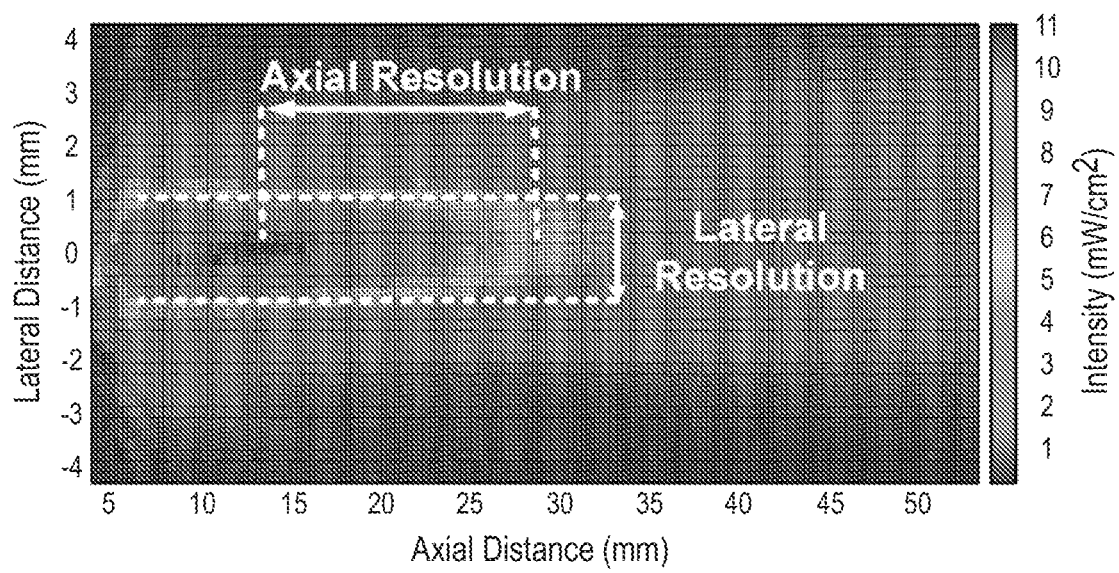
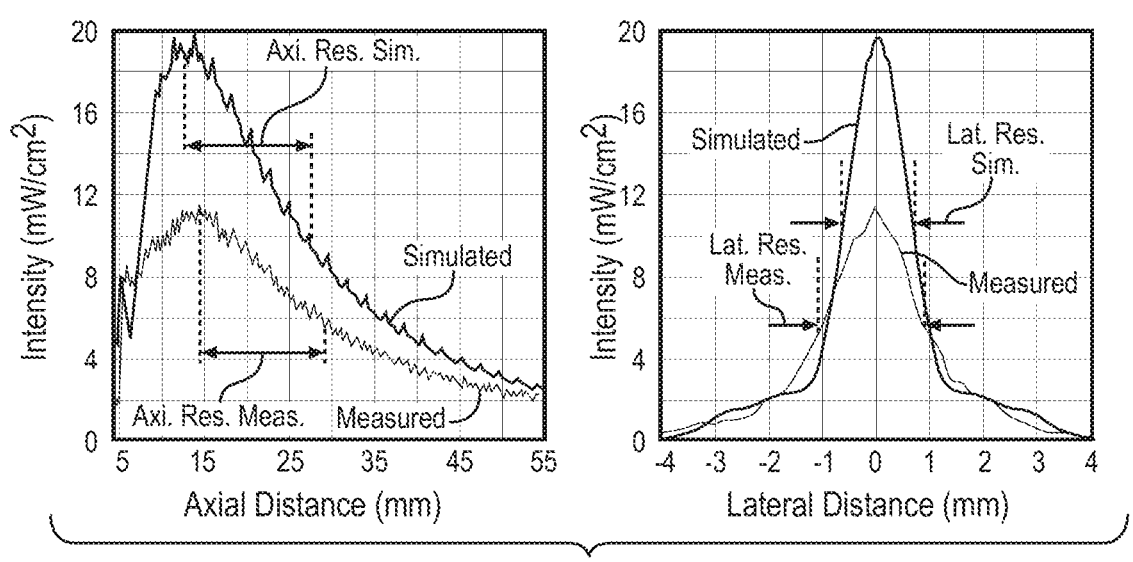
FIG. 14D

FIG. 15A
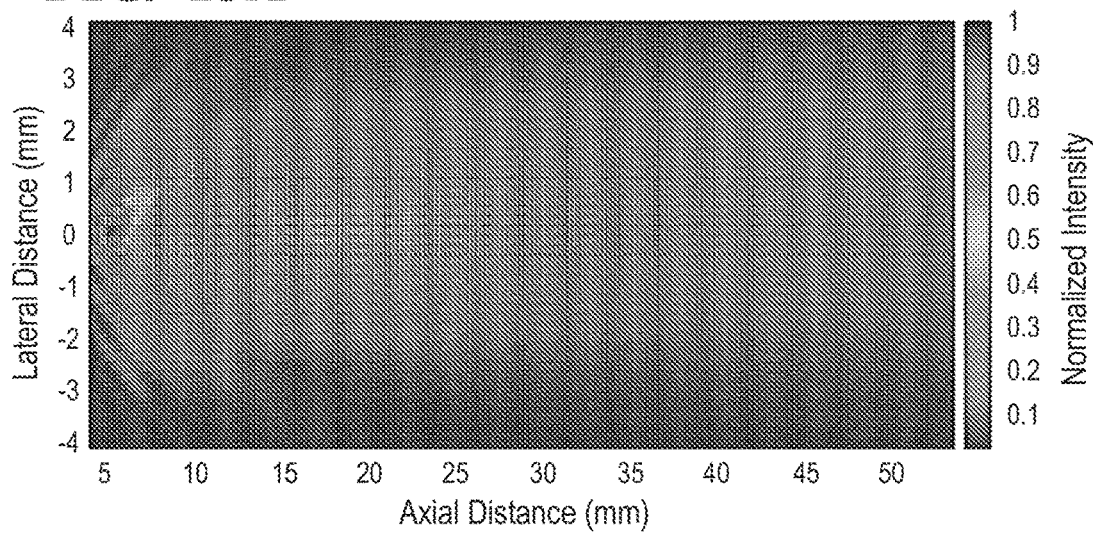
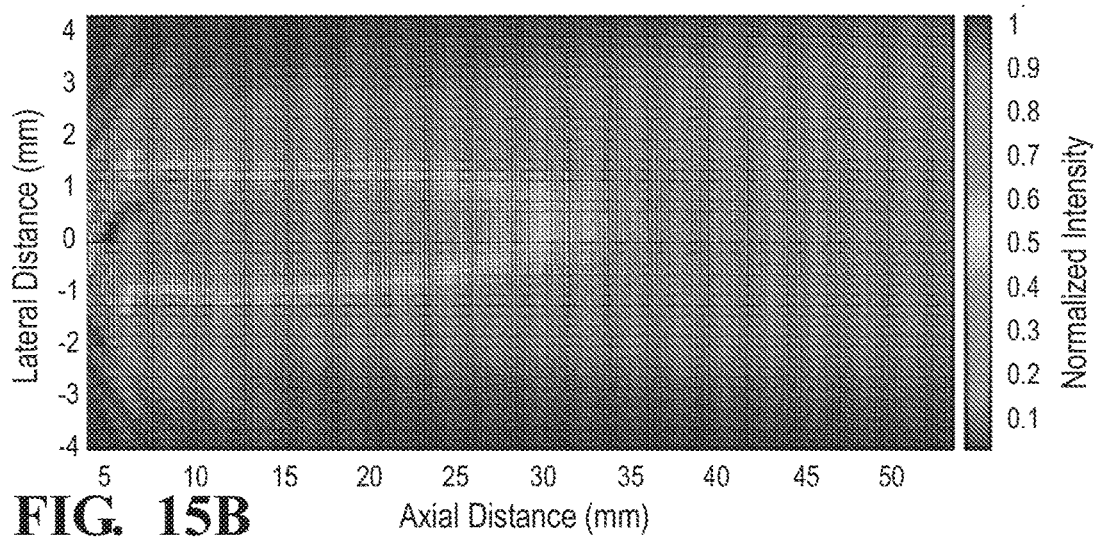
FIG. 15B
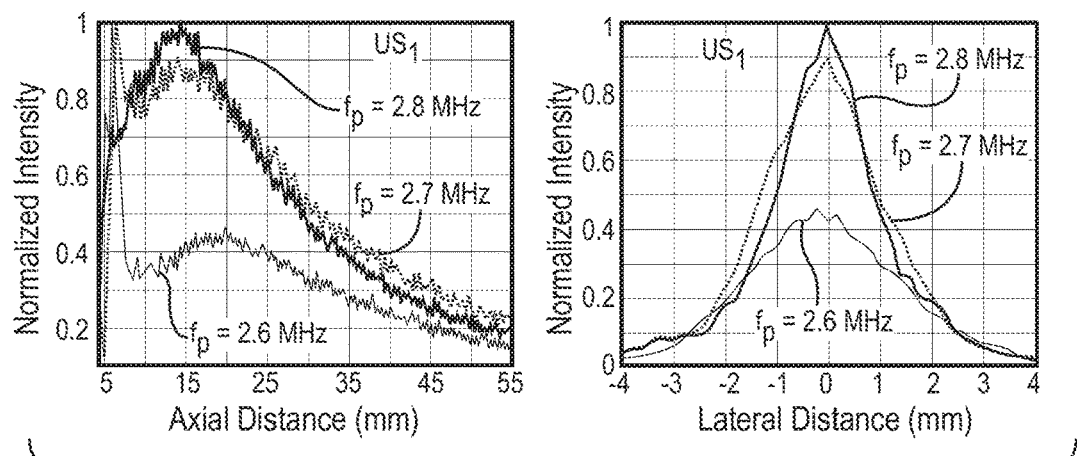
FIG. 15C

FIG. 16A
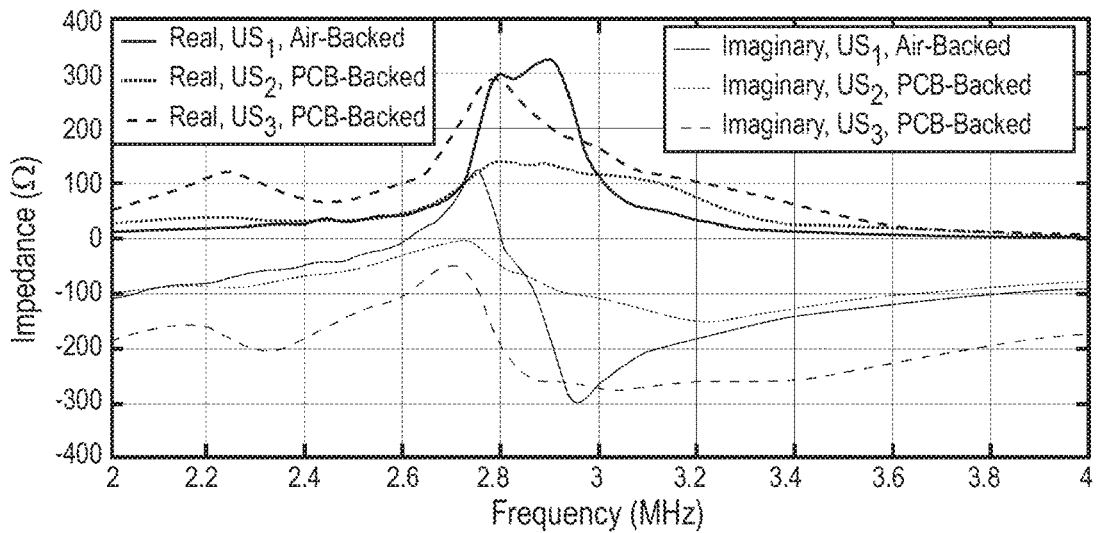
FIG. 16B
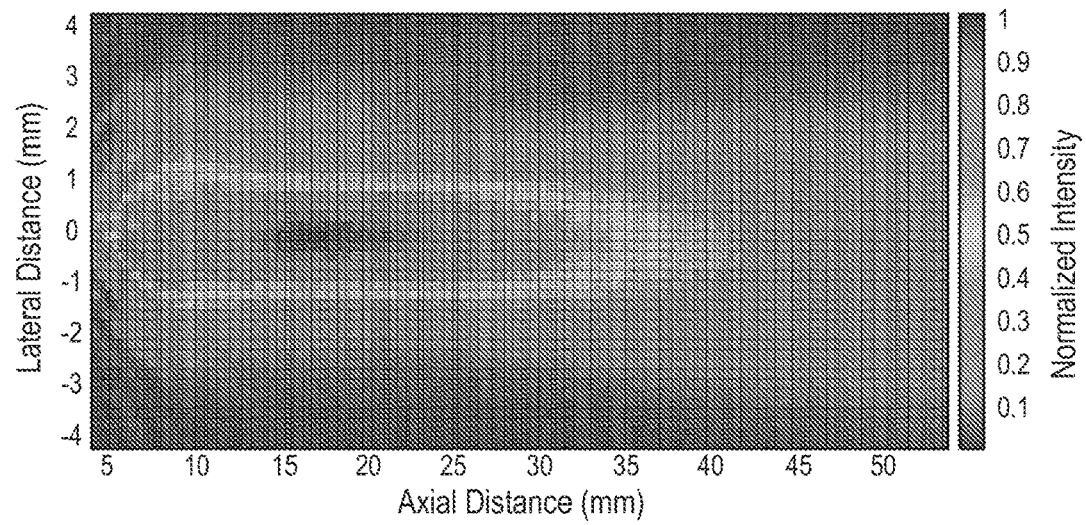
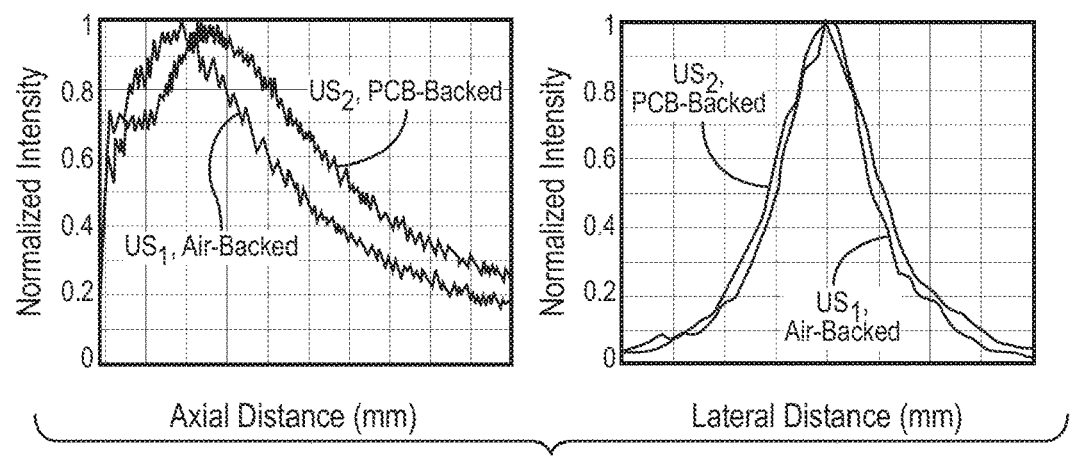
FIG. 16C

FIG. 18A
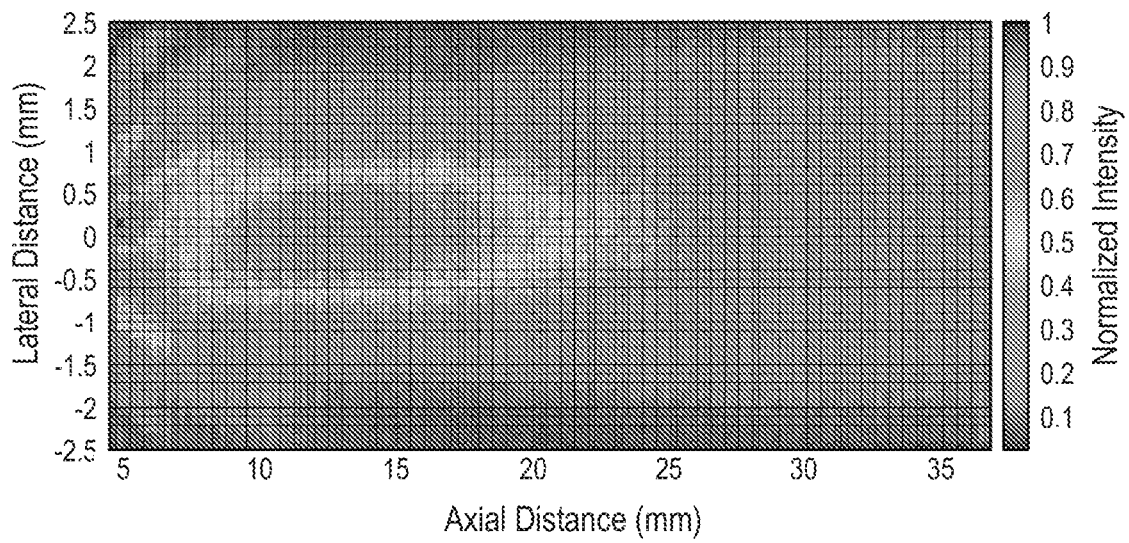
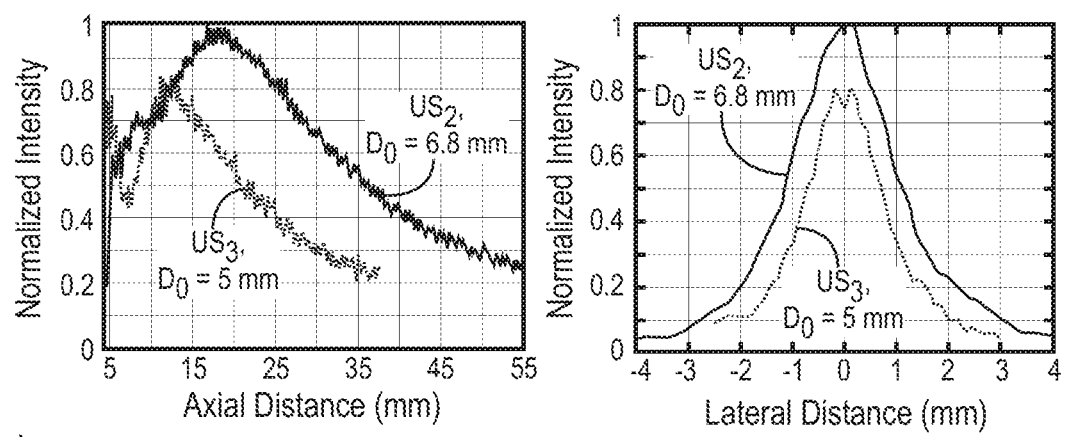
FIG. 18B

FIG. 19
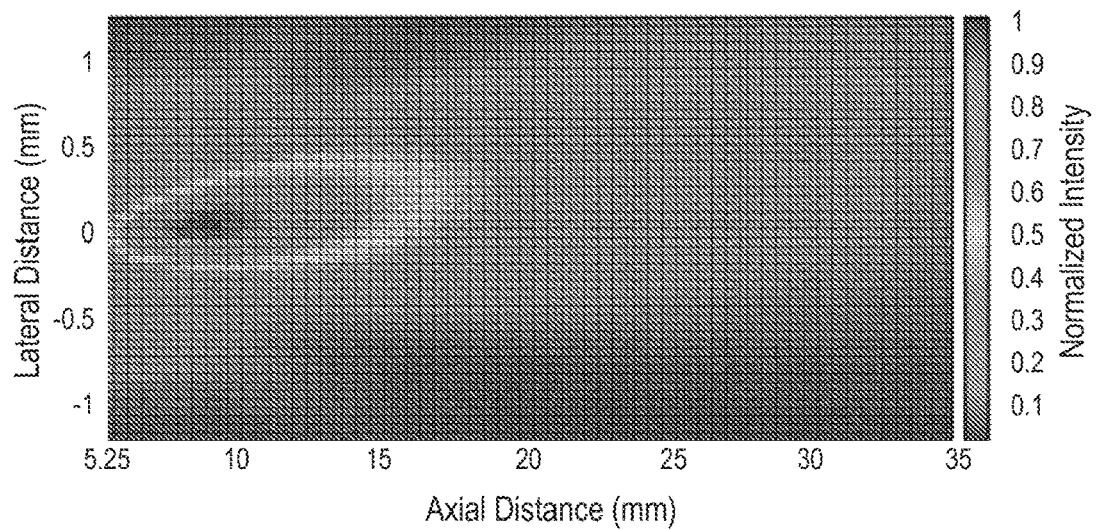
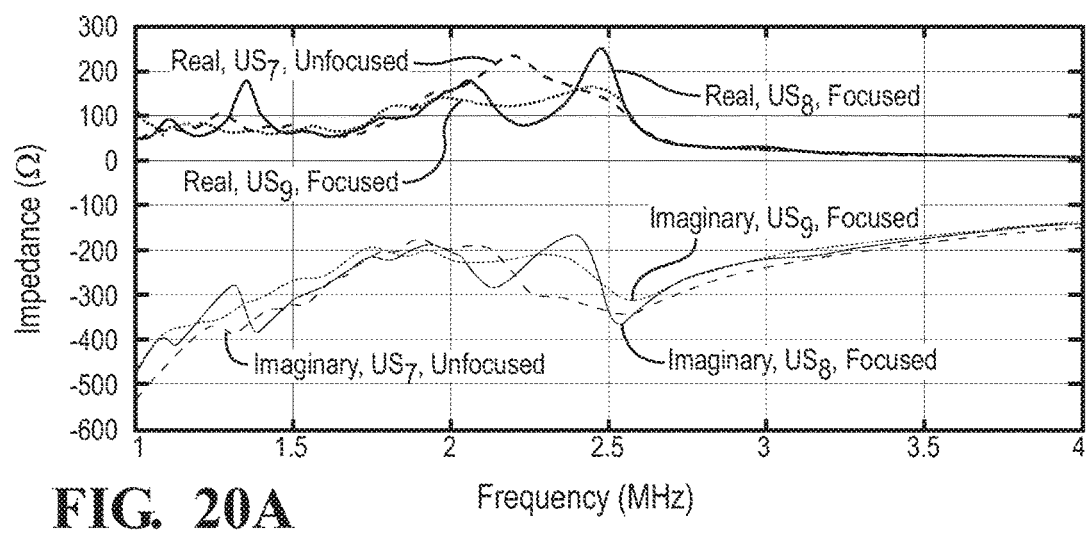
FIG. 20A
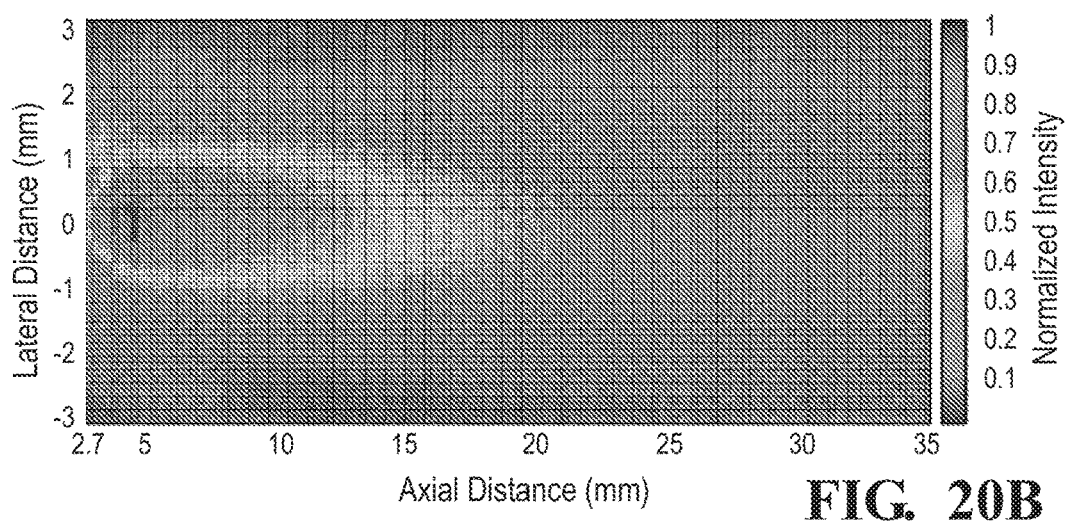
FIG. 20B

FIG. 20C
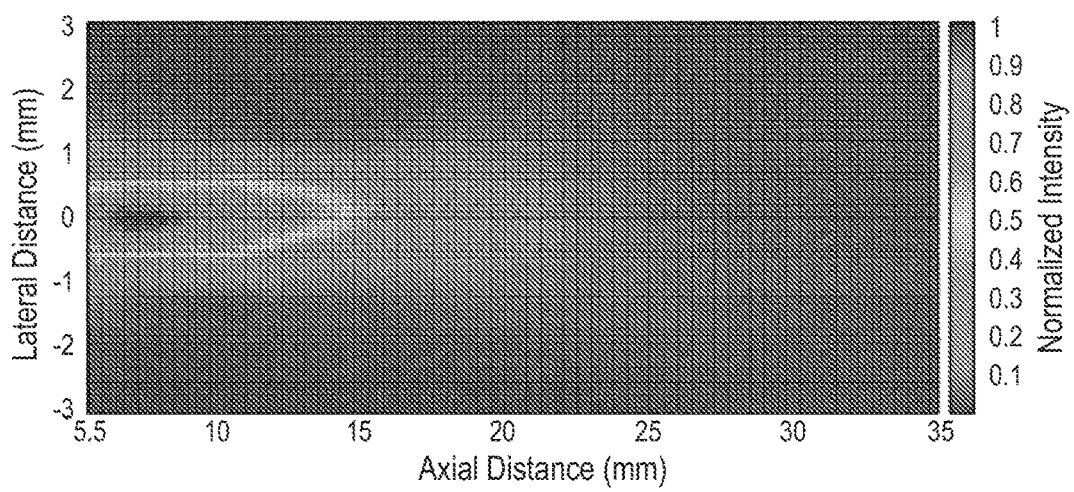
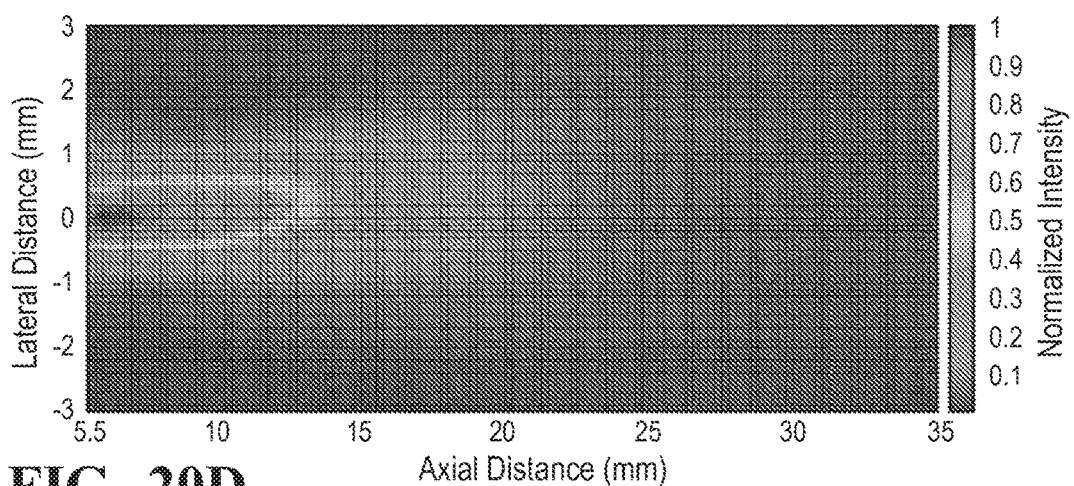
FIG. 20D
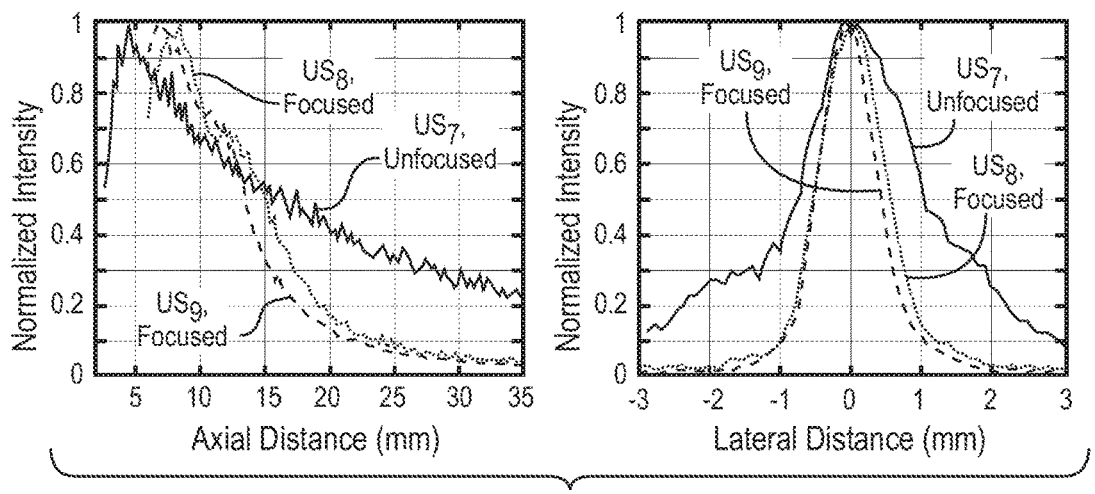
FIG. 20E

FIG. 23A
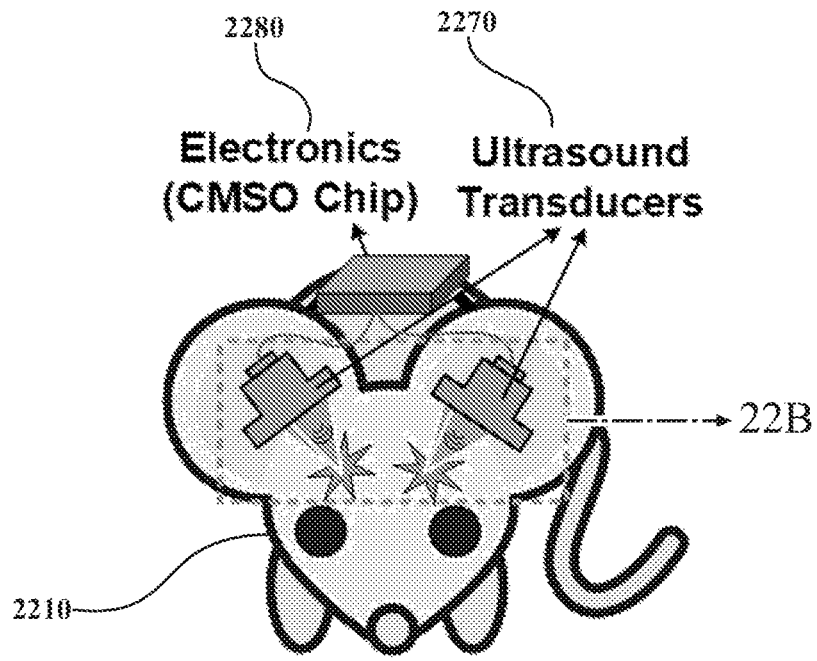
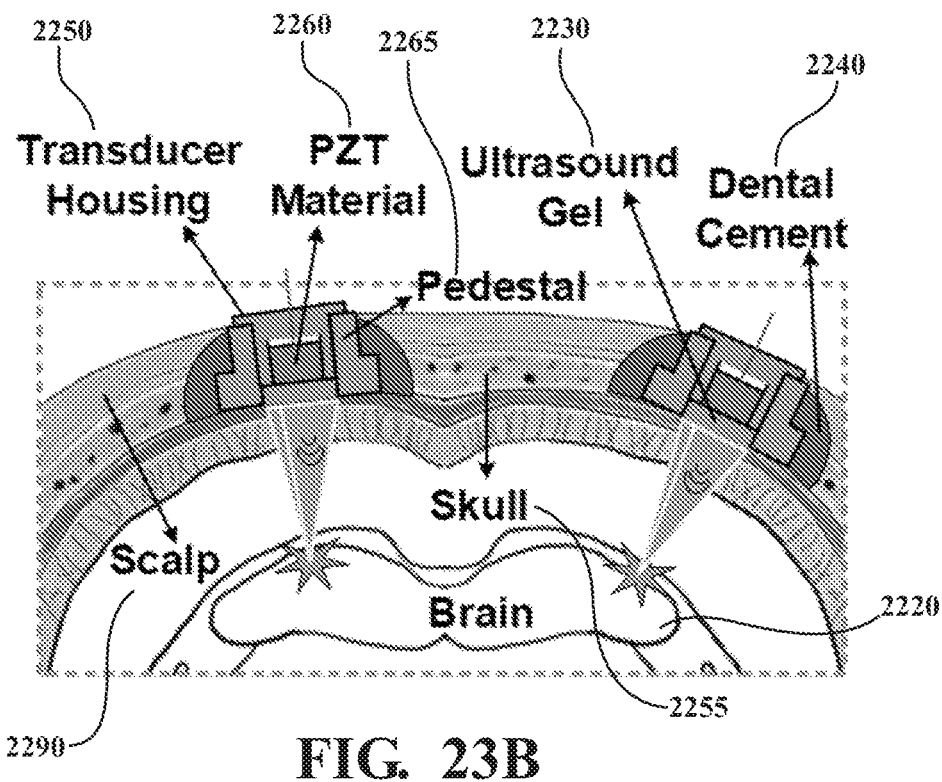
FIG. 23B

IMPLANTABLE DUAL MODE ULTRASONIC DEVICE

CROSS REFERENCE TO RELATED APPLICATION

This application is the U.S. National Stage of PCT/US2019/055763 filed Oct. 11, 2019, which claims priority to U.S. Provisional Patent Application Ser. No. 62/744,367, filed Oct. 11, 2018, the entire content of both are incorporated herein by reference in their entirety.

GOVERNMENT SUPPORT

This invention was made with government support under Grant No. EY029424 awarded by the National Institutes of Health. The Government has certain rights in the invention.

FIELD OF THE INVENTION

The present invention generally relates to field of interacting with biological tissue using minimally invasive devices, and more particularly using high-resolution devices for dual-mode ultrasonic neural stimulation and imaging.

BACKGROUND OF THE INVENTION

Real-time interfacing with the brain by monitoring and stimulating brain activity at large scale with high spatiotemporal resolution has the potential to enhance our perceptual, motor, and cognitive capabilities, as well as to restore sensory and motor functions lost through injuries or diseases [1]. Currently, the therapeutic utility of brain stimulation in managing numerous neurological and psychiatric diseases has been well understood[2]. For example, deep brain stimulation (DBS) ameliorates Parkinson's disease symptoms[3], and multiple pilot studies have begun to examine the utility of DBS for neurological conditions such as dystonia[4], epilepsy[5], depression[6], and obsessive-compulsive disorder[7]. A brain-machine interface (BMI) can restore motor control or create actions from thoughts by monitoring brain activity in severely disabled patients suffering from diseases such as spinal cord injury, major amputations, and stroke. In BMIs, neuromodulation can substitute for conventional visual feedback, and provide a direct sensory feedback from artificial limbs into the brain[8]. By closing the control loop in BMIs with neuromodulation, dramatic performance improvements in executing sophisticated tasks with prosthetic devices can be achieved[9].

In neuroscience research, dynamic mapping of brain circuits by monitoring and modulating brain activity can enhance our understanding of brain functions, and also help researchers to better understand different neurological disorders based on the identification of underlying neural circuits[10]. These brain activities can be monitored either directly by recording electrical signals or indirectly by imaging hemodynamic changes induced by the neurovascular coupling in the vessels surrounding activated neurons[11]. For a neural interface to be an effective research tool, monitoring and modulating brain activity of complex three-dimensional (3D) distributed neural circuits within the entire brain with the high spatiotemporal resolution of several micrometers and milliseconds is often required[12].

Recently, neuromodulation of the peripheral nervous system (PNS) has also received great attention for its potential to replace prevalent pharmacological approaches with implantable electroceuticals[13]. This offers a new class of revolutionary treatments known as bioelectronic medicines that require modulation of neural signaling patterns in visceral organs, such as the lungs, heart, liver, pancreas, kidneys, bladder, gastrointestinal tract, and lymphoid and reproductive organs at the level of nerve fibers with diameters of ~100 μm and below[14]. Some examples include vagus nerve stimulation for the treatment of epilepsy, inflammatory bowel disease, rheumatoid arthritis, and diabetes, as well as bladder and gastric stimulation[15]-[18]. Furthermore, the PNS stimulation can also provide sensory feedback to users of prosthetic devices[19].

Neuromodulation can be achieved with different modalities from pharmacological and chemical methods, which lack specificity and have numerous metabolic requirements, to electrical, electromagnetic, optical, and acoustic methods that have higher specificity. Noninvasive tools, such as transcranial magnetic stimulation (FIG. 1A) and transcranial direct/alternating-current stimulation (FIG. 1B), suffer from poor spatial resolution (cm and above)[20]-[22], while invasive methods such as electrical (e.g. deep brain stimulation, DBS, in FIG. 1C) and optical (optogenetics in FIG. 1D) stimulation can achieve higher specificity by implanting electrodes and optic-fibers/light-emitting diodes (LEDs) into neural tissues[23]-[25]. Although optogenetics currently offers unrivaled spatial resolution down to the cellular level, it requires genetic alteration that is risky, if not impossible, in humans. In addition, for current or light delivery, both electrical and optical stimulation requires penetration into the parenchyma of the nervous system that causes scar tissue formation and long-term damage (highly invasive). In the PNS, although cuff or spiral electrodes can deliver stimulation from outside of a nerve, they lack specificity and highly invasive penetrating electrodes are often adopted to stimulate specific fibers inside a nerve[26].

FIG. 2A compares the specifications of current methods for brain-activity monitoring[27]. Although noninvasive methods such as magnetic resonance imaging (MRI), functional MRI, magnetoencephalography (MEG), positron emission tomography (PET), and electroencephalography (EEG) provide whole-brain spatial coverage, they suffer from poor spatiotemporal resolution (sub-cm/sub-s and above). High spatial resolution of 1 mm can be achieved with fMRI at the cost of low (sub-minute) temporal resolution and not being portable. In order to improve temporal resolution to the milliseconds scale, minimally invasive methods such as electrocoticography (ECoG) and micro-electrocoticography (μECOG) record synchronized potentials close to the cortical surface. However, to achieve higher spatiotemporal resolution (micrometers, milliseconds) inside the brain with a portable system, direct action potential recoding with highly invasive penetrating electrodes is the only viable method that unfortunately cause scar tissue formation and long-term damage[28], [29]. FIGS. 7A-7D show different brain stimulation techniques. FIG. 7A shows invasive deep brain stimulation (DBS) with electrical currents and FIG. 7B shows noninvasive transcranial direct current stimulation (tDCS). FIGS. 7C and 7D show transcranial magnetic stimulation (TMS) and transcranial focused ultrasound (tFUS), respectively.

Ultrasound for Neuromodulation and Hemodynamic Imaging

Low-intensity transcranial focused ultrasound (tFUS) as a noninvasive (external source) neuromodulation modality for both activation and suppression of neural activity in the central nervous system (CNS) and PNS has recently gained more attention due to its higher spatial resolution of sub-cm scale relative to its noninvasive counterparts. Noninvasive use of low-frequency (0.25-0.65 MHz), pulsed, focused ultrasound for exciting neuronal circuits and motor responses in mouse brains, disrupting electrographic seizure activity in intact mouse brains, stimulating peripheral somatosensory circuits in humans, and modulating the activity of the primary somatosensory cortex in humans has already been shown P[30]-[35]. Recently, successful noninvasive ultrasonic stimulation in mice, rats, cats, rabbits, sheep, monkeys, and humans with different acoustic frequencies within the 0.2-43 MHz range have also been shown (FIG. 3A)[36][4][52]. FIG. 3A shows setups for noninvasive ultrasonic neuromodulation on anesthetized/constrained animals and on humans through the skull.

Ultrasound has also been advocated for noninvasive brain activity imaging in small animals with thin skulls due to its higher spatiotemporal resolution of 100 μm and 1 ms in depth relative to its noninvasive counterparts. Functional ultrasound imaging is used for monitoring microvascular hemodynamics in response to brain activation in rodents. Using a 15-MHz ultrasound probe, powerful Doppler images of the whole rat brain (2 cm×2 cm) have been obtained in 320 ms with a resolution of 100 μm (FIG. 3B)[53]. FIG. 3B shows a setup for performing ultrasonic imaging on tethered animals. As discussed above, ultrasound has already been shown to be an effective noninvasive tool for modulating neural activity with a small latency of tens of ms, and for imaging hemodynamic changes in rodents' brains with spatiotemporal resolution of 100 μm and hundreds of ms. Today's technologies for ultrasonic stimulation are noninvasive, as shown in FIG. 3A, and are applied to the brain tissue through the skull. In addition, brain imaging with ultrasound has only been applied on rodents through removed or thinned skulls. There is no implantable ultrasonic technology for high spatiotemporal resolution (micrometers, milliseconds) neuromodulation or imaging on humans, let alone any dual-modal technology that can support both ultrasonic neuromodulation and imaging. Thus, it is desirable to develop a technology to use ultrasound in humans for neuromodulation and imaging with higher spatiotemporal resolution to overcome the limitations of the existing technologies and to provide a better solution.

SUMMARY OF THE INVENTION

Real-time interfacing with the central and peripheral nervous systems (CNS and PNS), such as the brain and nerve bundles in the PNS, by monitoring and stimulating neural activity at large scale with high spatiotemporal resolution (milliseconds, micrometers) has great potentials including but not limited to: 1) enhancing our understanding of the extremely complex nervous system; 2) enhancing our perceptual, motor, and cognitive capabilities; 3) restoring sensory and motor functions lost through injuries or diseases; 4) managing numerous neurological and psychiatric diseases (e.g., Parkinson's disease); and 5) replacing prevalent pharmacological approaches with implantable electroceuticals (known as bioelectronic medicines). Conventional implantable methods for high spatiotemporal resolution neuromodulation or imaging are highly invasive and require penetration of devices into neural tissue, which causes long-term damage. This disclosure outlines a new, minimally invasive, dual-modal implantable technology for both neuromodulation and imaging at high spatiotemporal resolution (milliseconds, micrometers) and at large scale with ultrasound. A wireless implant, equipped with an array of ultrasonic transducers for both the CNS and PNS, is presented that eliminates the need for penetration into the neural tissue by focusing an ultrasonic beam. Notably, the proposed wireless implant for the PNS utilizes ultrasound for neuromodulation, imaging, power delivery, and telemetry. In addition, microscopic ultrasonic (μUS) stimulation and imaging is outlined, in which sub-millimeter sized ultrasonic transducers are implanted into the neural tissue (as opposed to sitting on the surface of the neural tissue) to deliver stimulation locally with high precision and also to image the neural activity of the neural tissues.

Similar to FIG. 2A, FIG. 2B compares key specifications of different neuromodulation approaches in terms of their spatial coverage, spatial resolution and invasiveness. Noninvasive tools, such as transcranial magnetic stimulation (TMS) and transcranial direct and alternating current stimulation (tDCS, tACS), suffer from poor spatial resolution of centimeter (cm) scale and limited depth of penetration [2]. Invasive methods, such as electrical and optical stimulation, can achieve better spatial resolution through the implantation of electrodes and optic-fibers/light-emitting-diodes (LEDs) into neural tissue at the cost of tissue inflammation and damage (highly invasive) [29].

Low-intensity transcranial focused ultrasound (tFUS) as a noninvasive neuromodulation modality for both activation and suppression of neural activity has recently gained more attention due to its improved spatial resolution of sub-cm scale [30]. The tFUS is often practiced at low sonication frequencies ($f_p$, the frequency at which the transducer is driven) of sub-MHz (i.e., poor spatial resolution) due to the large skull attenuation at high frequencies, but successful ultrasound stimulation at $f_p$s up to 43 MHz has also been reported.

The concept of microscopic ultrasound stimulation (μUS) further improves the spatial resolution and coverage of ultrasound stimulation. In μUS, either an electronically phased array of ultrasound transducers or several millimeter (mm)-sized focused transducers can directly be placed on the brain surface with partially removed skull (or over thinned skull) as shown in FIG. 4C or sub-mm-sized transducers can be implanted inside the brain tissue to deliver a focused ultrasound pressure to the neural target.

Unlike tFUS, in which ultrasound travels through the lossy skull medium with different acoustic impedance compared with the soft tissue demanding low frequency operation (poor spatial resolution), in the μUS acoustic energy is steered and delivered directly to the neural target within a more homogenous medium. Therefore, neuromodulation with finer spatial resolution at a larger scale can be achieved with higher energy efficiency, defined as the transducer generated acoustic intensity at the neural target divided by the transducer input electrical power. In μUS, high energy efficiency is key in reducing the required electrical power that could consequently enable the μUS system to be wearable or implantable. Despite all these advantages of the proposed μUS, it is more invasive than tFUS as it requires device implantation. However, μUS is still less invasive compared to its electrical and optical counterparts, because ultrasound transducers in μUS can be placed on the brain surface outside the parenchyma.

A key element in both tFUS and μUS is the ultrasound transducer(s) that converts input electrical power into acoustic pressure. The transducer design can highly affect the stimulation specifications such as spatial resolution and energy efficiency. Most of the prior works have mainly focused on broadband (with low-quality factor, Q) ultrasound transducers with pulse excitation which are frequently used in ultrasound imaging applications. However, the proposed µUS generally requires a sinusoidal excitation (FIG. 4D) as well as high energy efficiency (to be portable) that should be achieved with narrowband ultrasound transducers with high Q.

Until now, most tFUS experiments have only been focused on studying the impact of ultrasound on neural tissue, investigating optimal tFUS sonication parameters and studying interactions between acoustic beams and brain tissues using commercially available bulky ultrasound transducers. Unfortunately there has been no comprehensive study (in a quantitative manner) on the impact of transducer dimension, focusing, acoustic matching, backing materials and frequency on the generated acoustic beam profile that relates to the stimulation spatial resolution and energy efficiency.

In this disclosure, the µUS transducer array in FIG. 4C is simplified to a single mm-sized transducer (either focused or with natural focus), made from lead zirconate titanate-5A (PZT-5A). This disclosure discloses a comprehensive quantitative evaluation of the performance of mm-sized ultrasound transducers (in both water and sheep brain phantom medium) in terms of spatial resolution and energy efficiency in the context of ultrasound neuromodulation that could provide designers of such systems with insight in developing novel electronics and in vivo experiments. This disclosure introduces a new figure-of-merit (FoM) for µUS as the maximum acoustic intensity to input-power (at electrical port) ratio ($I^2PR$) related to the energy efficiency.

A method of neural stimulation and imaging of nervous system of a subject according to this disclosure includes the steps of providing an interface device operable to generate an ultrasonic beam for neuromodulation and imaging of a targeted neural structure of a subject; implanting the interface device in the subject; and providing and disposing an external coil array over the targeted neural structure of the subject, wherein the external coil array is wirelessly powering and communicating with the interface device. Another method further includes the steps of providing the interface device comprising at least one ultrasonic transducer operable to focus an ultrasonic beam on the targeted neural structure of the brain of the subject for neuromodulation and imaging of the targeted neural structure, and/or comprising at least one sub-millimeter sized ultrasonic transducer operable to generate an ultrasonic point-source near a targeted neural structure of the brain of the subject for microscopic ultrasound neuromodulation and imaging of the targeted neural structure; implanting the at least one ultrasonic transducer in a subdural region located over a brain surface and/or the at least one sub-millimeter sized ultrasonic transducer inside a neural tissue of the brain of the subject; and providing and disposing an external coil array over a skull of the subject, wherein the external coil array is wirelessly powering and communicating with the interface device using an inductive link.

An alternate method further includes the steps of providing the interface device comprising at least one ultrasonic transducer operable to focus an ultrasonic beam on a targeted neural structure of a peripheral nervous system (PNS) of the subject for neuromodulation and imaging of the targeted neural structure, and/or comprising at least one sub-millimeter sized ultrasonic transducer operable to generate an ultrasonic point-source near a targeted neural structure of peripheral nervous system (PNS) of the subject for microscopic ultrasound neuromodulation and imaging of the targeted neural structure; implanting the at least one ultrasonic transducer over a nerve bundle of the PNS without any penetration into a parenchyma of the PNS, and/or the at least one sub-millimeter sized ultrasonic transducer in a nerve bundle of the PNS of the subject; and providing and disposing an external coil or ultrasonic transducer array over the skin of the subject that is covering the implanted interface device, wherein the external coil or ultrasonic transducer array is wirelessly powering and communicating with the interface device using an inductive or ultrasonic link.

An implantable neural stimulation and imaging system for a central nervous system (CNS) of a subject according to this disclosure may comprise an interface device configured to be implanted in a subdural region located over a brain surface, the interface device comprising at least one ultrasonic transducer operable to focus an ultrasonic beam on a targeted neural structure of the brain for neuromodulation and imaging of the targeted neural structure; and an external coil array disposed over a skull of the subject, the external coil array configured to wirelessly power and communicate with the interface device using an inductive link.

Another implantable neural stimulation and imaging system for a peripheral nervous system (PNS) of a subject according to this disclosure may comprise an interface device configured to be implanted over a nerve bundle of the PNS without any penetration into a parenchyma of the PNS, the interface device comprising at least one ultrasonic transducer operable to focus an ultrasonic beam on a targeted neural structure of the PNS for neuromodulation and imaging of the targeted neural structure; and an external coil or ultrasonic transducer array disposed over the skin of the subject that is covering the implanted interface device, the external coil or ultrasonic transducer array configured to wirelessly power and communicate with the interface device using an inductive or ultrasonic link.

An implantable neural stimulation and imaging system for central nervous system (CNS) of a subject according to this disclosure may comprise an interface device configured to be implanted inside a neural tissue of a brain of the subject, the interface device comprising at least one sub-millimeter sized ultrasonic transducer operable to generate an ultrasonic point-source near a targeted neural structure of the brain for microscopic ultrasound neuromodulation and imaging of the targeted neural structure; and an external coil array disposed over a skull of the subject, the external coil array configured to wirelessly power and communicate with the interface device using an inductive link.

Another implantable neural stimulation and imaging system for peripheral nervous system (PNS) of a subject according to this disclosure comprises an interface device configured to be implanted in a nerve bundle of the PNS of the subject, the interface device comprising at least one sub-millimeter sized ultrasonic transducer operable to generate an ultrasonic point-source near a targeted neural structure of the PNS for microscopic ultrasound neuromodulation and imaging of the targeted neural structure; and an external coil or ultrasonic transducer array disposed over the skin of the subject close to the interface device, the external coil or ultrasonic transducer array configured to wirelessly power and communicate with the interface device using an inductive or ultrasonic link.

In some embodiments, the interface device is driven at a high frequency (1-40 MHz range) with a continuous, pulsed or sinusoidal carrier waveform, the carrier waveform being amplitude-modulated with a lower frequency (e.g. in a KHz range) or being reconstructed with a train of sharp pulses with varying amplitudes. The pulsed carrier waveform may have a variable number of cycles, pulse repetition frequency and/or duration. The non-invasive embodiment may have the at least one ultrasonic transducer having a maximum thickness of 0.5 mm. These embodiments may have the interface device comprising at least two ultrasonic transducers that are disposed in either stacked or side-by-side manner. The ultrasonic link in some embodiments is based on a ultrasonic harmonic modulation (UHM) technique.

In some embodiments, the at least one ultrasonic transducer comprises piezoelectric materials (e.g. lead zirconate titanate, PZT). The at least one transducer in other embodiments is operable to focus the ultrasonic beam having a frequency in a range of 1 MHz to 40 MHz, While in other embodiments, the at least one transducer has a focal length in a range of 1 mm to 50 mm, in alternate embodiments, the at least one sub-millimeter sized ultrasonic transducer is operable to generate the ultrasonic point-source having a frequency in a range of 0.5 MHz to 10 MHz. In yet other embodiments, the at least one sub-millimeter sized ultrasonic transducer has a focal length in a range of 0.1 mm to 1 mm The interface device may comprise an array of the at least one ultrasonic transducers to focus on the targeted neural structure. In some embodiments, the interface device may comprise an array of the at least one sub-millimeter sized ultrasonic transducers to focus on the targeted neural structure.

Some embodiments of the implantable neural stimulation and imaging system may further comprise another interface device configured to be implanted inside the neural tissue of the brain of the subject, the interface device comprising at least one sub-millimeter sized ultrasonic transducer operable to generate an ultrasonic point-source near a targeted neural structure of the brain for microscopic ultrasound neuromodulation and imaging of the targeted neural structure; and the external coil array configured to wirelessly power and communicate with the another interface device using the inductive link.

Yet other embodiments of the implantable neural stimulation and imaging system may further comprise another interface device configured to be implanted in the nerve bundle of the PNS of the subject, the interface device comprising at least one sub-millimeter sized ultrasonic transducer operable to generate an ultrasonic point-source near a targeted neural structure of the PNS for microscopic ultrasound neuromodulation and imaging of the targeted neural structure; and the external coil or ultrasonic transducer array configured to wirelessly power and communicate with the another interface device using an inductive or ultrasonic link.

BRIEF DESCRIPTION OF THE DRAWINGS

FIGS. 2A-2B are charts comparing current methods for brain activity monitoring;

FIGS. 7A-7D are images showing different brain stimulation techniques;

FIG. 8 is conceptual diagram of proposed trasnducers implanted over/inside the brain tissue;

FIGS. 9A-9B are simplified acoustic beam profiles of an disc-shaped ultrasound transducer;

FIGS. 10A-10C are images of simulated acoustic intensity profiles of a transducer;

FIGS. 13A-13B are graphs showing simulated normalized intensity of a transducer;

FIGS. 14A-14D are graphs and images of a beam profile showing a comparison between measured and simulated characteristics of a transducer;

FIGS. 15A-15C are graphs and images of a measured beam profile;

FIGS. 16A-16C are graphs and images showing an impact of a backing layer on the acoustic beam profile;

FIGS. 18A-18B are graphs and images showing an impact of $D_0$ on the acoustic beam profile;

FIG. 19 shows a measured acoustic beam profile for another transducer;

FIGS. 20A-20E are graphs and images showing an impact of beam focusing and acoustic matching;

FIGS. 23A-23B are schematic representations of an embodiment used for testing on rodents.

DETAILED DESCRIPTION OF THE INVENTION

Figure 1A:
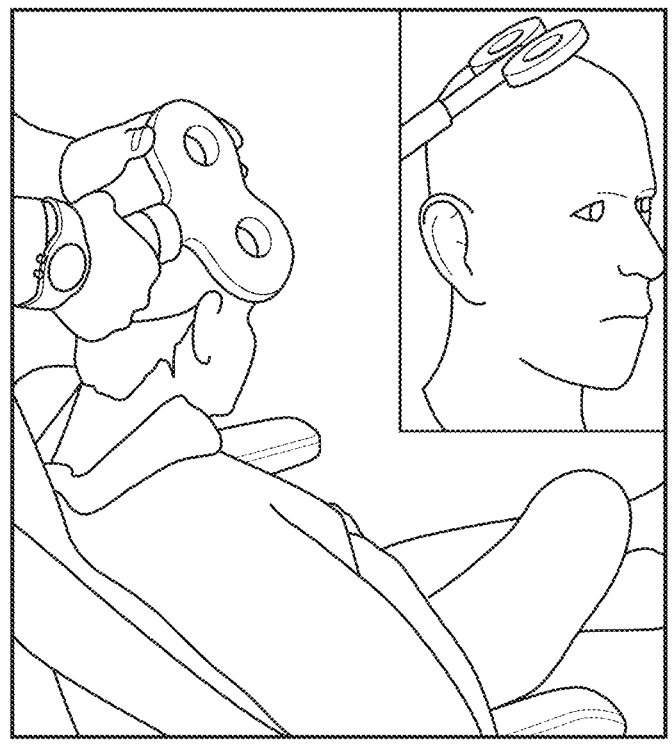
FIGS. 1A-1D are images showing examples of current neuromodulation technologies.
Figure 1B:
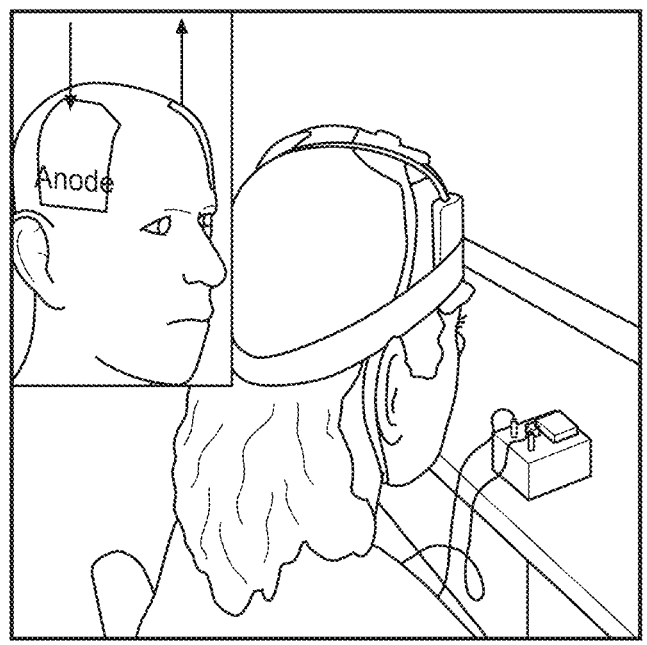
Figure 1C:
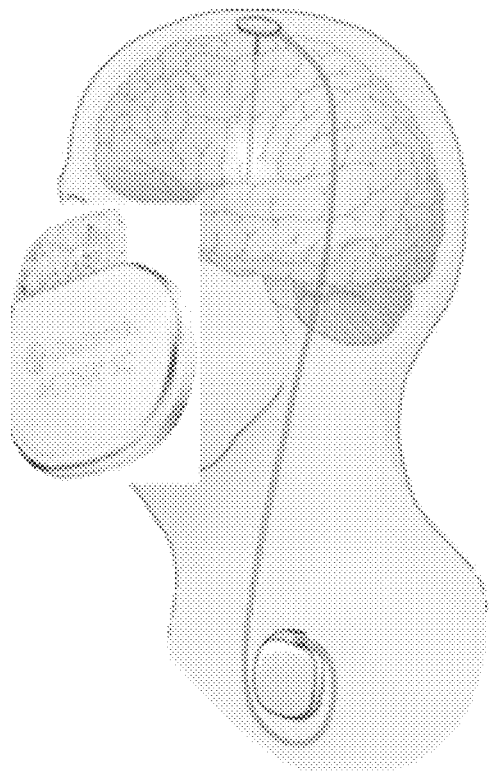
Figure 1D:
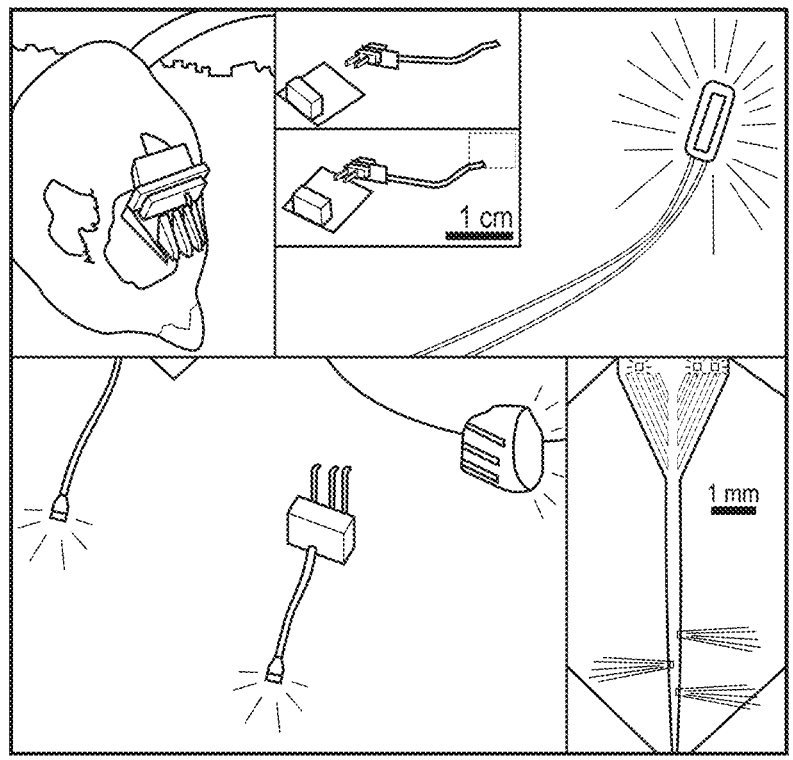
Figure 3A:
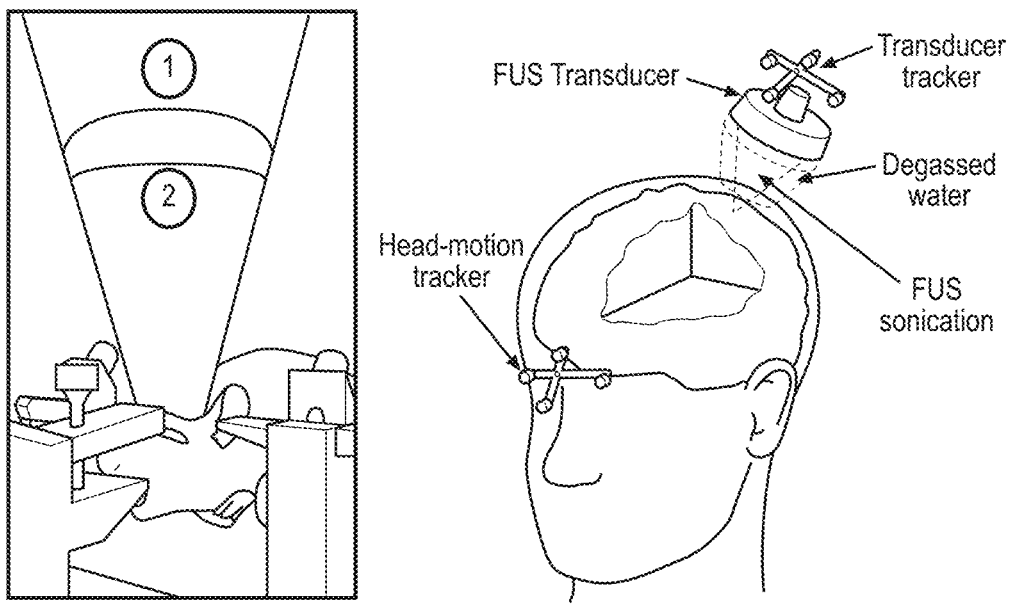
FIG. 3A is an image of a current setup for noninvasive ultrasonic neuromodulation on anesthetized/constrained animals and on a human through the skull.
Figure 3B:
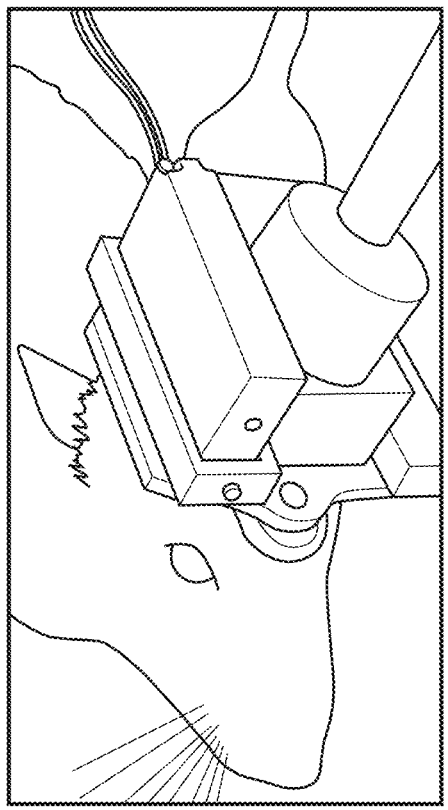
FIG. 3B is an image of a current setup for ultrasonic imaging on tethered animals.
Figures 4A, 4B:
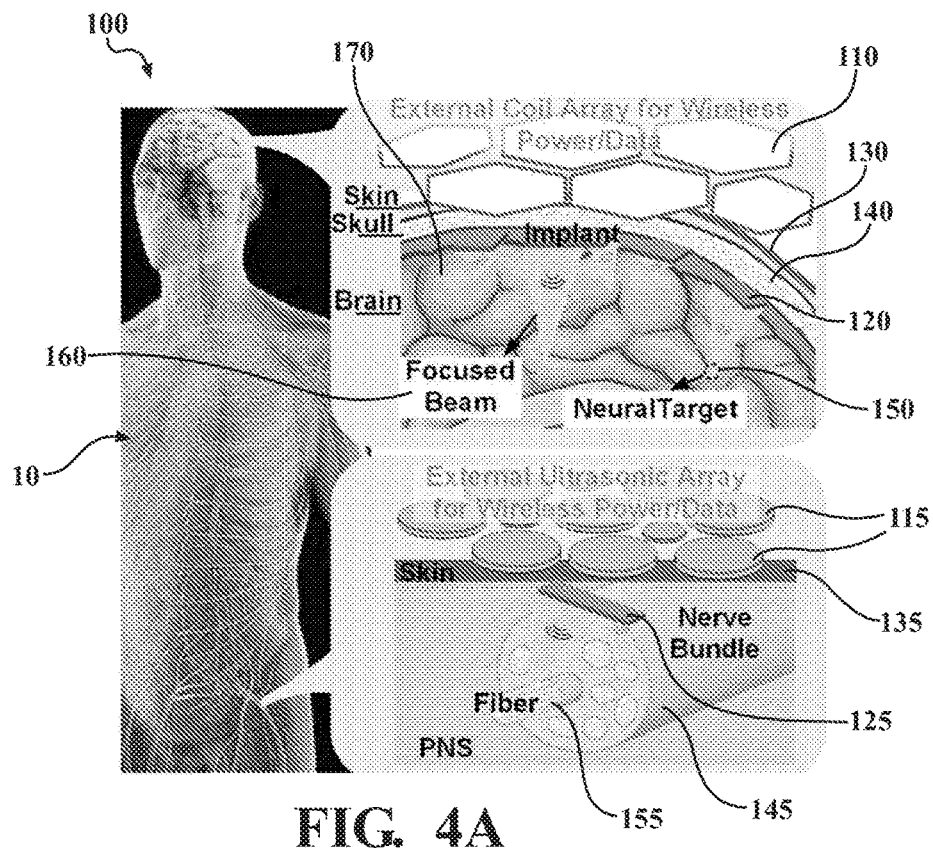
FIGS. 4A-4B are images of a proposed implantable dual-modal technology.

The proposed implantable technology, which can be realized in two ways as shown in FIGS. 4A and 4B, may utilize one or an array of ultrasonic transducers in one or multiple implants distributed over the brain/nerve surface or implanted into the brain/nerve tissue for neuromodulation, imaging, or both simultaneously. These minimally invasive implantable ultrasonic transducers in FIG. 4A, for neuromodulation, focus an ultrasonic beam towards the targeted neural tissue(s) using beamforming techniques. In FIG. 4B, the sub-millimeter sized ultrasonic transducers implanted at the vicinity of the neural target(s) act as point sources and generate ultrasound to stimulate the nearby neural tissue locally. These ultrasonic transducers in FIGS. 4A and 4B can be driven with a continuous or pulsed waveform or a sinusoidal carrier at high frequency (several MHz) either amplitude-modulated with a lower frequency of hundreds of kHz, or reconstructed with a train of sharp pulses with varying amplitudes. In pulse-based sonication, the number of cycles, pulse repetition frequency, and duration may be variable. In imaging the brain activity, the number of transducers as receiver or transmitter, and number of pulses in each firing, may be variable.

As noted above, certain embodiments of the present invention provide an implantable technology for both the central nervous system (CNS) and peripheral nervous system (PNS), as shown in FIGS. 4A and 4B, that could utilize one or an array of wirelessly powered ultrasonic transducers for dual-modal neuromodulation and neuroimaging with high spatiotemporal resolution (milliseconds, micrometers) at large scale. Proposed implantable technology can be realized in two ways. In FIG. 4A (first method), this technology 100 is minimally invasive, because implants 120 are located over the brain surface 170 (subdural) or a PNS nerve bundle 145 of a subject 10 without penetration into the parenchyma of the nervous system. Wirelessly powered implants, using an inductive link for the brain implants 120 and ultrasonic links for the PNS implants 125, include one or an array of ultrasonic transducers to focus an ultrasonic beam 160 on the targeted neural structure 150. An array of these implants 120/125 may be distributed over the brain 170 or nerves 145 for large-scale neuromodulation and imaging.

Proposed implantable dual-modal technology for both neuromodulation and imaging in both the CNS and PNS as shown in FIG. 4B (second method) is called hereafter microscopic ultrasound (µUS) stimulation and imaging 200. In this method 200, sub-millimeter sized ultrasonic transducers 220 are implanted into the neural tissue 170 (brain or nerve parenchyma) to deliver stimulation locally with high precision and also image the neural activity. Since each sub-millimeter sized ultrasonic transducer 220 acts as a point source, it can stimulate and image neurons in the vicinity of the transducer with high precision. Each implant 220 can include one or an array of ultrasonic transducers. An array of these implants 220/225 may be distributed over the brain 170 or PNS nerves 145/155 for large-scale neuromodulation and imaging.

An external coil array for wireless power/data 110/210 is disposed covering the implants 120/220 over the skin 130 of the skull 140 of the subject 10. Similarly, an external coil array for wireless power/date 115/215 is disposed covering the implants 125/225 over the skin 135 above the nerve bundle/nerve fiber 145/155 of the subject 10.

Figure 5A:
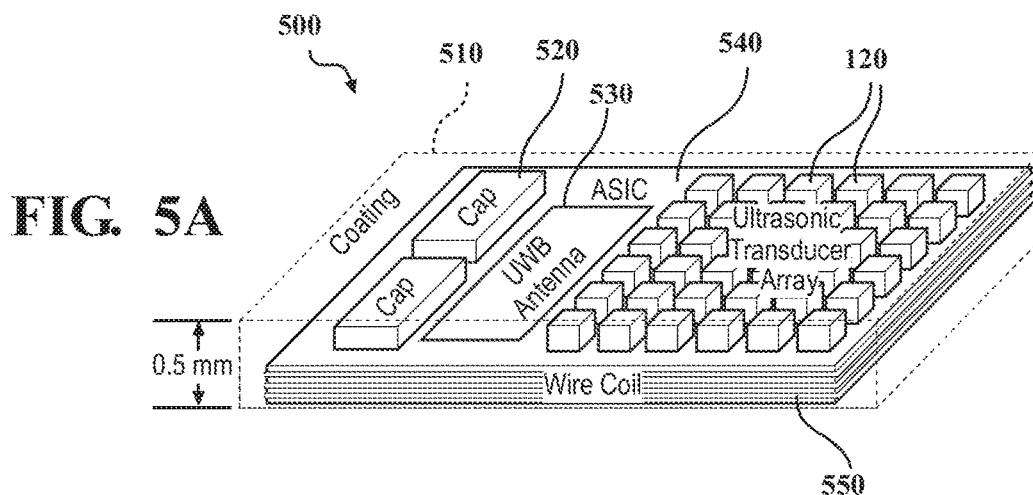
FIGS. 5A-5B are perspective views of an embodiment of a transducer.
Figure 5B:
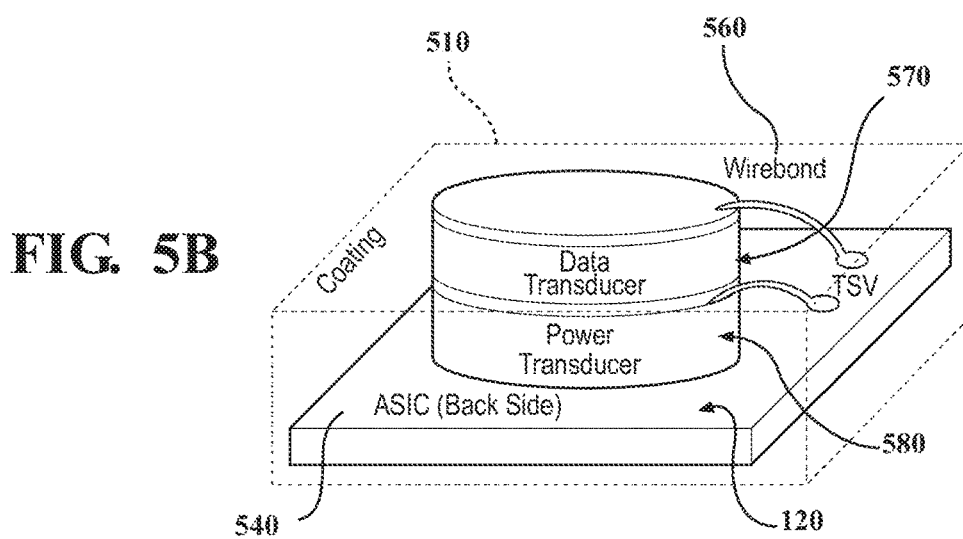

FIGS. 5A and 5B show simplified diagrams for embodiments of the inductively powered brain implants and ultrasonically powered/communicated PNS implants, respectively, with an array of ultrasonic transducers (for method-1 in FIG. 4A). FIG. 5A shows a proposed miniaturized wireless implant (method-1) 500 for brain stimulation and imaging that utilizes inductive power delivery and ultra-wideband (UWB) data communication. The implant 500 is embedded in a coating 510 and comprises capacitors 520, UWB antenna 530 and wire coil 550. FIG. 5B shows a proposed miniaturized wireless implant 120 for stimulating and imaging fibers inside the PNS nerves that also utilize ultrasound for power delivery and data communication, wherein the front size of this implant is the same as that of FIG. 5A with an array of ultrasonic transducers 120. These implants can also have only one transducer for a fixed focus point. The PNS implants use ultrasound for neuromodulation, imaging, power delivery, and data telemetry for the first time. A piezoelectric material is integrated as a 2D array 120 onto an application-specific integrated circuit (ASIC) 540. For the brain implant, a wire-wound coil 530 for power recovery and two off-chip capacitors 520 are added for providing high-voltage regulated supply and resonance (FIG. 5A). The implant may have a maximum thickness of 0.5 mm after biocompatible coating 510. For the PNS implant, two stacked ultrasonic transducers 570/580 for power recovery and data transmission may be integrated on the backside of the ASIC 540 using through-silicon-via (TSV) technology (FIG. 5B). The front side of the ASIC 540 could be similar to that of FIG. 5A. The trasnducers 570/580 are wirebonded 560 with the ASIC 540.

In order to achieve both neuromodulation and imaging within the 3D structure of neural tissue, ultrasonic beamforming with a 2D transducer array is used in this technology (FIG. 4A). In stimulation, the array could only transmit a pre-defined pattern of focused ultrasound to the targeted structure. There are several approaches for transmit and receive beamforming, among which the delay-and-sum is the most simple and computationally inexpensive method at the cost of relatively large side lobes[54]. To attenuate the side lobes, transducer elements may be weighted based on their position (called apodization) by exciting them with different voltage amplitudes[55]. In imaging hemodynamics related to brain activities, the transducer array may operate in both transmit and receive modes, and the choice of beamforming method can impact image contrast, spatiotemporal resolution, spatial coverage, and system complexity (power consumption, data rate, area). Beamforming may be applied in transmit, receive, or both modes by exciting and then sensing from different numbers of transducers using techniques such as Doppler imaging, synthetic aperture, dynamic focusing, linearly constrained minimum variance, and spatial and frequency compounding, with tradeoffs between resolution, contrast, frame rate, spatial coverage, and system complexity[55]. Any beams reflected by the tissues may be received by the transducers. Any beamforming pattern that is fast and provides high-contrast enough to detect blood volume changes in typically 1 s in small blood vessels may be used in this implant.

For µUS stimulation and imaging (FIG. 4B), the sub-millimeter sized ultrasonic transducer is implanted (or an array of them are implanted) within the neural tissue and therefore, they locally deliver ultrasound to the target for both stimulation and imaging. The ASIC 540 in FIGS. 5A and 5B can also be used to control each transducer in µUS stimulation and imaging. Since these transducers could be miniaturized to sub-millimeter scale, there is minimal damage to the neural tissue upon implantation. In addition, they act as point sources and locally stimulate the neurons at their vicinity with high precision.

Figure 5C:
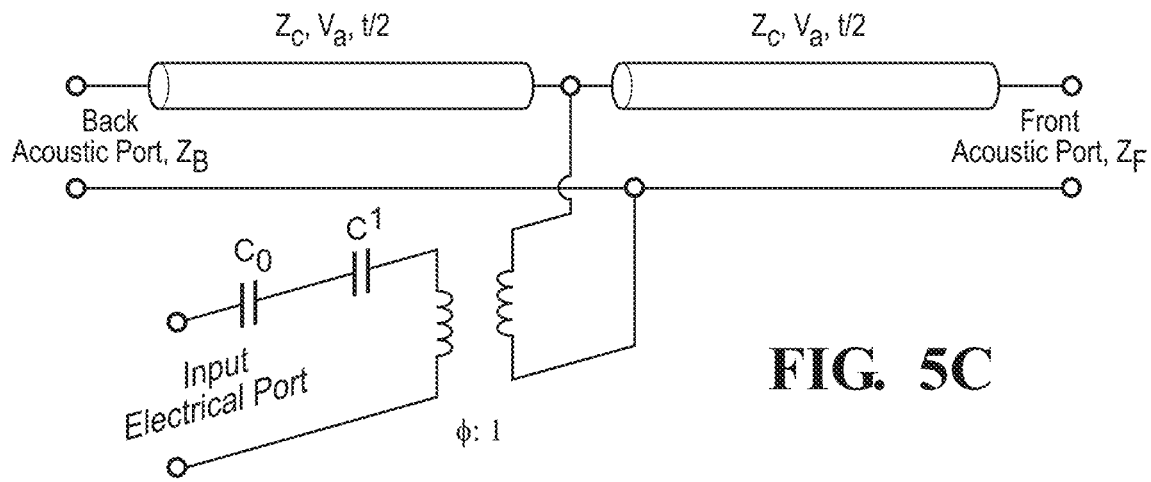
FIG. 5C is a transmission line model of an embodiment of a piezoelectric transducer.

In this disclosure, disc-shaped piezoelectric transducers for µUS are studied, but a similar theory can be generalized to other types of transducers. For a disc-shaped transducer, there are two strongly excited vibration modes, named thickness extensional (TE) and radial or planar expander (PE) modes, as well as several weakly coupled modes near TE and PE modes. For large aspect ratios (Do/t), where Do and t are the outer diameter and thickness of the transducer (piezoelectric material), respectively, the TE mode is dominant, and the transducer only shows a piston-type displacement. FIG. 5C shows the Krimholtz, Leedom, and Matthaei (KLM) model of a piezoelectric transducer, in which the transducer is represented by a transmission line tapped at its center. The transducer is driven through the input electrical port. An ideal transformer with the turn ratio of Φ:1 models the electrical to mechanical coupling where 0 can be found from, $$\Phi = K_T \left( \frac{\pi}{\omega_0 C_0 Z_c} \right)^{1/2} \operatorname{sinc}\left( \frac{\omega}{2\omega_0} \right). \quad (1)$$

$K_T$ and $Z_c$ are the electromechanical coupling factor and acoustic impedance, respectively. $C_0 = \varepsilon_s \times A/t$ represents the transducer clamped capacitance where $\varepsilon^s$ and A are the clamped dielectric constant and the transducer cross-section area. In (1), $\omega_0 = \pi v_a/t$ is called the half-wavelength resonant frequency in the TE mode where $v_a$ is the stiffened acoustic velocity. The KLM model also includes a capacitor in series with the transformer, C' (negligible effect, $C_0 \ll C'$), related to the transducer dimension and $K_T$. Within the transformer secondary side, representing the mechanical part, two generated acoustic waves pass through two transmission lines with t/2 length, $Z_c$ characteristic impedance and $v_a$ sound velocity to reach the front (propagating waves in tissue) and back acoustic ports, interfacing with transducer front and backing materials with $Z_F$ and $Z_B$ acoustic impedances, respectively. When $Z_F$ and $Z_B$ are smaller than $Z_c$, the transmission line has a resonance close to $\omega_0$. The input electrical impedance at $\omega_0$ can be found from, $$R_0 = \frac{4K_T^2}{\pi \omega_0 C_0} \left( \frac{Z_c}{Z_B + Z_F} \right). \quad (2)$$

For the fabrication of transducers discussed below, PZT-5A was chosen as the piezoelectric material due to its high electromechanical coupling, which is key in maximizing acoustic pressure and I²PR. In order to quantitatively study the impact of a wide variety of transducer design parameters, such as the dimension ($D_o$, t), $f_p$, backing material (PCB-backed, air-backed), beam focusing and acoustic matching, nine sets of transducers ($US_1$-$US_9$) were fabricated (specifications summarized in Table I below) at frequencies of 2.2-9.56 MHz.

Figure 5D:
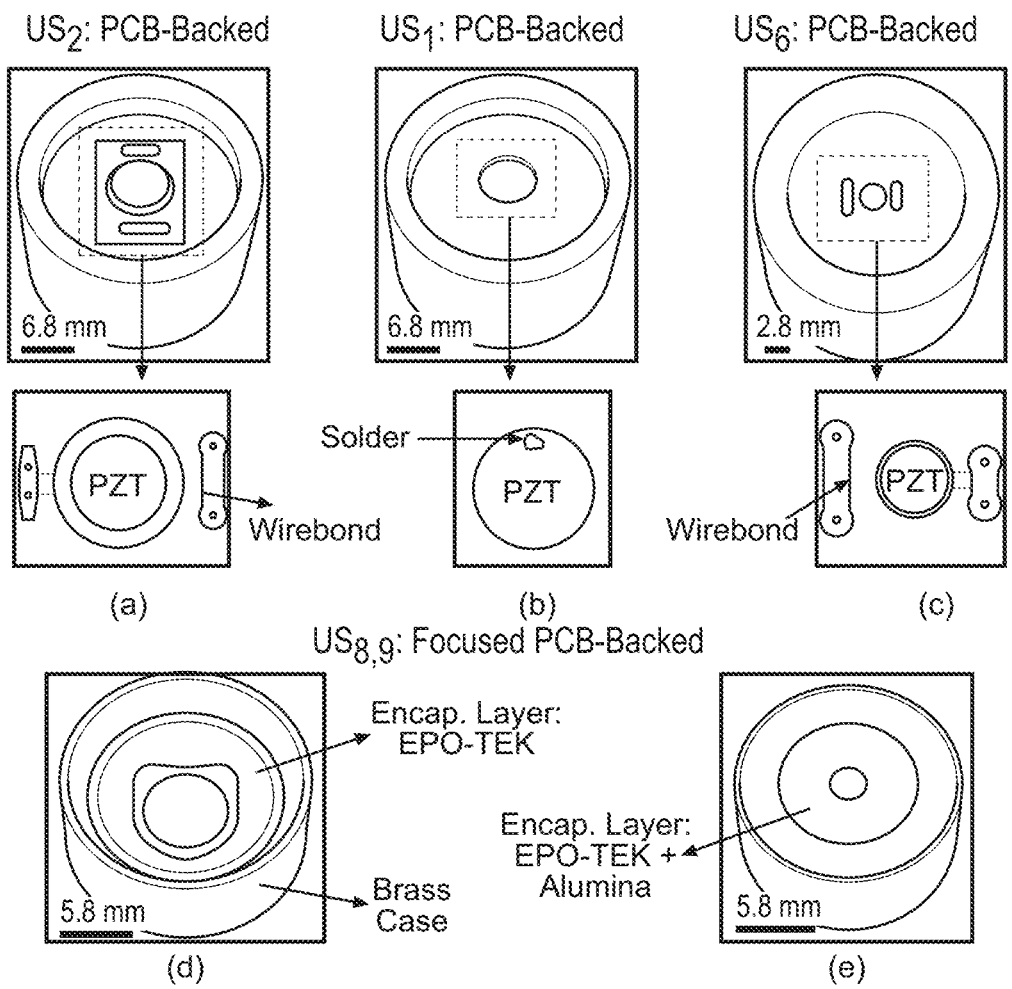
FIG. 5D are images of fabricated transducers according to an embodiment of this disclosure.

FIG. 5D shows some examples of the fabricated transducers mounted within their assemblies. FIG. 5D(a)(c) shows $US_2$ and $US_6$ transducers with PCB as the backing material and piezoelectric (PZT) material dimension of $D_o$=6.8 mm, t=0.75 mm and $D_o$=2.8 mm, t=0.3 mm, respectively. The PZT discs were mounted on a 1.5 mm thick PCB using conductive epoxy, and their top silver plate was wirebonded to a PCB pad. The transducers were connected to SMA connectors using a pair of AWG28 wires. Then, their PCBs were placed inside a custom-made 3D-printed plastic holder. Finally, to provide electrical isolation and protect wirebonds, the transducer surface was coated by Sylgard-184 (The Dow Chemical Company, Midland, Mich.) which has similar acoustic properties to water (cannot be used for acoustic matching).

FIG. 5D(b) shows the air-backed transducer with the PZT material dimension of $D_o$=6.8 mm and t=0.75 mm ($US_1$). The PZT disc top and bottom plates were soldered to a pair of AWG28 wires, and then connected to a SMA connector. A 3D-printed plastic holder with a 6.8 mm diameter hole at its center was fabricated to house the transducer and provide air as the backing material. The PZT disc was placed inside the hole and held still by gluing its perimeter to the holder. The other end of the hole was covered by epoxy to create electrical isolation, thus providing air as the PZT backing material. Similarly, the transducer surface was covered by Sylgard-184. The transducers in FIG. 5D(a) to 5D(c) are unfocused but feature a natural focal zone as shown in FIG. 9B.

FIGS. 5D(d) and 5D€ shows fabricated focused transducers ($US_8$, $US_9$) with a PZT dimension of $D_o$=5.8 mm and t=1 mm and focusing lens materials of EPOTEK-301 (Epoxy Tech., Billerica, Mass.) and EPOTEK-301+Alumina ($Al_2O_3$), respectively (these materials also provide acoustic matching). The procedure to fabricate these two transducers is as follows. 1) The PZT disc was mounted on a PCB using conductive epoxy. 2) The PCB was placed inside a brass housing to hold the lens material. 3) A steel bearing ball with a 10 mm diameter was used as a mold to shape the lens surface (create desired curvature). The bearing ball was held by a 3-axis translation stage (NRT-100, Thorlabs, Newton, N.J.) in a way that the distance between the PZT disc surface at its center and the ball surface was ~λ/4=0.25 mm (λ: ultrasound wavelength inside the lens, $f_p$=2.47 MHz) to provide acoustic matching. And finally, 4) The lens material was poured inside the brass housing to fill the space between the PZT disc and the bearing ball. Before pouring the lens material, the ball was sprayed with a mold release agent (Ease Release 200, Mann Formulated Prods., Gillete, N.J.), facilitating the ball removal from the transducer when the lens material is cured.

Figure 5E:
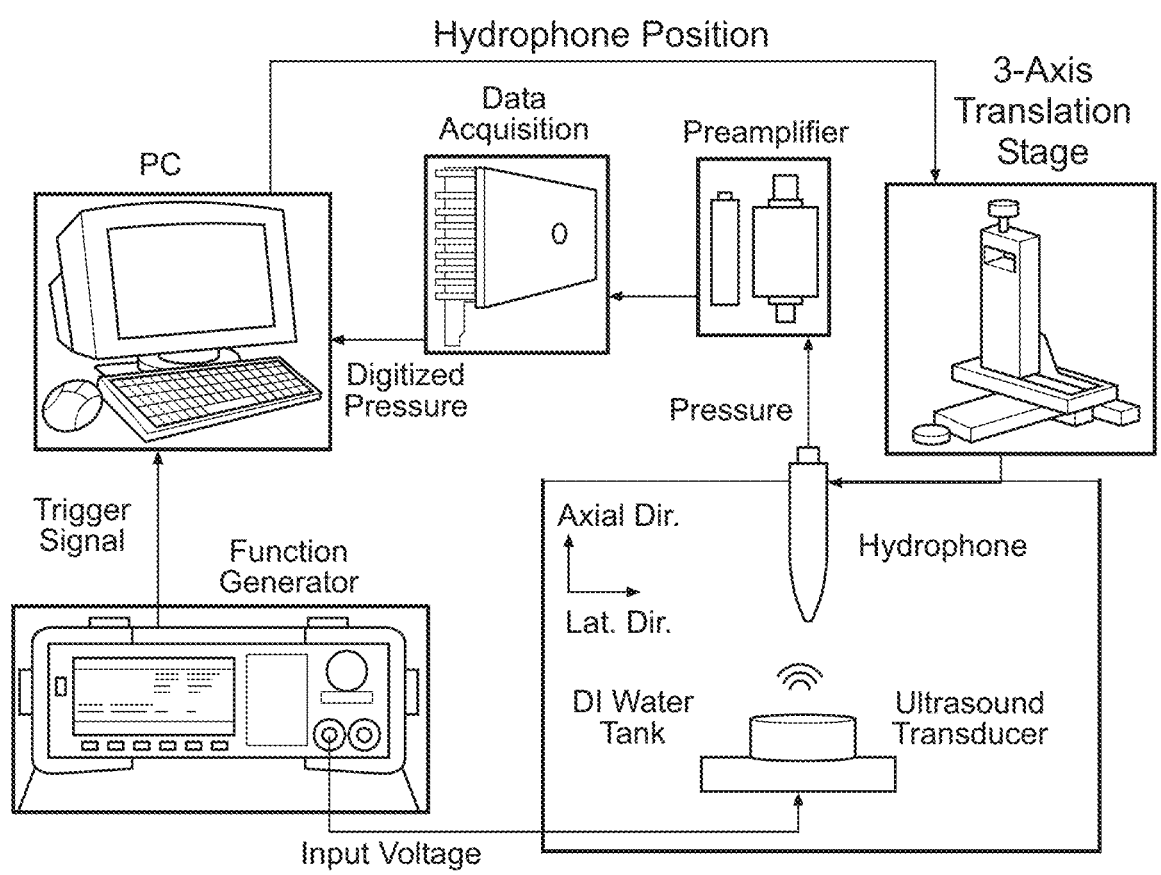
FIG. 5E is an image of a measurement setup used to measure the acoustic pressure generated by an ultrasound transducer.

FIG. 5E shows our setup for measuring the acoustic pressure generated by each transducer. The transducers were placed inside a tank filled with deionized (DI) water and were driven by a function generator with a burst-mode sinusoidal waveform at a pulse repetition interval of 1 ms. All our measurements were done in DI water to ensure that transducer wires are electrically isolated. Since our goal was to study the acoustic intensity profile of each transducer, they were driven by relatively low ultrasound pressure (tens of kPa), which resulted in no ultrasound scattering. However, in experiments with much higher ultrasound pressure (hundreds of kPa), degassed water may be used to avoid ultrasound scattering due to bubbles and cavitation. To measure the acoustic pressure, the HGL0085 hydrophone (Onda, Sunnyvale, Calif.) with 85 μm aperture size and 0.25-40 MHz bandwidth was employed. The voltage across the hydrophone was amplified by a preamplifier with 20 dB voltage gain and 360 $\mu V_{rms}$ input noise. The preamplifier output was captured using a commercial data acquisition system (Razormax 16, GaGe, Lockport, Ill.) with a 1 Gsps sampling rate and 16 bits of resolution. The measured pressure data was stored in a PC.

To locate the measured pressure with the hydrophone position, a trigger signal from the function generator was used. The trigger signal was generated 2 μs before each burst of the input sinusoid. After each 64 consecutive rising edge of the trigger signal (64 ms), the PC sent a command to the 3-axis translation stage to move the hydrophone position with the minimum step size of 50 μm. The stored pressure data was averaged during 64 ms for filtering the high frequency noise.

Figure 5F:
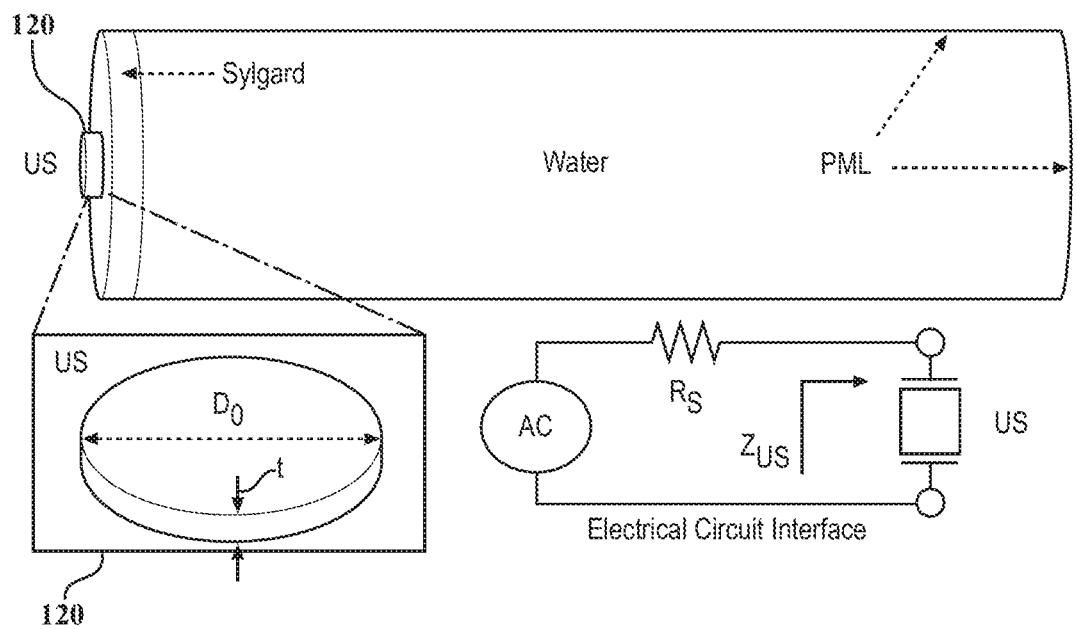
FIG. 5F is a schematic of a simulation setup in COMSOL used to find electrical and acoustic characteristics of the ultrasound transducers.

FIG. 5F shows our COMSOL Multiphysics (COMSOL, Burlington, Mass.) simulation setup used to find the electrical and acoustic characteristic of the ultrasound transducers (US) 120. The transducer front side was covered by Sylgard and was immersed in water with the attenuation coefficient of 0.002 dB/(MHz·cm). The boundaries were modeled with the perfect matching layer (PML). The predefined PZT-5A model in COMSOL was used. The mechanical loss was modeled with the PZT damping factor of 0.02. The Sylgard density and the speed of sound in Sylgard were considered 1500 kg/m³ and 1000 m/s, respectively. The Sylgard thickness was within 1-2 mm for different transducers. In practice, the encapsulation layer thickness should be ~λ/4 to maximize the acoustic intensity. But, the Sylgard acoustic impedance is close to that of water, and therefore, its thickness is not an issue. For simplicity, the 3D-printed holder was not modeled in our simulations. In the electrical circuit interface, an AC voltage source and a source resistor ($R_s$) of 50Ω were connected to the transducer to measure the driving electrical power and impedance ($Z_{US}$), as shown in FIG. 5F.

Figure 5G:
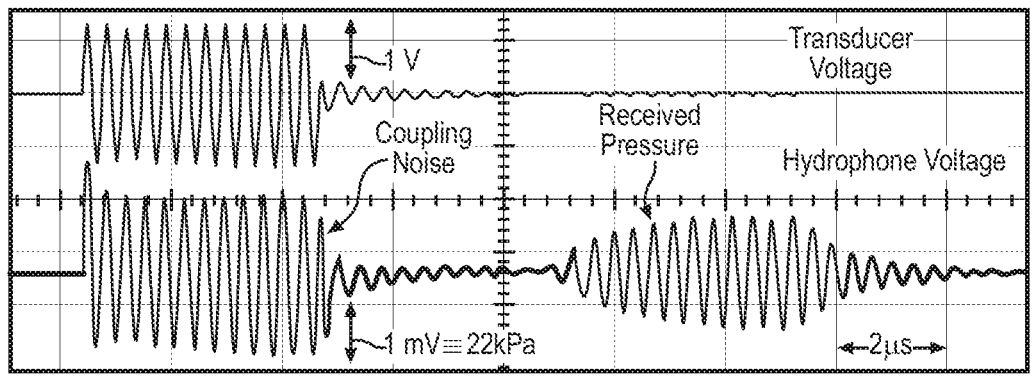
FIGS. 5G-5H are graphs showing measured transient voltage.
Figure 5H:
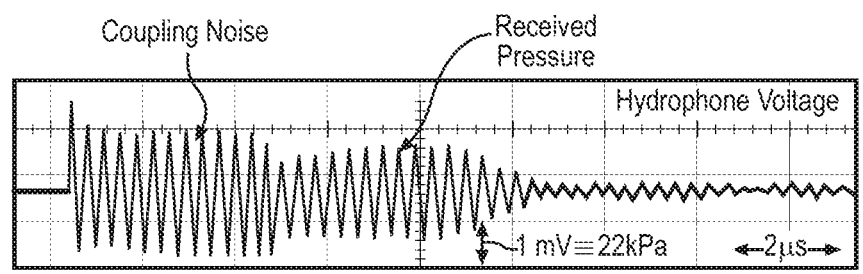

FIGS. 5G and 5H show the measured hydrophone transient voltage (after preamplifier) when $US_2$ was placed at the axial distance of 12.3 mm and 6.9 mm, respectively. The transducer center is considered as the reference point for both axial and lateral distances. The transducer was excited with a burst-mode sinusoid at 2.7 MHz with 12 number of cycles ($N_c$). As shown in FIG. 5G, two different sets of sinusoidal signals can be seen at the hydrophone output. The first set, which coincides with the transducer exciting voltage, was due to the electromagnetic coupling noise between the transducer and the hydrophone. The second set was the actual generated pressure by the transducer.

Since it takes several cycles for the transducer to reach steady-state vibrations due to its limited bandwidth, $N_c$ should be chosen large enough for the hydrophone voltage to settle down. As the hydrophone was closer to the transducer (axial distance of 6.9 mm) in FIG. 5H, the coupling noise interfered with the actual generated pressure. For smaller axial distances, the coupling can completely disrupt the actual received pressure waveform. Therefore, measurements in near-field (small axial distances) is quite challenging. To mitigate this, we chose $N_c$ as the smallest number of cycles that the transducer vibration could reach its steady state. For example, $N_c$ was 10 and 7 for $US_1$ and $US_3$, respectively. The axial distances of 6.9 mm and 12.9 mm were primarily chosen to show the coupling noise interference in measuring acoustic intensity at short distances (<6.9 mm). For neuroscience research applications, these axial distances are optimal for targeting the brain regions of rodents which are within ~10 mm of their skull.

Figure 4C:
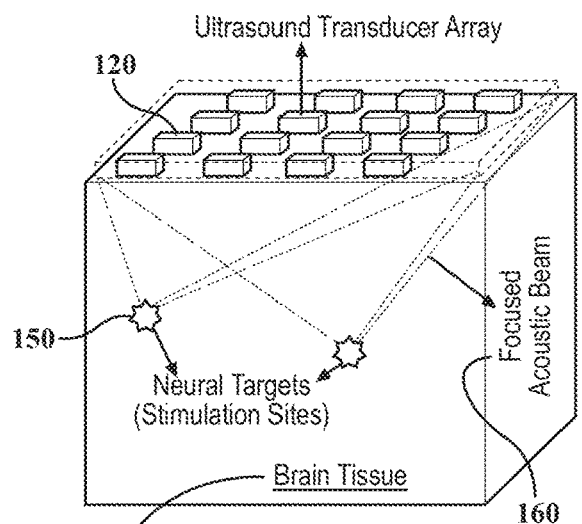
FIG. 4C is a conceptual schematic of an embodiment of a microscopic ultrasound stimulation system.

Based on (3), reducing $D_o$ decreases the focal length and improves the lateral resolution. We investigated the acoustic intensity profile of sub-mm-sized transducers (for implantation in brain tissue) using COMSOL. For instance, for a transducer with $D_o$=0.5 mm and t=0.2 mm the focal point was located at the axial distance of <50 μm. The characteristics of such transducers cannot be accurately measured with our current setup due to the coupling noise. Due to difficulty in fabrication, handling, and characterization of sub-mm-sized transducers, as a first step, in this study we investigated the performance of mm-sized transducers to establish FoM for μUS. These results could help design of micron-scale ultrasound transducer arrays for μUS (FIG. 4C).

Figure-of-Merit (FoM) for the Proposed μUS

For successful ultrasound stimulation, the required acoustic intensity at the neural target should be higher than a threshold, which depends on the sonication frequency and pattern. In μUS, in which the stimulation system could be portable, it is crucial to meet such a threshold requirement with minimal electrical power for driving the ultrasound transducer(s). Therefore, we define the maximum acoustic intensity (W/cm²) to the input electrical power (W) ratio, termed as I²PR (cm¹), as the FoM for the μUS. This FoM, which directly relates to the stimulation energy efficiency, is used to compare the performance of different transducers.

It is worth noting that the insertion loss (IL) and transducer electrical-to-mechanical power efficiency ($\eta_T$) are also the parameters which are often used in the literature as a measure of a transducer sensitivity particularly in imaging. The IL is defined as the voltage inverse ratio of the magnitude of an ultrasound sinusoidal burst, which is emitted by the transducer, to the magnitude of the received reflected echo from a highly reflective plane in parallel with the transducer. The IL is often reported in dB (20 $\log_{10}$). Although IL can be considered as a measure of $\eta_T$, it does not explicitly relate to the acoustic intensity as it lacks information about the transducer focusing characteristic. Therefore, both IL and $\eta_T$, while very important, are not the optimal FoM for the μUS compared to I²PR. This said, all these three parameters (IL, $\Theta_T$, I²PR) were measured for each transducer as shown in Table I.

TABLE I

| | $US_1$ | $US_2$ | $US_3$ | $US_4$ | $US_5$ | $US_6$ | $US_7$ | $US_8$ | $US_9$ |
|---|---|---|---|---|---|---|---|---|---|
| | $D_o$ = 6.8 mm | $D_o$ = 5 mm | $D_o$ = 4.2 mm | $D_o$ = 4.2 mm | $D_o$ = 2.8 mm | | $D_o$ = 5.8 mm, t = 1 mm | | |
| | t = 0.75 mm | t = 0.75 mm | t = 0.73 mm | t = 0.4 mm | t = 0.3 mm | | | | |
| Encapsulation Layer | Sylgard | Sylgard | Sylgard | Sylgard | Sylgard | Sylgard | EPO-TEK | EPO-TEK | EPO-TEK + Alumina |
| Backing Layer | Air | PCB | PCB | PCB | PCB | PCB | PCB | PCB | PCB |
| Focused | No | No | No | No | No | No | No | Yes | Yes |
| $f_p$ (MHz) | 2.8 | 2.8 | 2.8 | 3.056 | 5.66 | 9.56 | 2.19 | 2.47 | 2.47 |
| N (mm) | 14.25 | 16.75 | 11.25 | 4.35 | 14 | 9.25 | 4.6 | 8.5 | 7 |
| Axial Resolution (mm) | 14.75 | 19.25 | 12.5 | 7.75 | 23.75 | 6.25 | 12 | 6.5 | 6.5 |
| Lateral Resolution (mm) | 1.9 | 2.2 | 1.75 | 1.1 | 1.1 | 0.5 | 1.8 | 1.05 | 1 |
| Max. I²PR (1/cm²) | 6.6 | 2.4 | 3.4 | 8.85 | 3.71 | 16 | 2.9 | 9.3 | 12.9 |
| Electrical Impedance (Ω) @ $f_p$ | 303 + 7j | 136 − 50.5j | 287 − 158j | 395 − 317j | 148 − 67.2j | 326 − 5j | 233 − 245j | 250 − 363j | 194 − 318j |
| IL (dB) @ $f_p$ | −21.3 | −24.7 | −29.8 | −30.5 | −31.9 | −33.7 | −31.7 | −32.2 | −29.9 |
| $\eta_T$ (%) @ $f_p$ | 36.7 | 16.3 | 15 | 22.6 | 11 | 12 | 17 | 14.5 | 21.7 |

Microscopic Ultrasound Stimulation Concept

In the proposed μUS as shown in FIG. 8, large external transducers in conventional transcranial FUS systems are replaced with miniaturized ultrasound transducers either implanted inside the brain tissue 170 or placed on the brain surface 170 under the skull 130. For stimulating the regions close to the surface of the brain (within several millimeters), mm-sized transducers 120 with a natural focus are placed on the brain surface (above the target region). To stimulate deep brain regions, sub-mm sized transducers 220, mounted on a flexible thin substrate, with a local ultrasound pressure are implanted inside the brain tissue. The following text discusses the effects of the geometry (diameter and thickness) and $f_p$ of disc-shaped piezoelectric transducers on the stimulation zone. However, similar methodologies can be applied to any transducer shape and material.

FIG. 9A shows a simplified acoustic beam profile of an unfocused disc-shaped transducer with outer diameter of $D_o$ and thickness of t. This beam profile can be divided into near-field and far-field regions, at the boundary of which a natural focal zone is formed with relatively narrower beam and larger acoustic pressure. The near-field region begins from the transducer surface and ends at the focus point, at which the beam reaches its minimum width (~$D_o$/2). Also, the focal length (N) is defined as the distance between the transducer surface and the focus point. Finally, the beam diverges in the far-field region, at which the beam width increases with the distance.

For the following discussion, we have chosen lead zirconate titanate (PZT) as the piezoelectric material for ultrasound transducer due to its high electromechanical coupling coefficient, which is key in maximizing pressure intensity. There are two main resonance modes in a disc-shaped piezoelectric transducer, called thickness extensional (TE) and radial or planar expander (PE) modes, as well as several weakly-coupled vibration modes near TE and PE modes [56]. The vibration mode of a PZT transducer is highly dependent on its aspect ratio, defined as $D_o$/t. For a large aspect ratio, TE is dominant and the transducer has only a piston-type displacement with high electrical to mechanical efficiency. However, as the aspect ratio is reduced, thickness vibration becomes weaker and non-uniform due to radial mode vibration and its harmonics, resulting in lower electrical to mechanical efficiency.

The thickness and radial mode resonance frequencies, $f_{tr}$ and $f_{rr}$, respectively, of a PZT transducer with large aspect ratio can be found from, $$f_{tr}=N_T/t, f_{rr}=N_P/D_o, \quad (3)$$

where $N_T$ and $N_P$ are thickness and radial mode frequency constants, respectively. It can be seen that both $f_{tr}$ and $f_{rr}$ are strongly dependent on $D_o$ and t. The focal length (N) also highly depends on the transducer geometry, and can be found for a large aspect ratio from, $$N=(f_p \times D_o^2)/(4 \times v), \quad (4)$$

where $f_p$ and v are the sonication frequency and the sound velocity in the medium, respectively.

Since both (3) and (4) are accurate for a large aspect ratio [56], and the proposed μUS operates with miniaturized transducers, finite-element method (FEM) simulation tools such as COMSOL Multiphysics (COMSOL, Burlington, Mass.) is used to accurately model transducers. Nonetheless, both (3) and (4) can be used for finding initial values for $D_o$, t, and $f_p$.

Effects of Transducer Geometry and Sonication Frequency on Acoustic Beam Profile In this Section, COMSOL simulation results are provided to study the effects of $D_o$, t, and $f_p$ on the acoustic beam profile, generated by miniaturized transducers made of PZT-5A. The minimum required acoustic intensity, which depends on $f_p$ and is within W/cm² range, is the key parameter for successful ultrasound stimulation [35]. In this paper for fair comparison between different cases, normalized acoustic intensity, which is defined as the ratio of the acoustic intensity to the transducer's input electrical power, is calculated and reported.

For the μUS model in COMSOL, each miniaturized transducer (US) was located inside the castor oil with an attenuation coefficient of 0.8 dB/cm/MHz to mimic the soft tissue. FIGS. 10a, 10b, and 10c show the simulated normalized intensity profile for three different transducers with [$D_o$=0.2 mm, t=0.2 mm, $f_p$=0.5 MHz], [$D_o$=0.75 mm, t=0.2 mm, $f_p$=5 MHz], and [$D_o$=4.5 mm, t=0.2 mm, $f_p$=5 MHz], respectively. The transducers in FIGS. 10a and 10b with $D_o$<1 mm can be considered as examples for implanted (inside the brain) version of the μUS in FIG. 8, while FIGS. 10b and 10c provide examples for μUS from the brain surface. FIG. 10A shows the local intensity maxima around the transducer (i.e. high resolution) at even low $f_p$ of 0.5 MHz. FIGS. 10B and 10C show focused high-resolution intensity at the axial distance of ~0.15 mm and ~2 mm, respectively. Increasing $D_o$ and/or $f_p$ can further push the focus point to a larger depth.

The results in FIGS. 10A-10C show the considerable sensitivity of the beam profile, in terms of acoustic intensity magnitude, focal point, side lobes, and near-field effects, to the transducer geometry and $f_p$. As predicted by (4), by increasing $D_o$ and $f_p$, the focus point moved to larger axial distances.

Figure 11A:
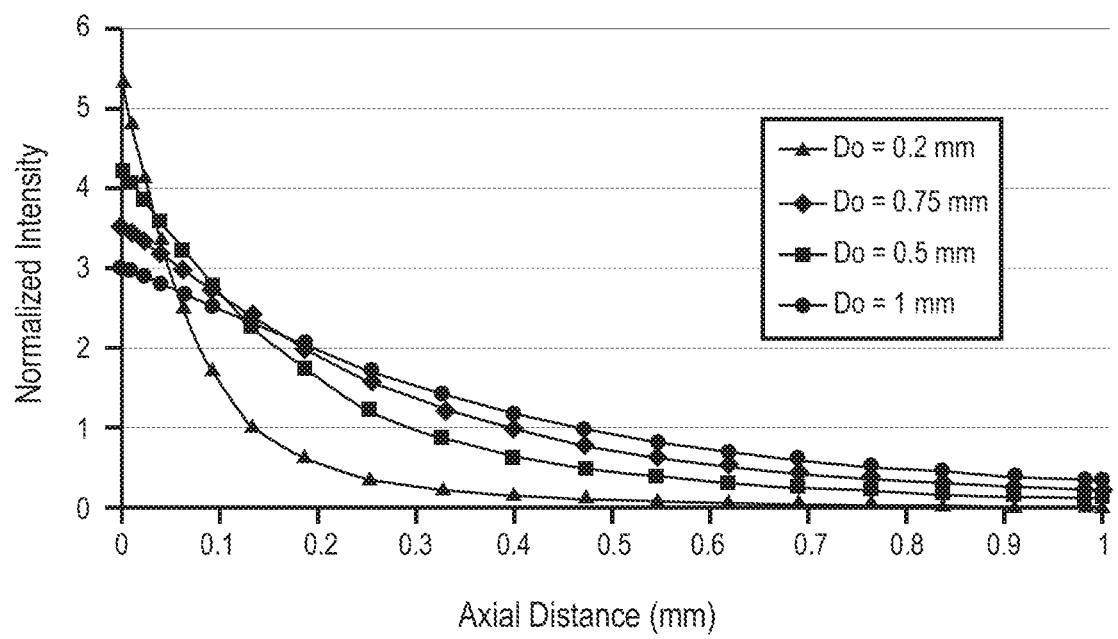
FIGS. 11A-11B are graphs showing simulated normalized intensity of a transducer.
Figure 11B:
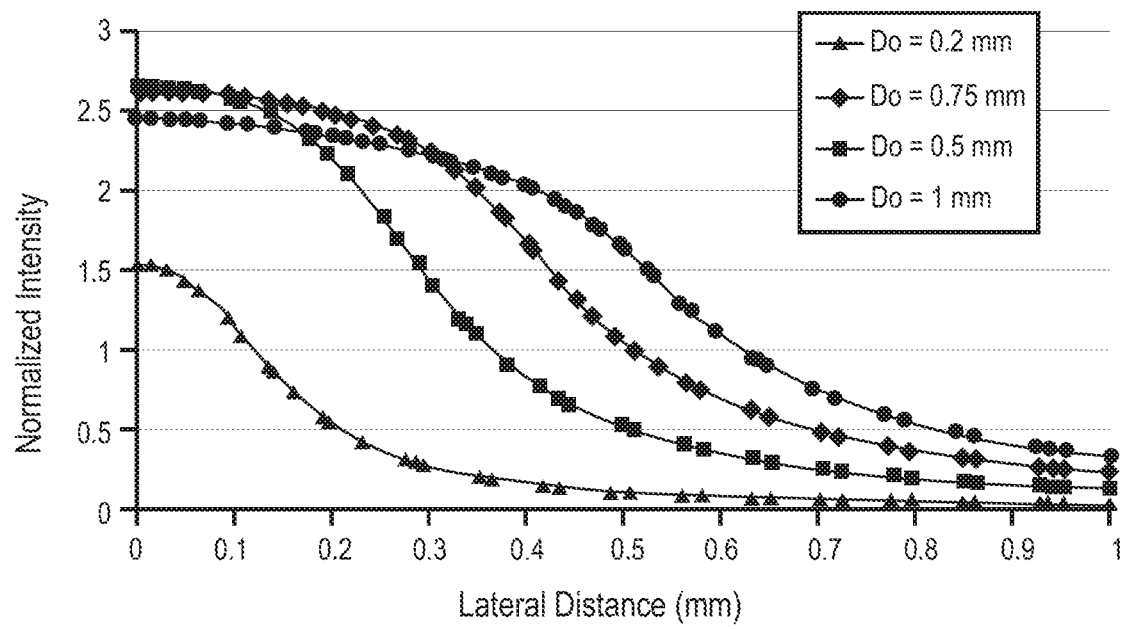

FIGS. 11A and 11B show the effect of $D_o$ variation of 0.2-1 mm on the normalized intensity for a transducer with t=0.2 mm, operating at $f_p$=0.5 MHz, in axial (zero lateral distance) and lateral (axial distance of 0.1 mm) directions, respectively. For all cases, similar to FIG. 10A the focal zone was approximately attached to the transducer surface. Small $D_o$ (<1 mm) results in a short Nin (4).

To consider the spatial resolution, the intensity full width of the half maximum (FWHM) is often calculated [35]. Therefore, according to FIGS. 11A-11B minimum FWHM of 60 μm and 150 μm in axial and lateral directions, respectively, can be achieved with $D_o$=0.2 mm at 100 μm axial distance. This results in a stimulation volume of ~0.06×0.15×0.15≈10⁻³ mm³ at $f_p$=0.5 MHz. For comparison, the 0.5-MHz transcranial FUS system in [35] has achieved a measured FWHM of 4.9 mm and 18 mm (stimulation volume of 18×4.9×4.9≈432 mm³) in lateral and axial directions, respectively. Therefore, our proposed μUS has reduced the stimulation volume by ~5 orders of magnitude at the same $f_p$. In other words, spatial resolution has been improved from sub-cm to sub-mm thanks to the proposed μUS method.

It can be observed in FIGS. 11A-11B that increasing $D_o$ enhances the acoustic intensity at larger axial distances at the cost of increasing FWHM in both axial and lateral resolution. For example, for $D_o$=1 mm intensity FWHM increased to ~0.3 mm and 0.55 mm in axial and lateral directions, respectively, equivalent to the larger stimulation volume of ~0.09 mm³.

Figure 12A:
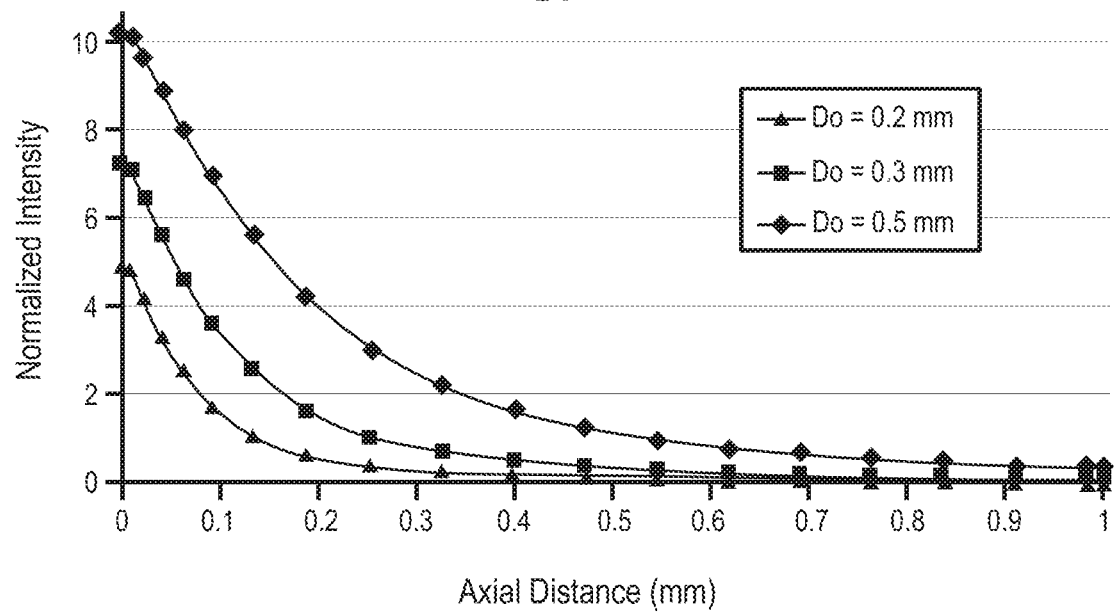
FIGS. 12A-12B are graphs showing simulated normalized intensity of a transducer.
Figure 12B:
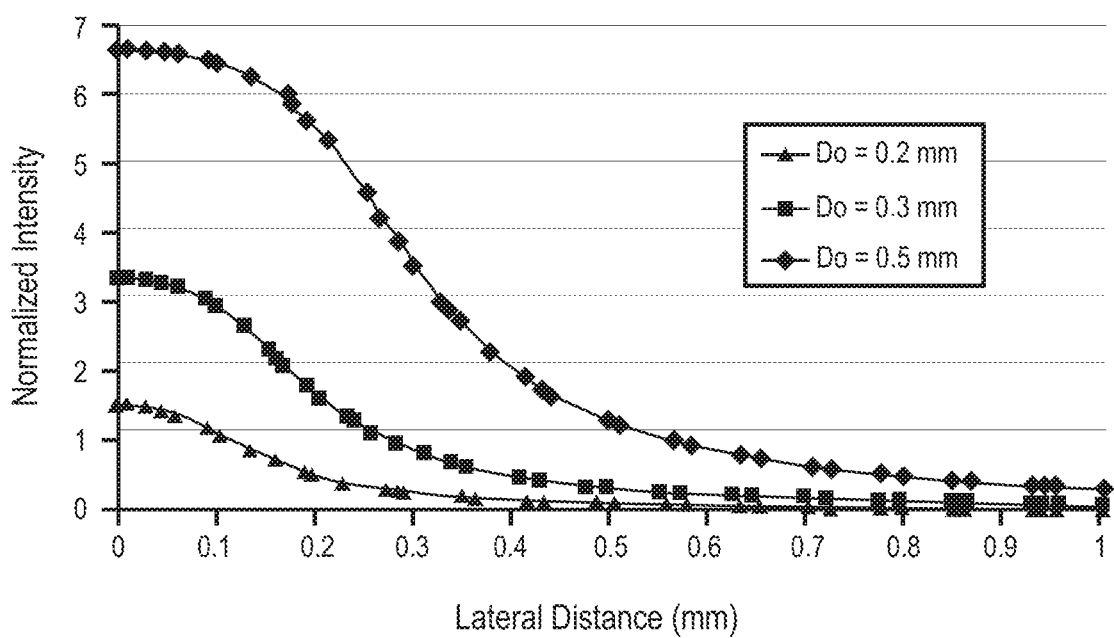

FIGS. 12A and 12B show the simulated normalized intensity of a transducer ($f_p$=0.5 MHz) with different $D_o$ and t in axial and lateral directions, respectively. Increasing $D_o$=t from 0.2 mm to 0.5 mm resulted in an increase of the intensity FWHM for both lateral (150 µm to 300 µm) and axial (60 µm to 150 µm) directions. Comparing FIGS. 11a-b and 12a-b implies that increasing t for similar $D_o$ can enhance the acoustic intensity with negligible effect on the spatial resolution. For example, the acoustic intensity has increased from 2.6 (FIG. 11B) to 6.6 (FIG. 12B) by increasing t from 0.2 mm to 0.5 mm ($D_o$=0.5 mm). For the same case, the intensity FWHM in lateral direction has maintained almost constant at 0.32 mm.

FIGS. 13a-13b show the effect of $f_p$ (0.5-5 MHz) on the beam profile generated by a transducer with $D_o$=0.75 mm and t=0.2 mm. As $f_p$ was increased, according to (2) and FIG. 13A the focus point moved to larger axial distances. The intensity FWHM reduced in both lateral and axial directions as $f_p$ was increased (better spatial resolution). At $f_p$=5 MHz, minimum intensity FWHM of 75 µm in lateral direction was achieved (FIG. 13B). Also as $f_p$ was increased, a significant enhancement in the normalized intensity can be observed in FIGS. 13A-13B, because $f_p$ was closer to $f_{tr}$ or $f_{rr}$, which are high for small transducers according to (1), i.e. more efficient transducer.

Furthermore, a novel modulation technique, called ultrasonic harmonic modulation (UHM), for wideband pulse-based ultrasonic communication may be used with the above-discussed embodiments. According to UHM, two narrow pulses with particular amplitudes and time delays are sent in the transmitter such that their associated ringing in the receiver creates a short ringing by surpassing the ringing of the first pulse with that of the second pulse.

Simulation Vs. Measurement

To validate the accuracy of our measurements, the simulated and measured characteristics of the transducers were compared (only $US_1$ simulated results are reported). Table I shows the specifications and measured electrical and acoustic characteristics of $US_1$-$US_9$ transducers.

For each transducer, we report the following measured parameters. 1) electrical impedance measured using a network analyzer (E5071C, Keysight Tech., Santa Rosa, Calif.), 2) acoustic intensity profile in axial and lateral directions normalized to the maximum intensity in that specific measurement, 3) axial and lateral resolution, defined as half-power (−3 dB) beam width (normalized intensity reduced to 0.5) in axial and lateral directions, respectively. For axial resolution, the beam width in the far-field region starting at N is reported, because near-field measured intensities are not reliable. For the lateral resolution, the beam width at N is reported. 4) $I^2PR$ as discussed earlier. 5) IL, which was measured using the similar method in. It should be noted that the measured IL results represent two-way insertion loss and include the losses introduced by the medium (water), the reflector (air), the divergence of the ultrasound beam, which is the main reason for relatively low IL values in Table I, and measurement setup nonidealities. To exclude such losses, 6) the ratio of the acoustic power to electrical power (p) was also measured. The acoustic power in $\eta_T$ was calculated by integrating the measured acoustic intensity over a plane in parallel with the transducer surface at the focal length (N).

Figure 14A:
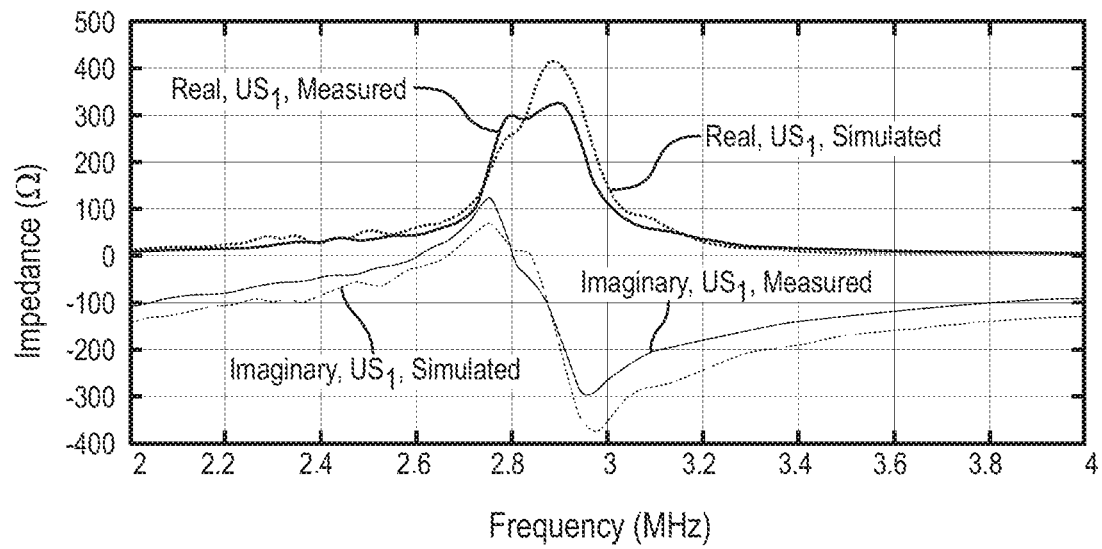
Figure 14B:
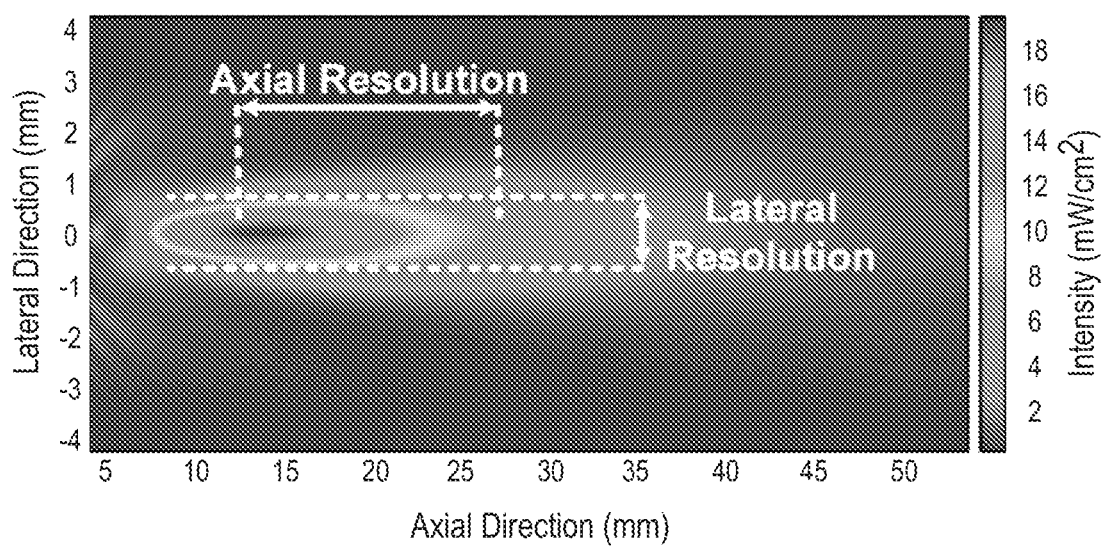

FIGS. 14A to 14D compare measured and simulated results of electrical and acoustic characteristics of $US_1$. FIG. 14A shows the $US_1$ electrical impedance with the simulated/measured series and parallel resonance frequencies of 2.66/2.6 MHz and 2.85/2.8 MHz, respectively. FIGS. 14B and 14C show the simulated and measured acoustic beam profiles, respectively, at the parallel resonance frequencies for the same sinusoidal input with 1 V amplitude across $US_1$. FIG. 14D compares simulated and measured axial and lateral resolutions extracted from FIGS. 14B and 14C. The simulated/measured N and axial and lateral resolutions were 12/14.25 mm, 15/14.75 mm and 1.3/1.9 mm, respectively. For the same input, the maximum simulated and measured acoustic intensity at the focal zone was 19.6 mW/cm² and 11 mW/cm², respectively. This discrepancy could be due to the differences in the boundary condition (related to reflections), PZT-5A parameters, lateral resolution, and electrical impedance (related to input power) between simulation and measurement setups. Therefore, for fair comparison of transducers, the measured normalized acoustic intensity and $I^2PR$ is also reported in this disclosure.

In the following subsections, measurement results are used to study the impact of $f_p$, transducer dimension ($D_o$, t), backing layer, focusing, and acoustic matching on the characteristics of the generated acoustic beam profile.

Sonication Frequency ($f_p$) Impact

Ideally, $f_p$ should be selected based on the transducer mechanical resonance frequency, which is $\omega_0/2\pi = v_d/2t$ for a disc-shaped transducer in the TE mode. But in practice the backing and matching materials can affect $\omega_0$. In addition, $C_0$ and $C'$ capacitors in FIG. 5C, which are in series with the equivalent mechanical impedance, appear in the electrical impedance (seen from the input electrical port in FIG. 5C), thereby deviating the electrical resonance frequency from $\omega_0$. Typically, the electrical impedance plot shows the series and parallel resonance frequencies as in FIG. 14A. For a transducer with a high $\Theta_T$, these two frequencies merge to $\omega_0/2\pi$.

To show the impact of operation at series vs. parallel resonance, the normalized acoustic intensity of $US_1$ was measured at three different frequencies of 2.6 MHz (series resonance, FIG. 15A), 2.7 MHz (between series and parallel resonance, FIG. 15B) and 2.8 MHz (parallel resonance, FIG. 14C). At 2.6 MHz, 2.7 MHz and 2.8 MHz, measured N was 20 mm, 14 mm and 14.25 mm, and the maximum $I_2PR$ was 0.45 cm', 3.1 cm' and 6.6 cm$^{-2}$, respectively. This resulted in 14.7 times improvement in $I^2PR$ by operating at the parallel resonance (2.8 MHz) compared to the series resonance (2.6 MHz). As shown in FIG. 15C, axial and lateral resolution changed at different frequencies. In particular, worse resolution and lower $I^2PR$ were achieved at 2.6 MHz. Therefore, the beam profile is sensitive to $f_p$, and one should sweep $f_p$ around the transducer resonance frequencies to find the optimal $f_p$ that maximizes $I^2PR$. This said, in all transducers we found the optimal $f_p$ at or close to the parallel resonance frequency.

It is worth noting that the optimal $f_p$ may not be exactly the same as the transducer center frequency ($f_c$) which is usually found from pulse-echo measurements. In this disclosure, the optimal $f_p$ is found when $I^2PR$ is maximized, while operating at $f_c$ may not necessarily result in the maximum $I^2PR$. Because, for maximizing $I^2PR$ the acoustic intensity at the focal zone and the input electrical power should be maximized and minimized, respectively, while at $f_c$ only the pulse-echo frequency spectrum reaches its maximum. For example, the $f_c$ of $US_1$ is 2.7 MHz, but $I^2PR$ is maximum at 2.8 MHz. This is mainly due to the higher transducer impedance at 2.8 MHz, which resulted in lower input power.

Backing Layer Impact

Acoustic characteristics of the transducer backing layer not only impacts the generated acoustic intensity but can also affect the transducer electrical impedance. Based on (2), $R_0$ (transducer impedance at resonance) is inversely proportional to $Z_B$, and therefore, small $Z_B$ (high $R_0$) leads to higher Q, enhancing the $\Theta_T$. In other words, at small $Z_B$ most of the mechanical wave, which reaches the back acoustic port in FIG. 5C, is reflected back towards the front acoustic port, generating higher acoustic pressure in the medium.

To study the backing material impact, we measured and compared the acoustic beam profile of air-backed $US_1$ and PCB-backed $US_2$ with similar dimension. The $Z_B$ values for air and PCB are ~$4 \times 10^{-4}$ MRayl and 6.6 MRayl, respectively. As shown in FIG. 16A, at the parallel resonance the air-backed $US_1$ achieved higher impedance and sharper phase transition, indicating that its Q is higher. The measured acoustic beam profiles of $US_1$ and $US_2$ in FIGS. 14C and 16B ($f_{p,US2}$=2.8 MHz), respectively, as well as their axial and lateral resolutions in FIG. 16C are almost similar, indicating that the beam shape is less sensitive to the backing material, although N is slightly higher for $US_2$ (14.25 mm vs. 16.75 mm). The maximum $I^2PR$ and $\Theta^T$ of $US_1/US_2$ were 6.6/2.4 $cm^{-2}$ (175% increase in $I^2PR$ by changing the backing layer from PCB to air) and 36.7/16.3%, respectively, implying that air backing with smaller $Z_B$ leads to higher energy efficiency as predicted by the theory. Therefore, unlike acoustic imaging, in which backing materials with high $Z_B$ and large damping are preferred (low Q, wideband), in μUS (and tFUS) backing materials with low $Z_B$ and small damping (high Q, narrowband) are preferable to increase the $I^2PR$.

Transducer Dimension ($D_o$, t) Impact

Figure 17A:
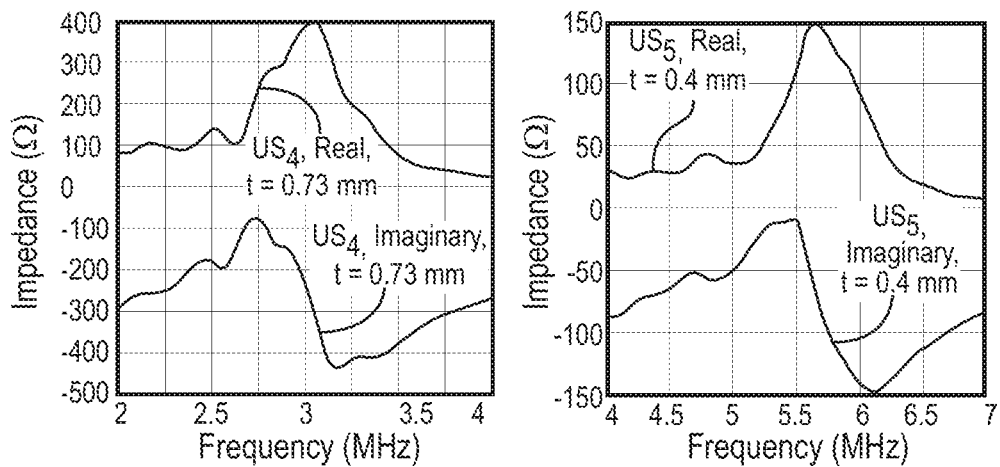
FIGS. 17A-17D are graphs and images showing an impact oft on the acoustic beam profile.
Figure 17B:
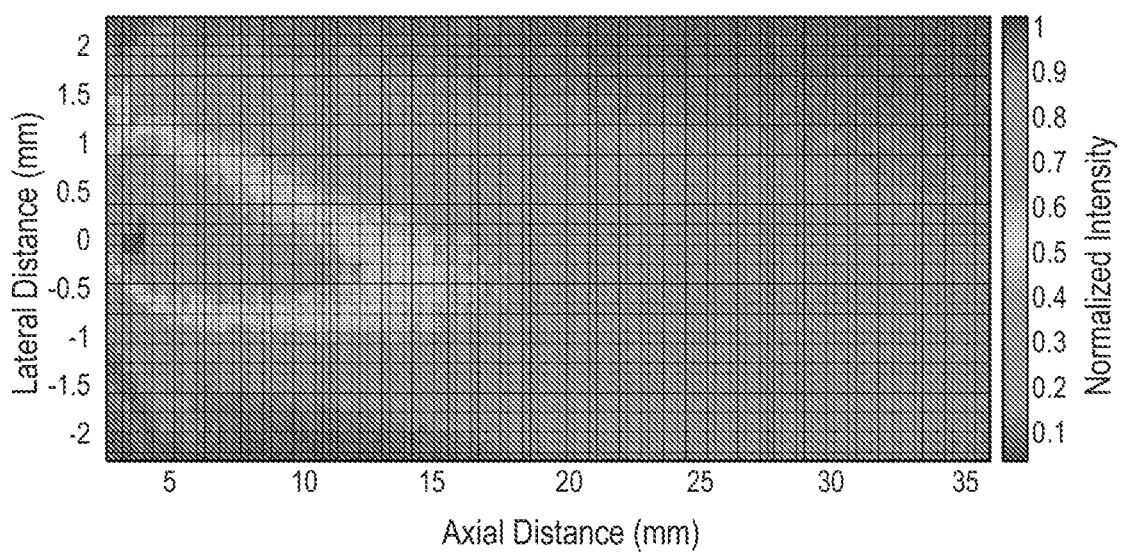
Figure 17C:
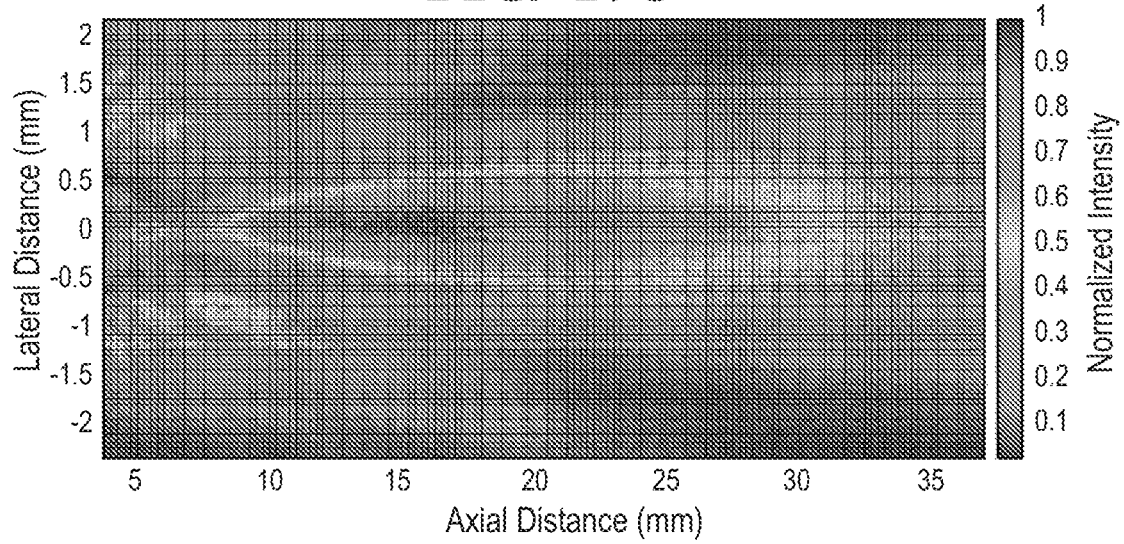
Figure 17D:
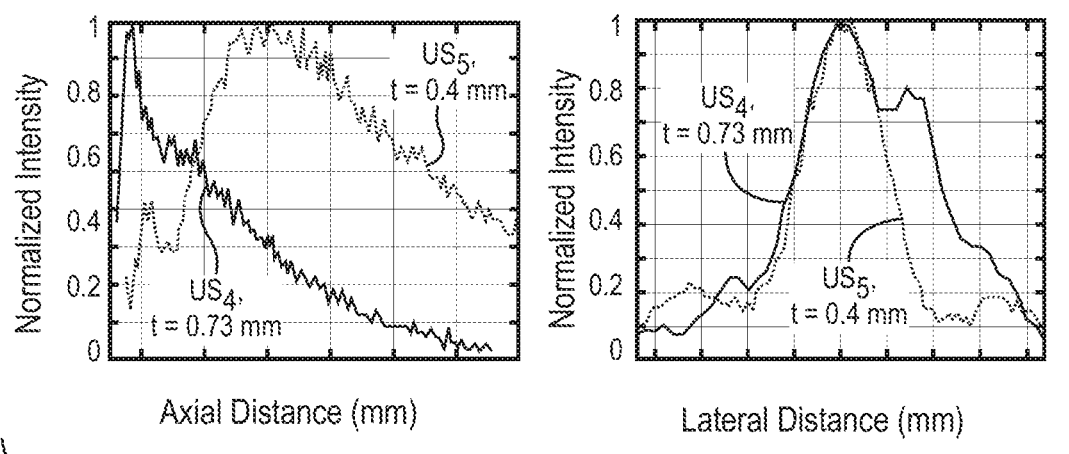

The transducer dimension, including $D_o$ and t, can significantly affect the transducer performance since $\omega_0 = \pi v_a/t$ and N in (5) (see below) highly depend on t and $D_o$, respectively. To study the impact of t, the measured characteristics of two PCB-backed transducers with similar $D_o$=4.2 mm and different t of 0.73 mm ($US_4$) and 0.4 mm ($US_5$) are compared in FIGS. 10A-10C. As shown in the measured electrical impedance plots in FIG. 17A, the parallel resonance frequency of $US_4$ was 3.05 MHz which was smaller than that of $US_5$ (5.66 MHz) due to its larger t. FIGS. 17B and 17C shows the measured normalized acoustic intensity profile of $US_4$ and $US_5$, respectively. FIG. 17D compares the axial and lateral resolution of these two transducers. The $US_4$ and $US_5$ achieved different N of 4.35 mm and 14 mm mainly due to their $f_p$ difference. Higher $f_p$ resulted in larger N. In addition, both transducers achieved similar lateral resolution of ~1.1 mm. As discussed in this disclosure, since the focal zone of $US_4$ was close to the transducer surface, its measured acoustic beam in FIG. 17B is somewhat affected by the coupling noise.

In order to study the impact of $D_o$, we measured and compared acoustic beam profile of two PCB-backed transducers with similar t=0.75 but different $D_o$ of 5 mm ($US_3$) and 6.8 mm ($US_2$) at $f_p$=2.8 MHz. The measured electrical impedance of $US_2$ and $US_3$ was already shown in FIG. 16A, indicating that they have similar parallel resonance frequency of ~2.8 MHz. However, at parallel resonance $US_3$ with smaller $D_o$ achieved higher impedance ($R_0$), because $R_0$ is inversely proportional to $C_0 \propto A \propto D_o^2$ based on (2).

FIGS. 16B and 18A shows the measured normalized acoustic intensity profile of $US_2$ and $US_3$, respectively. FIG. 18B compares their axial and lateral resolution. The measured N for $US_2$ and $US_3$ were 16.75 mm and 11.25 mm, respectively. Since N is proportional to $D_o^2$ based on (5), $US_3$ achieved larger N. The lateral resolution of $US_2$ with smaller $D_o$ was better than that of $US_3$ (1.75 mm vs. 2.2 mm), because beam width is proportional to $D_o$. Finally, the maximum $I^2PR$ of $US_2$ and $US_3$ were 2.4 $cm^{-2}$ and 3.4 $cm^{-2}$, respectively. Higher $I^2PR$ of $US_3$ for 41.6% could be due to its smaller focal zone and higher Q (see FIG. 16A). Therefore, smaller $D_o$ helps to improve lateral resolution at shorter N as well as the energy efficiency to some extent for relatively large $D_o/t$ ratio.

To study the effect of aggressive size scaling (both $D_o$ and t), the acoustic intensity profile of a PCB-backed transducer ($US_6$) with small $D_o$=2.8 mm and t=0.3 mm was measured at its parallel resonance frequency of 9.56 MHz, as shown in FIG. 19. The axial and lateral resolution was 6.25 mm and 0.5 mm, respectively, which were significantly improved compared to $US_2$ and $US_3$. This is mainly due to both decrease in $D_o$ and increase in $f_p$. The maximum $I^2PR$=16 $cm^{-2}$ of $US_6$ was also much higher than $US_2$ and $US_3$, mainly due to smaller $D_o$ and resulting improved lateral resolution. This said, μUS at higher $f_p$ often requires larger threshold intensity to stimulate the neural tissue.

Beam Focusing Impact

Beam focusing is known to improve the spatial resolution of the generated acoustic beam by a transducer. This could consequently enhance the acoustic intensity at the focal zone, improving the energy efficiency. As described in this disclosure, for the focused transducers we fabricated spherically shaped acoustic lenses (at the front side) with two different materials, EPO-TEK301 ($US_8$) and EPO-TEK301+ Alumina ($US_9$), on top of the PZT disc as shown in FIGS. 5D(d) and 5D(e), respectively. These PCB-backed transducers had similar dimension ($D_o$=5.8 mm, t=1 mm). For fair comparison, another unfocused (flat) transducer ($US_7$) with EPO-TEK301 matching layer and similar dimension was also fabricated. It should be noted that Sylgard-184 was not used in U57-9, because sound speed in the lens material should be higher than that in the medium (water in our experiment) for proper acoustic matching.

FIG. 20A shows the measured electrical impedance of $US_{7-9}$. The parallel resonance frequency of the unfocused ($US_7$) and focused ($US_{8,9}$) transducers was 2.2 MHz and 2.47 MHz, respectively. Therefore, the focusing lens slightly changed the resonance frequency. For the focused transducers ($US_{8,9}$), $US_8$ with EPO-TEK as the lens material achieved higher Q (larger impedance and sharper phase transition at resonance), because by adding Alumina to the EPO-TEK as in $US_9$, the acoustic impedance of the lens material ($Z_F$) increased and led to lower $R_0$ at resonance (lower Q) based on (2).

FIGS. 20B, 20C, and 20D shows measured normalized acoustic beam intensity of $US_{7-9}$, respectively. FIG. 20E compares the axial and lateral resolution of these three transducers. For $US_{7-9}$, N was 4.6 mm, 8.5 mm and 7 mm, respectively. While the axial and lateral resolution of unfocused $US_7$ was 12 mm and 1.8 mm, respectively, for focused $US_8$ and $US_9$ the axial and lateral resolution was very close at 6.5 mm and ~1 mm, respectively. Therefore, both axial and lateral resolution was significantly improved by ~1.8 times (from 12 mm to 6.5 mm and 1.8 mm to 1 mm) using the focusing lens. Finally, the measured maximum $I^2PR$ of $US_{7-9}$ were 2.9 $cm^{-2}$, 9.3 $cm^{-2}$ and 12.9 $cm^{-2}$, respectively, indicating that focused $US_{8,9}$ transducers can achieve much higher energy efficiency (3.2 and 4.4 times, respectively) due to their focusing feature.

Acoustic Matching Impact

Any mismatch between the acoustic impedance of the piezoelectric material, encapsulation layer (Sylgard-184 in $US_{1-6}$) and the tissue medium can affect the generated acoustic intensity by the transducer due to the acoustic reflections. Ideally, similar acoustic impedance for all these three media is needed. But there is a large difference between the acoustic impedance of the PZT ($Z_c$=33 MRayl) and water ($Z_m$=1.48 MRayl), mimicking the tissue medium in our measurements. To reduce the acoustic reflections due to the mismatch, the encapsulation layer can be employed as the matching layer as well. For optimal acoustic matching, the thickness and acoustic impedance of this layer should be $\lambda/4$ and $(Z_c \times Z_m)^{0.5}$, respectively.

To study the acoustic matching impact, $US_9$ transducer included both EPO-TEK and Alumina as both the focusing lens and matching material (FIG. 5D(e)). Alumina was added to EPO-TEK with the volume fraction of 30% leading to the acoustic impedance of 5.6 MRayl. The thickness of this layer at the center of the PZT disc was $\sim\lambda/4$=0.25 mm ($f_p$=2.47 MHz). For fair comparison, focused $US_8$ with similar dimension but without Alumina was used. For $US_8$, only EPO-TEK with acoustic impedance of 3 MRayl, which is lower than optimal $(Z_c \times Z_m)^{0.5}$=7 MRayl, provided poor acoustic matching. As shown in FIGS. 20a-20e, $US_9$ achieved similar performance to $US_8$ with respect to the axial and lateral resolution, but it achieved ~1.4 times higher maximum I²PR (12.9 cm' vs. 9.3 $cm^{-2}$) even with lower Q as seen in FIG. 20A. Therefore, acoustic matching is key in maximizing the energy efficiency. With our current fabrication process, it was hard to accurately control the lens material thickness at 0.25 mm for perfect acoustic matching, which could further improve I²PR.

Measurement Results with Bio-Phantom

Figure 21:
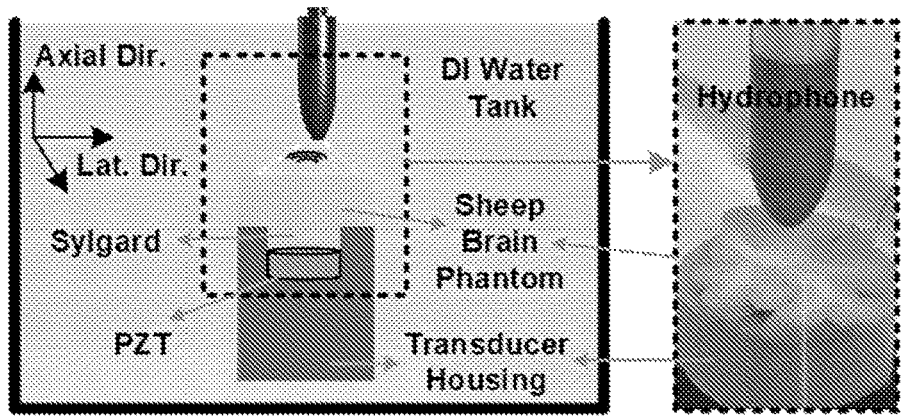
FIG. 21 is schematic of an experiment setup used to measure an impact of a sheep brain phantom.

In order to study the acoustic beam profile in a more realistic setup, several measurements were conducted with a sheep brain phantom (Carolina Biological Supply, Burlington, N.C.). In this section, we only provide the measurement results for $US_1$ and $US_6$, operating at low and high $f_p$s of 2.8 MHz and 9.56 MHz, respectively. FIG. 21 shows our modified measurement setup with a slice of 4.5 mm thick brain phantom filling the space between the transducer (2 mm away from the PZT disc surface) and hydrophone in the water tank. At the axial distance of 14 mm, the acoustic beam profile at the lateral direction (a plane parallel to the transducer surface) with and without the phantom was measured. The axial distance of 14 mm within the focal zone of both transducers was chosen to avoid any physical contact between our fragile hydrophone and the phantom.

Figure 22A:
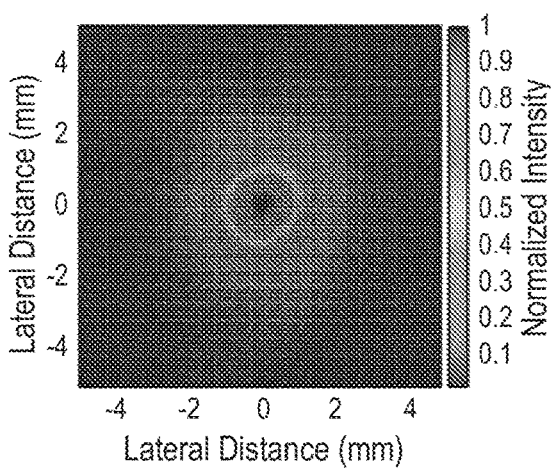
FIGS. 22A-22D are images comparing measured normalized acoustic beam profile.
Figure 22B:
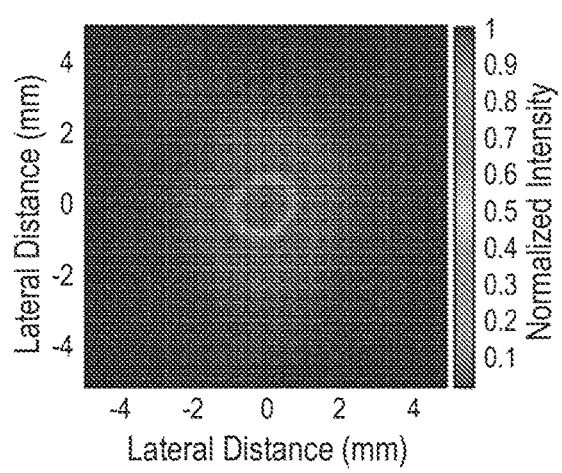
Figure 22C:
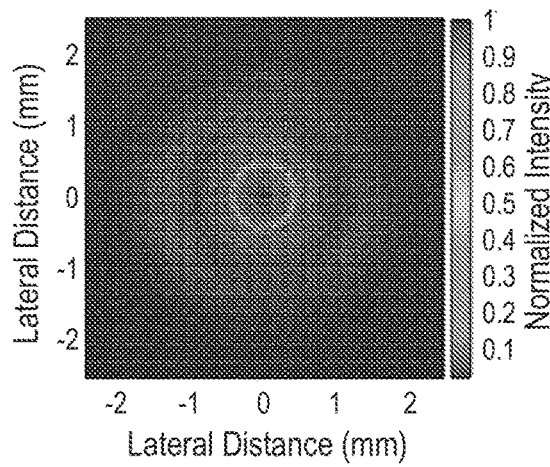
Figure 22D:
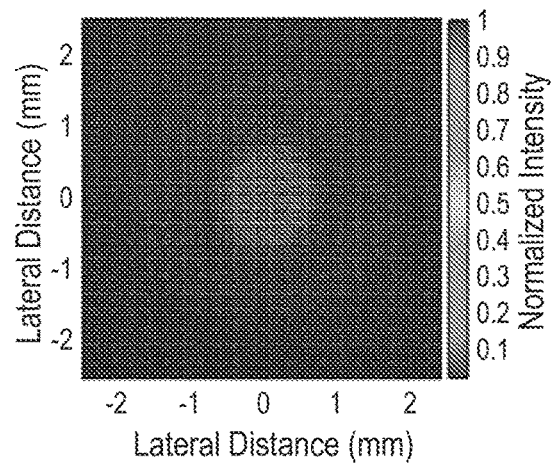

FIGS. 22A and 22B show the $US_1$ measured normalized acoustic beam profile in lateral direction without and with the brain phantom, respectively. The lateral resolution of $US_1$, which was 2 mm, was not affected by the phantom, however, the maximum acoustic intensity slightly reduced by ~1.1 dB by introducing the phantom. FIGS. 22C and 22D show similar results for $US_6$. Since $US_6$ was operating at the higher $f_p$ of 9.56 MHz, after introducing the phantom both the lateral resolution and maximum acoustic intensity degraded from 0.85 mm to 0.9 mm and by 5.4 dB, respectively. The attenuation coefficient of the soft tissue is within 0.5-1 dB/(MHz·cm), which matches with our measurements. Therefore, while the shape (spatial resolution) of the acoustic beam profile is less sensitive to the slight inhomogeneity of the phantom medium, the acoustic loss increases at the presence of the phantom particularly at higher frequencies.

FIGS. 23A and 23B summarize the integration and development of the whole μUS system into a portable device for proof-of-concept testing on rodents (e.g. rats). The device could mainly integrate mm-sized ultrasound transducers, which were studied in this paper, and the electronics. Due to the transducer's design in this work, multiple mm-sized transducers can be placed on the animal's head to target multiple brain regions. The transducer could be any design in Table I. However, based on the presented study the required electrical power can be reduced using air-backing, focusing and acoustic matching techniques.

Building upon our experience, a miniaturized 3D-printed plastic housing may fabricated to hold the air-backed PZT material and then add an acoustic lens to achieve focusing and acoustic matching similar to the transducer in FIG. 5D(e). A 3D-printed plastic pedestal may be surgically fixed onto the animal skull and positioned above the neural target. The pedestal could be filled with ultrasound gel to couple the generated ultrasound by the transducer to the tissue. The skull below the transducer can be partially removed or thinned to reduce ultrasound attenuation and reflection.

Figure 4D:
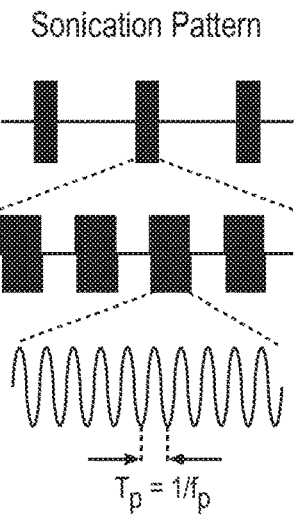
FIG. 4D is a graphical representation of a sonification pattern of the embodiment shown in FIG. 4C.

The electronics could mainly include a multi-functional chip, which may be designed in a high-voltage CMOS process, that could integrate a power management circuitry to provide enough voltage and power levels required in μUS, a high-voltage driver to drive ultrasound transducers, and a configurable stimulation pattern generator to generate the optimal sonication pattern as shown in FIG. 4D. The chip could be integrated either with the transducers or placed on the animals' back (and wired to transducers) inside commercially available rodent jackets to distribute the weight on the animal body. After successful demonstration of this technology, we could extend to an ultrasound array and electronic beamforming as shown in FIG. 4C.

For both tFUS and μUS, safety against high ultrasound pressure levels should be considered. The Food and Drug Administration (FDA) has determined limitations on both average and peak of exposed ultrasound intensity to the tissue. The spatial-peak temporal-average intensity ($I_{spta}$) should be less than 720 mW/cm² and the mechanical index (MI), which is indicator of ultrasound peak intensity, should be less than 1.9. The requited acoustic pressure for tFUS is often below FDA threshold levels. Since μUS eliminates the effect of lossy skull, its required ultrasound pressure is less than that of tFUS at similar frequencies.

A comprehensive study on the acoustic and electrical characteristics of mm-sized piezoelectric transducers for μUS applications is discussed above. The operation and transmission line model of disc-shaped piezoelectric transducers were discussed to establish a basis for studying their acoustic beam profile. Using the PZT-5A piezoelectric material, nine sets of transducers with different dimensions, frequencies, backing materials, focusing features and matching materials were fabricated. Through comprehensive experimental studies of electrical impedance and hydrophone measurements of these ultrasound transducers, the impact of aforementioned design parameters on spatial (axial and lateral) resolution and acoustic beam intensity (related to energy efficiency) was studied. It was shown that transducer miniaturization, beam focusing, acoustic matching and overall quality factor are critical in improving spatial specificity and energy efficiency of μUS. These transducers could be used in vivo applications. These transducers and their applications are discussed below in more detail.

FIG. 9B shows the generated acoustic beam profile of a disc-shaped transducer which can be divided into two regions: near field and far field. At the boundary of these two regions, a focal zone appears at which the beam width is relatively narrowest (proportional to $D_o$) resulting in the maximum acoustic intensity. As shown in FIG. 9B, even an unfocused disc-shaped transducer has a natural focus. The near-field region begins from the transducer surface and ends at the focal point defining the focal length (N), $$N = \frac{f_p D_o^2}{4v}, \tag{5}$$

where v is the sound velocity in the medium. In near-field region (particularly near the transducer surface), there are several local maxima and minima which are highly dependent on the medium (i.e., difficult to model their exact locations).

The far-field region begins at the focal point at which the beam starts to diverge, thereby increasing the beam width along the axial direction. As shown in FIG. 9B, the acoustic intensity decreases monotonically in the far-field region, and its variation in the lateral direction is less than that in the near field. In far field, the beam profile can be predicted with higher accuracy, which is preferable for reliable operation.

Figure 6:
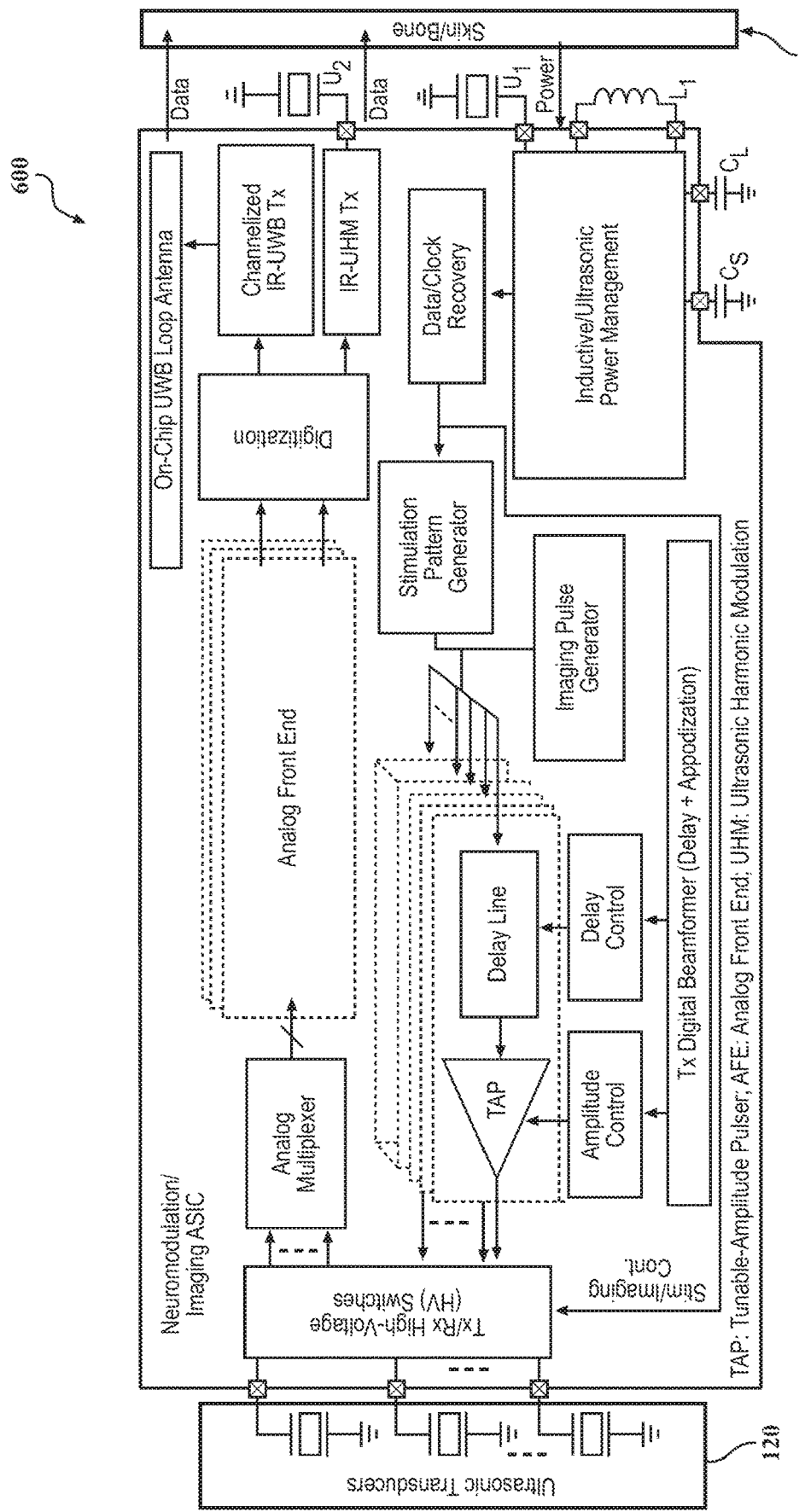
FIG. 6 is a simplified block diagram of a proposed dual-model wireless ASIC for neuromodulation and hemodynamic imaging.

The dual-modal (modulation and imaging) ASIC, as shown in FIG. 6, in the proposed implantable technology (FIGS. 4a-4b) has the unique capabilities of 1) generating a highly focused ultrasonic beam with micrometer resolution for neuromodulation (only for method-1 in FIG. 4A) or driving the implanted sub-millimeter sized transducer (only for µUS in FIG. 4B), 2) recovering ultrasonic echoes with high spatiotemporal resolution (micrometers, milliseconds) with a variable spatial coverage (mm² to cm²) for hemodynamic imaging, and 3) receiving wireless power both inductively and ultrasonically and generating a high-voltage supply. FIG. 6 is a simplified block diagram of the proposed dual-modal fully ASIC for neuromodulation and hemodynamic imaging. An on-chip digital beamformer may be implemented to control the delay and amplitude of the signal in each cell of the array that could consist of an analog delay line and an efficient tunable-amplitude pulser with high-voltage level shifters for driving the transducer array. The imaging block of the ASIC may either sequentially focus the ultrasonic beam in the transmitter and measure echoes of each firing from one transducer, or fire with one transducer in the transmitter and receive echoes from multiple transducers in the receiver. A wideband transmitter, such as impulse radio ultra-wideband (IR-UWB), transmits the imaging data to an external processor for reconstructing images with on-chip UWB loop antennas.

For wideband data transmission in PNS implants, pulse- or carrier-based modulation technique can be used. As shown in FIG. 5B, two stacked or side-by-side ultrasonic transducers can be used in the implant for power recovery and data transmission. For pulse-based communication, sharp pulses are transmitted to create a short ringing in the receiving ultrasonic transducer.

Figure 24:
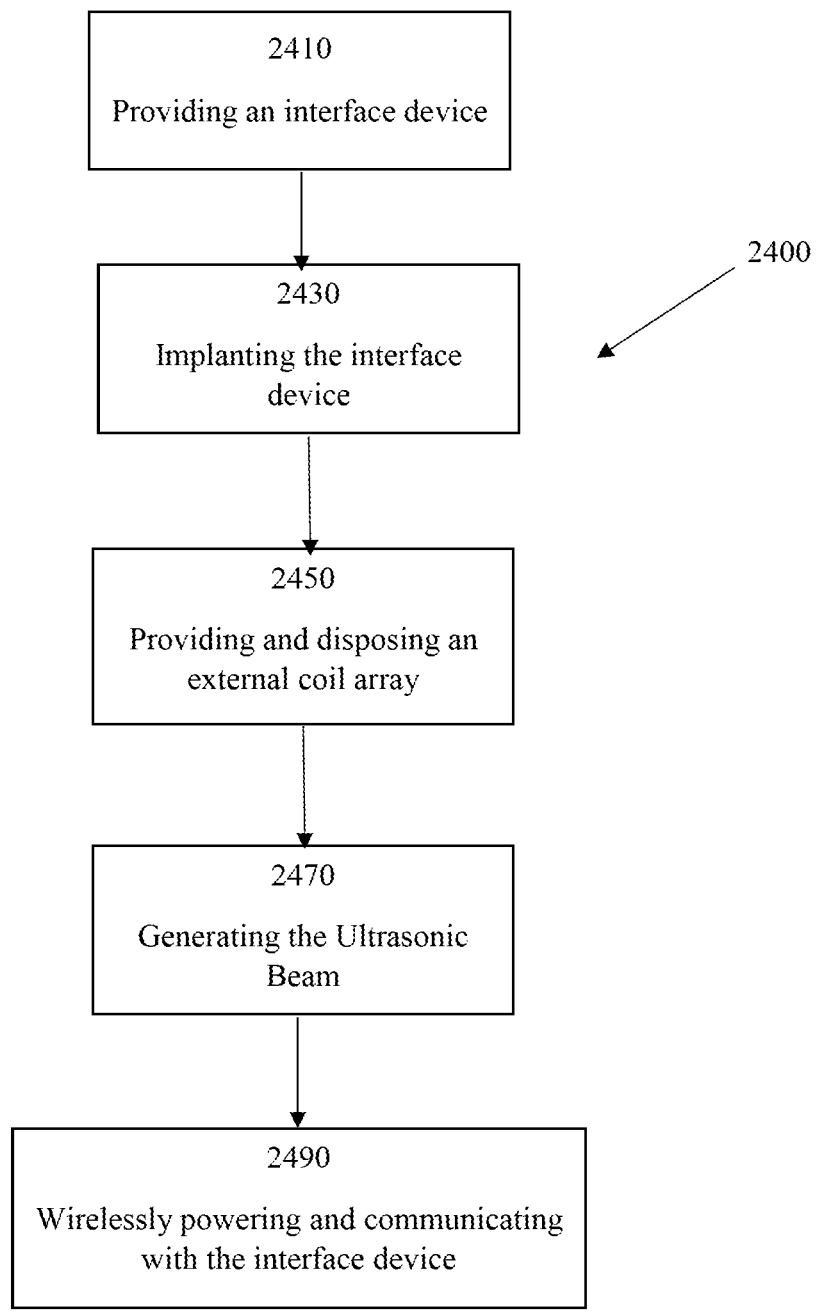
FIG. 24 is a flow chart of a method according to this disclosure.

FIG. 24 shows a flow diagram of a method 2400 of neural stimulation and imaging of nervous system of a subject according to this disclosure. The method 2400 includes the steps of providing an interface device 2410 that is operable to generate an ultrasonic beam for neuromodulation and imaging of a targeted neural structure of a subject; implanting the interface device in the subject 2430; and providing and disposing an external coil array 2450 over the targeted neural structure of the subject, wherein the external coil array is wirelessly powering and communicating with the interface device. At step 2470, the ultrasonic beam is generated by the interface device and the ultrasonic beam is transmitted towards the targeted neural structure for neuromodulating and imaging of the targeted neural structure. As noted above, several approaches for transmitting and receiving the beam (e.g. beamforming) may be used for stimulating (e.g. using beams as point source) and imaging (e.g. detecting blood volume) of the targeted neural structure.

Step 2490 includes the interface device being wirelessly powered by the external coil array. The interface device is communicating with the external coil array for performing neuromodulation and imaging of the targeted neural structure. For example, the external array provides signals/commands for performing neuromodulation and imaging as well as receives imaging related data from the interface device for further processing. In some embodiments, the imaging related data is transmitted to a central processing unit/control unit for further processing. The central processing unit/control unit may generate the signals/commands for transmission to the external coil array. It should be noted that a person skilled in the art would be able to use this disclosure for neuromodulation and imaging of the targeted neural structure and determine the miscellaneous requirements needed that are not detailed herein. The steps discussed above need not be followed in the order as shown.

In another method, step 2410 further includes the steps of providing the interface device comprising at least one ultrasonic transducer operable to focus an ultrasonic beam on the targeted neural structure of brain of the subject for neuromodulation and imaging of the targeted neural structure, and/or comprising at least one sub-millimeter sized ultrasonic transducer operable to generate an ultrasonic point-source near a targeted neural structure of brain of the subject for microscopic ultrasound neuromodulation and imaging of the targeted neural structure; step 2430 includes implanting the at least one ultrasonic transducer in a subdural region located over a brain surface and/or the at least one sub-millimeter sized ultrasonic transducer inside a neural tissue of the brain of the subject; and step 2450 includes providing and disposing an external coil array over a skull of the subject, wherein the external coil array is wirelessly powering and communicating with the interface device using an inductive link.

In another alternate method, the steps of providing the interface device 2410 further includes comprising at least one ultrasonic transducer operable to focus an ultrasonic beam on a targeted neural structure of peripheral nervous system (PNS) of the subject for neuromodulation and imaging of the targeted neural structure, and/or comprising at least one sub-millimeter sized ultrasonic transducer operable to generate an ultrasonic point-source near a targeted neural structure of peripheral nervous system (PNS) of the subject for microscopic ultrasound neuromodulation and imaging of the targeted neural structure; step 2430 includes implanting the at least one ultrasonic transducer over a nerve bundle of the PNS without any penetration into a parenchyma of the PNS, and/or the at least one sub-millimeter sized ultrasonic transducer in a nerve bundle of the PNS of the subject; and step 2450 includes providing and disposing an external coil or ultrasonic transducer array over skin of the subject that is covering the implanted interface device, wherein the external coil or ultrasonic transducer array is wirelessly powering and communicating with the interface device using an inductive or ultrasonic link.

As will be clear to those of skill in the art, the herein described embodiments of the present invention may be altered in various ways without departing from the scope or teaching of the present invention. As such, this disclosure should be interpreted broadly.

REFERENCES

[1] M. Nicolelis, "Actions from thoughts," Nature, 2001.
[2] T. Wagner, A. Valero-Cabre, and A. Pascual-Leone, "Noninvasive human brain stimulation," *Annul Rev. Biomed. Eng.*, vol. 9, pp. 527-565, 2007.
[3] V. Gradinaru, M. Mogri, T. Thompson, J. Henderson, and K. Deisseroth, "Optical deconstruction of parkinsonian neural circuitry," *Science*, vol. 324, pp. 354-359, 2009.
[4] J. Yianni, P. Bain, N. Giladi, M. Auca, R. Gregory, C. Joint, D. Nandi, J. Stein, R. Scott, and T. Aziz, "Globus pallidus internus deep brain stimulation for dystonic conditions: a prospective audit,"*Mov. Disord.*, vol. 18, pp. 436-442, 2003.
[5] M. Hodaie, R. Wennberg, J. Dostrovsky, and A. Lozano, "Chronic anterior thalamus stimulation for intractable epilepsy," *Epilepsia*, vol. 43, pp. 603-608, 2002.
[6] P. Holtzheimer and H. S. Mayberg, "Deep brain stimulation for psychiatric disorders," *Annu. Rev. Neurosci*, vol. 34, pp. 289-307, 2011.
[7] L. Gabriels, P. Cosyns, B. Meyerson, S. Andreewitch, S. Sunaert, A. Maes, P. Dupont, J. Gybels, F. Gielen, and H. Demeulemeester, "Long-term electrical capsular stimulation in patients with obsessive-compulsive disorder," *Neurosurgery*, vol. 52, pp. 1263-1274, 2003.
[8] A. Barbero and M. Grosse-Wentrup, "Biased feedback in brain-computer interfaces," *J. Neuroeng. Rehabit*, vol. 7, no. 34, pp. 1-4, 2010.
[9] J. Carmena, "Becoming bionic," *Spectrum*, vol. 49, no. 3, pp. 24-29, 2012.
[10] K. Deisseroth, "Optogenetics," *Nature*, vol. 8, January 2011.
[11] S. Ogawa, T. Lee, A. Kay, and D. Tank, "Brain magnetic resonance imaging with contrast dependent on blood oxygenation,"*Proc. Natl. Acad. Sci. USA*, vol. 87, pp. 9868-9872, December 1990.
[12] G. Buzsaki, "Large-scale recording of neuronal ensembles," *Nat. Neurosci.*, vol. 7, no. 5, pp. 446-451, May 2004.
[13] K. Famm, B. Litt, K. Tracey, E. Boyden, and M. Slaoui, "Drug discovery: A jump-start for electroceuticals," *Nature*, vol. 496, pp. 159-161, April 2013.
[14] K. Birmingham, V. Gradinaru, P. Anikeeva, W. Grill, V. Pikov, B. McLaughlin, P. Pasricha, D. Weber, K. Ludwig, and K. Famm, "Bioelectronic medicines: A research roadmap," *Nature Rev.*, vol. 13, pp. 399-400, June 2014.
[15] B. Bonaz, C. Picq, V. Sinniger, J. Mayol, and D. Clarencon, "Vagus nerve stimulation: from epilepsy to the cholinergic andti-inflammatory pathway,"*Neurogast. Mot.*, vol. 25, pp. 208-221, March 2013.
[16] J. Lee, D. Kim, S. Yoo, H. Lee, G. Lee, and Y. Nam, "Emerging neural stimulation technologies for bladder dysfunctions," *Int. Neurol. J.*, vol. 19, pp. 3-11, March 2015.
[17] G. O'Grady, J. Egbuji, P. Du, L. Cheng, A. Pullan, and J. Windsor, "High-frequency gastric electrical stimulation for the treatment of gastroparesis: a meta-analysis," *World J. Surgery*, vol. 33, no. 8, pp. 1693-1701, August 2009.
[18] H. Zhu, H. Sallam, and J. Chen, "Synchronized gastric electrical stimulation enhances gastric motility in dogs," *Neurogastroenterol. Motil*, vol. 293, no. 5, pp. 1875-1881, November 2007.
[19] S. Nag and N. Thakor, "Implantable neurotechnologies: electrical stimulation and applications,"*Med. Biol. Eng. Comput.*, vol. 54, no. 1, pp. 63-76, 2016.
[20] A. Barker, "The history and basic principles of magnetic nerve stimulation," *Electroencephalogr. Clin. Neurophysiol. Suppl.*, vol. 51, pp. 3-21, 1999.
[21] T. Wagner, A. Valero-Cabre, and A. Pascual-Leone, "Noninvasive human brain stimulation," *Annu. Rev. Biomed. Eng.*, vol. 9, pp. 527-565, 2007.
[22] A. Javadi, A. Beyko, V. Walsh, and R. Kanai, "Transcranial direct current stimulation of the motor cortex biases action choice in a perceptual decision task," *J. Cognitive Neurosci.*, vol. 27, pp. 2174-2185, October 2015.
[23] Deep Brain Stimulation Systems, Available Online: http://www.medtronic.com/
[24] E. Boyden, "A history of optogenetics: the development oftools for controlling brain circuits with light," *Biology Report*, May 2011.
[25] T. Kim, J. McCall, Y. Jung, X. Huang, E. Siuda, Y. Li, J. Song, Y. Song, H. Pao, R. Kim, C. Lu, S. Lee, S. Song, G. Shin, R. Al-Hasani, S. Kim, M. Tan, Y. Huang, F. Omenetto, J. Rogers, and M. Bruchas, "Injectable, cellular-scale optoelectronics with applications for wireless optogenetics," *Science*, vol. 340, pp. 211-216, April 2013.
[26] Utah Slanted Electrode Array, Blackrock Microsystems Inc.; Retrieved July 2016, Available Online: https://commonfund.nih.gov/sites/default/files/BlackrockInfo.pdf
[27] S. Ha, A. Akinin, J. Park, C. Kim, H. Wang, C. Maier, P. Mercier, and G. Cauwenberghs, "Silicon integrated high-density electrocortical interfaces,"*Proc. IEEE*, vol. 105, pp. 11-33, January 2017.
[28] M. Yin, D. Borton, J. Aceros, W. Patterson, and A. Nurmikko, "A100-channel hermetically sealed implantable device for chronic wireless neurosensing applications," *IEEE Trans. Biomed. Cir. Syst.*, vol. 7, pp. 115-128, April 2013.
[29] G. McConnell, H. Rees, A. Levey, C. Gutekunst, R. Gross, and R. Bellamkonda, "Implanted neural electrodes cause chronic, local inflammation that is correlated with local neurodegeneration," *J. Neural Eng.*, vol. 6, p. 056003, October 2009.
[30] W. Tyler, Y. Tufail, M. Finsterwald, M. Tauchmann, E. Olson, and C. Majestic, "Remote excitation of neuronal circuits using low-intensity, low-frequency ultrasound," *Plos One*, vol. 3, October 2008.
[31] Y. Tufail, A. Matyushov, N. Baldwin, M. Tauchmann, J. Georges, A. Yoshihiro, S. Tery, and W. Tyler, "Transcranial pulsed ultrasound stimulates intact brain circuits," *Neuron*, vol. 66, pp. 681-694, June 2010.
[32] Y. Tufail, A. Yoshihiro, S. Pati, M. Li, and W. Tyler, "Ultrasonic neuromodulation by brain stimulation with transcranial ultrasound," *Nature Protocols*, vol. 6, no. 9, pp. 1453-1470, 2011.
[33] W. Legon, A. Rowlands, A. Opitz, T. Sato, and W. Tyler, "Pulsed ultrasound differentially stimulates somatosensory circuits in humans as indicated by EEG and fMRI," *PLOS One*, vol. 7, December 2012.
[34] J. Mueller, W. Legon, A. Opitz, T. Sato, and W. Tyler, "Transcranial focused ultrasound modulates intrinsic and evoked EEG dynamics," *Brain Stim.*, vol. 7, pp. 900-908, September 2014.

[35] W. Legon, T. Sato, A. Opitz, J. Mueller, A. Barbour, A. Williams, and W. Tyler, "Transcranial focused ultrasound modulates the activity of primary somatosensory cortex in humans," *Nature Neurosci.*, vol. 17, pp. 322-333, February 2014.

[36] B. Min, A. Bystritsky, K. Jung, K. Fischer, Y. Zhang, L. Maeng, S. Park, Y. Chung, F. Jolesz, and S. Yoo, "Focused ultrasound-mediated suppression of chemically-induced acute epileptic EEG activity," *BMC Neurosci.*, pp. 12-23, 2011.

[37] S. Yoo, A. Bystritsky, J. Lee, Y. Zhang, K. Fischer, B. Min, N. McDannold, A. Pascual-Leone, and F. Jolesz, "Focused ultrasound modulates region-specific brain activity," *Neuroimage*, vol. 56, pp. 1267-1275, February 2011.

[38] H. Kim, S. Taghados, K. Fischer, L. Maeng, S. Park, and S. Yoo, "Noninvasive transcranial stimulation of rat abducens nrve by focused ultrasound," *Ultrasound Med. Biol.*, vol. 38, pp. 1568-1575, 2012.

[39] W. Lee, Y. Chung, Y. Jung, I. Song, and S. Yoo, "Simultaneous acoustic stimulation of human primary and secondary somatosensory cortices using transcranial focused ultrasound," *BMC Neurosci.*, vol. 17, 2016.

[40] W. Lee, H. Kim, Y. Jung, I. Song, Y. Chung, and S. Yoo, "Image-guided transcranial focused ultrasound stimulates human primary somatosensory cortex," *Scien. Reports*, vol. 5, pp. 1-10, March 2015.

[41] W. Lee, H. Kim, Y. Jung, Y. Chung, I. Song, J. Lee, and S. Yoo, "Transcranial focused ultrasound stimulation of human primary visual cortex," *Scien. Reports*, vol. 6, pp. 1-12, September 2016.

[42] W. Lee, S. Lee, M. Park, L. Foley, E. Purcell, H. Kim, K. Fischer, L. Maeng, and S. Yoo, "Image-guided focused ultrasound-mediated regional brain stimulation in sheep," *Ultrasound Med. Biol.*, vol. 42, pp. 459-470, 2016.

[43] T. Deffieux, Y. Younan, N. Wattiez, M. Tanter, P. Pouget, and J. Aubry, "Low-intensity focused ultrasound modulates monkey visuomotor behavior," *Current Biology*, vol. 23, pp. 2430-2433, December 2013.

[44] J. Kubanek, J. Shi, J. Marsh, D. Chen, C. Deng, and J. Cui, "Ultrasound modulates ion channel currents," *Nature Scien. Rep.*, vol. 6, pp. 1-14, April 2016.

[45] E. Juan, R. Gonzalez, G. Albors, M. Ward, and P. Irazoqui, "Vagus nerve modulation using focused pulsed ultrasound: potential applications and preliminary observations in a rat," Int. *J. Imaging Syst. Technol.*, vol. 1, pp. 67-71, March 2014.

[46] H. Baek, K. Pahk, and H. Kim, "A review of low-intensity focused ultrasound for neuromodulation," *Biomed. Eng. Lett.*, January 2017.

[47] A. Bystritsky and A. Korb, "A review of low-intensity transcranial focused ultrasound for clinical applications," *Curr. Behav. Neurosci. Rep.*, vol. 2, pp. 60-66, 2015.

[48] L. Ai, J. Mueller, A. Grant, Y. Eryaman, and W. Legon, "Transcranial focused ultrasound for BOLD fMRI signal modulation in humans, *IEEE* 2016.

[49] T. Dickey, R. Tych, M. kliot, J. Loseser, K. Pederson, and P. Mourad, "Intense focused ultrasound can reliably induce sensations in human test subjects in a manner correlated with the density of their mechanoreceptors," *Ultrasound in Med. Biol.*, vol. 38, vo. 1, pp. 85-90, 2012.

[50] E. Mehic, J. Xu, C. Caler, N. Coulson, C. Moritz, and P. Mourad, "Increased anatomical specificity of neuromodulation via modulated focused ultrasound," *PLOS One*, vol. 9, February 2014.

[51] R. King, J. Brown, and K. Pauly, "Localization of ultrasound-induced in vivo neurostimulation in the mouse model," *Ultrasound Med. Biol.*, vol. 40, no. 7, pp. 1512-1522, 2014.

[52] M. Menz, O. Oralkan, P. Yakub, and S. Baccus, "Precise neural stimulation in the retina using focused ultrasound," *J. Neurosci.*, vol. 33, pp. 4550-4560, March 2013.

[53] E. Mace, G. Montaldo, B. Osmanski, I. Cohen, M. Fink, and M. Tanter, "Functional ultrasound imaging of the brain: theory and basic principles," *IEEE Trans. Ultras. Ferr. Freq. Cont.*, vol. 60, pp. 492-506, March 2013.

[54] B. Van Veen and K. Buckley, "Beamforming: a versatile approach to spatial filtering," *IEEE ASSP Mag.*, April 1988.

[55] K. Thomenius, "Evolution of ultrasound beamformers," *IEEE Ultras. Sym.*, 1996.

[56] M. Meng, and M. Kiani, "Design and optimization of ultrasonic wireless power transmission links for millimeter-sized biomedical implants," *IEEE Trans. Biomed. Cir. Syst.*, vol. 11, no. 1, pp. 98-107, February

The invention claimed is:

1. A method of neural stimulation and imaging of a nervous system of a subject, comprising:

providing an interface device operable to generate an ultrasonic beam for direct neuromodulation and imaging of a targeted neural structure of a subject;

implanting the interface device in the subject;

providing and disposing an external coil array over the targeted neural structure of the subject;

generating the ultrasonic beam by the interface device and transmitting the ultrasonic beam towards the targeted neural structure for direct neuromodulating and imaging;

receiving a reflected ultrasonic beam by the interface device from the targeted neural structure for imaging of the targeted neural structure;

wirelessly powering the interface device with the external coil array; and wirelessly communicating between the interface device and the external coil array for performing neuromodulation and imaging of the targeted neural structure.

2. The method of claim 1, further comprising:

providing the interface device comprising at least one ultrasonic transducer operable to focus an ultrasonic beam on the targeted neural structure of brain of the subject for neuromodulation and imaging of the targeted neural structure, and/or comprising at least one sub-millimeter sized ultrasonic transducer operable to generate an ultrasonic point-source near a targeted neural structure of brain of the subject for microscopic ultrasound neuromodulation and imaging of the targeted neural structure;

implanting the at least one ultrasonic transducer in a subdural region located over a brain surface and/or the at least one sub-millimeter sized ultrasonic transducer inside a neural tissue of the brain of the subject; and providing and disposing an external coil array over a skull of the subject, wherein the external coil array is wirelessly powering and communicating with the interface device using an inductive link.

3. The method of claim 1, further comprising:

providing the interface device comprising at least one ultrasonic transducer operable to focus an ultrasonic beam on a targeted neural structure of peripheral nervous system (PNS) of the subject for direct neuromodulation and imaging of the targeted neural structure, and/or comprising at least one sub-millimeter sized ultrasonic transducer operable to generate an ultrasonic point-source near a targeted neural structure of peripheral nervous system (PNS) of the subject for direct microscopic ultrasound neuromodulation and imaging of the targeted neural structure;

implanting the at least one ultrasonic transducer over a nerve bundle of the PNS without any penetration into a parenchyma of the PNS, and/or the at least one sub-millimeter sized ultrasonic transducer in a nerve bundle of the PNS of the subject; and providing and disposing an external coil or ultrasonic transducer array over skin of the subject that is covering the implanted interface device, wherein the external coil or ultrasonic transducer array is wirelessly powering and communicating with the interface device using an inductive or ultrasonic link.

4. An implantable neural stimulation and imaging system for a central nervous system (CNS) of a subject, comprising:
an interface device configured to be implanted in a subdural region located over a brain surface, the interface device comprising at least one ultrasonic transducer operable to focus an ultrasonic beam on a targeted neural structure of the brain for direct neuromodulation and imaging of the targeted neural structure; and
an external coil array disposed over a skull of the subject, the external coil array configured to wirelessly power and communicate with the interface device using an inductive link.

5. The implantable neural stimulation and imaging system according to claim 4, wherein the interface device is driven at a high frequency with a continuous, pulsed or sinusoidal carrier waveform, the carrier waveform being amplitude-modulated with a lower frequency or being reconstructed with a train of sharp pulses with varying amplitudes.

6. The implantable neural stimulation and imaging system according to claim 5, wherein the high frequency is selected from a range of 1-40 MHz and the lower frequency is in a kHz.

7. The implantable neural stimulation and imaging system according to claim 5, wherein the pulsed carrier waveform has a variable number of cycles, pulse repetition frequency and/or duration.

8. The implantable neural stimulation and imaging system according to claim 4, wherein the at least one ultrasonic transducer has a maximum thickness of 0.5 mm.

9. The implantable neural stimulation and imaging system according to claim 4, wherein the interface device comprises at least two ultrasonic transducers that are disposed in either stacked or side-by-side manner.

10. The implantable neural stimulation and imaging system according to claim 4, wherein the at least one ultrasonic transducer comprises zirconate titanate (PZT).

11. The implantable neural stimulation and imaging system according to claim 4, wherein the at least one transducer is operable to focus the ultrasonic beam having a frequency in a range of 1 MHz to 40 MHz.

12. The implantable neural stimulation and imaging system according to claim 4, wherein the at least one transducer has a focal length in a range of 1 mm to 50 mm.

13. The implantable neural stimulation and imaging system according to claim 4, wherein the interface device comprises an array of the at least one ultrasonic transducers to focus on the targeted neural structure.

14. The implantable neural stimulation and imaging system according to claim 4, further comprising:
another interface device configured to be implanted inside the neural tissue of the brain of the subject, the interface device comprising at least one sub-millimeter sized ultrasonic transducer operable to generate an ultrasonic point-source near a targeted neural structure of the brain for direct microscopic ultrasound neuromodulation and imaging of the targeted neural structure; and
the external coil array configured to wirelessly power and communicate with the another interface device using the inductive link.

15. An implantable neural stimulation and imaging system for a peripheral nervous system (PNS) of a subject, comprising:
an interface device configured to be implanted over a nerve bundle of the PNS without any penetration into a parenchyma of the PNS, the interface device comprising at least one ultrasonic transducer operable to focus an ultrasonic beam on a targeted neural structure of the PNS for direct neuromodulation and imaging of the targeted neural structure; and
an external coil or ultrasonic transducer array disposed over skin of the subject that is covering the implanted interface device, the external coil or ultrasonic transducer array configured to wirelessly power and communicate with the interface device using an inductive or ultrasonic link.

16. The implantable neural stimulation and imaging system according to claim 15, wherein the ultrasonic link is based on an ultrasonic harmonic modulation (UHM) technique.

17. The implantable neural stimulation and imaging system according to claim 15, further comprising:
another interface device configured to be implanted in the nerve bundle of the PNS of the subject, the interface device comprising at least one sub-millimeter sized ultrasonic transducer operable to generate an ultrasonic point-source near a targeted neural structure of the PNS for direct microscopic ultrasound neuromodulation and imaging of the targeted neural structure; and
the external coil or ultrasonic transducer array configured to wirelessly power and communicate with the another interface device using an inductive or ultrasonic link.

18. An implantable neural stimulation and imaging system for central nervous system (CNS) of a subject, comprising:
an interface device configured to be implanted inside a neural tissue of a brain of the subject, the interface device comprising at least one sub-millimeter sized ultrasonic transducer operable to generate an ultrasonic point-source near a targeted neural structure of the brain for direct microscopic ultrasound neuromodulation and imaging of the targeted neural structure; and
an external coil array disposed over a skull of the subject, the external coil array configured to wirelessly power and communicate with the interface device using an inductive link.

19. The implantable neural stimulation and imaging system according to claim 18, wherein the at least one sub-millimeter sized ultrasonic transducer is operable to generate the ultrasonic point-source having a frequency in a range of 0.5 MHz to 10 MHz.

20. The implantable neural stimulation and imaging system according to claim 18, wherein the at least one sub-millimeter sized ultrasonic transducer has a focal length in a range of 0.1 mm to 1 mm.

21. The implantable neural stimulation and imaging system according to claim 18, wherein the interface device comprises an array of the at least one sub-millimeter sized ultrasonic transducers to focus on the targeted neural structure.

22. An implantable neural stimulation and imaging system for peripheral nervous system (PNS) of a subject, comprising:
- an interface device configured to be implanted in a nerve bundle of the PNS of the subject, the interface device comprising at least one sub-millimeter sized ultrasonic transducer operable to generate an ultrasonic point-source near a targeted neural structure of the PNS for direct microscopic ultrasound neuromodulation and imaging of the targeted neural structure; and
- an external coil or ultrasonic transducer array disposed over skin of the subject close to the interface device, the external coil or ultrasonic transducer array configured to wirelessly power and communicate with the interface device using an inductive or ultrasonic link.

* * * * *